(12) United States Patent
Maruyama et al.

(10) Patent No.: US 8,603,110 B2
(45) Date of Patent: Dec. 10, 2013

(54) ORGANISM TISSUE SUTURING APPARATUS

(75) Inventors: Tomoji Maruyama, Kanagawa (JP); Masakatsu Kawaura, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 910 days.

(21) Appl. No.: 10/511,441

(22) PCT Filed: Apr. 25, 2003

(86) PCT No.: PCT/JP03/05406
§ 371 (c)(1),
(2), (4) Date: May 3, 2005

(87) PCT Pub. No.: WO03/090628
PCT Pub. Date: Nov. 6, 2003

(65) Prior Publication Data
US 2005/0228405 A1    Oct. 13, 2005

(30) Foreign Application Priority Data

Apr. 25, 2002 (JP) ................. 2002-124829
May 9, 2002 (JP) ................. 2002-133940
May 29, 2002 (JP) ................. 2002-155865

(51) Int. Cl.
*A61B 17/04* (2006.01)

(52) U.S. Cl.
USPC ..................... 606/144; 606/139; 606/148

(58) Field of Classification Search
USPC ................. 606/144, 139, 148
See application file for complete search history.

(56) References Cited

U.S. PATENT DOCUMENTS

| | | | |
|---|---|---|---|
| 5,222,974 A | 6/1993 | Kensey et al. | |
| 5,282,827 A | 2/1994 | Kensey et al. | |
| 5,304,184 A | 4/1994 | Hathaway et al. | |
| 5,364,408 A * | 11/1994 | Gordon | 606/144 |
| 5,814,065 A * | 9/1998 | Diaz | 606/213 |
| 5,855,585 A * | 1/1999 | Kontos | 606/144 |
| 6,096,051 A * | 8/2000 | Kortenbach et al. | 606/144 |
| 7,001,400 B1 * | 2/2006 | Modesitt et al. | 606/144 |

FOREIGN PATENT DOCUMENTS

| | | |
|---|---|---|
| JP | 10-71152 | 3/1998 |
| WO | 94 13211 | 6/1994 |

* cited by examiner

*Primary Examiner* — Gary Jackson
*Assistant Examiner* — Diane Yabut
(74) *Attorney, Agent, or Firm* — Oblon, Spivak, McClelland, Maier & Neustadt, L.L.P.

(57) ABSTRACT

An organism tissue suturing apparatus for suturing a penetrated hole formed subcutaneously in a tissue membrane of an organism includes a body part having a predetermined length. The body part includes a rotary portion, disposed at a front end thereof, that can be inserted into the tissue of the organism from the hole, a needle member accommodated in a portion, inside the body part, rearward from the rotary position, and a pressing mechanism for advancing the needle member from a side surface of the body part and pressing the needle member into the rotary portion. The rotary portion has a needle member receiving portion for receiving essentially a front end of the needle member pressed into the rotary portion by the pressing mechanism, with the rotary portion disposed in the tissue of the organism. The needle member has a suturing thread of a duct for the suturing thread.

16 Claims, 51 Drawing Sheets

FIG. 4
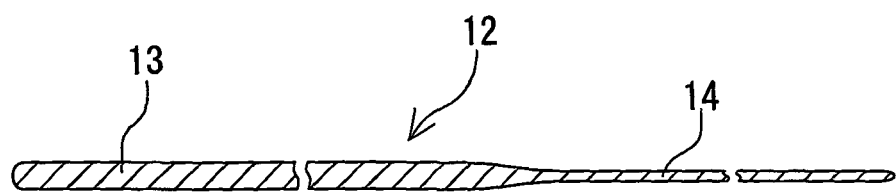
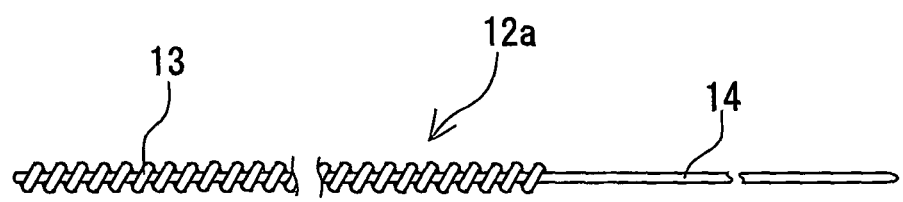
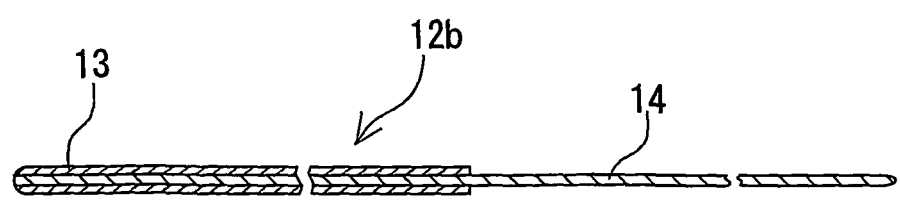
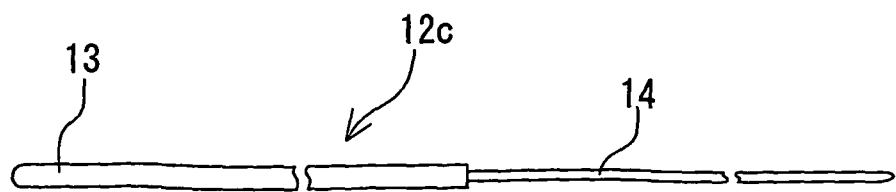

ORGANISM TISSUE SUTURING APPARATUS

TECHNICAL FIELD

The present invention relates to an organism tissue suturing apparatus for suturing a penetrated hole formed subcutaneously in a tissue membrane (for example, blood vessel) of an organism.

BACKGROUND ART

Minimally invasive surgery of inserting a diagnosis device or a treatment device such as a catheter into a blood vessel or an internal structure is widely performed. For example, in treating stricture of the coronary arteries of the heart, it is necessary to insert an instrument such as a catheter into a blood vessel.

The catheter or the like is inserted into the blood vessel from a pierced hole formed by opening the femoral region. Thus it is necessary to stop bleeding from the pierced hole. However, the pressure of the bleeding from the femoral region is high. Thus it is very difficult to stop bleeding. An operator is required to perform a hard work of pressing the hand against the pierced hole for an hour or so in a certain case.

In recent years, apparatuses that are inserted into a patient's body through a wounded hole are developed to suture a hole formed on a blood vessel wall so that the operation of stopping bleeding can be performed easily and securely.

The apparatus of this kind is disclosed in U.S. Pat. No. 5,855,585.

In U.S. Pat. No. 5,855,585, the proximal part and the distal part are connected to each other with the central arch portion extending from the axis of the body of the apparatus, with an interval formed between the end of the proximal part and the proximal end of the distal part. The proximal part has a elastic tube, including the proximal portion and the distal part, extending along the axis having an end which is disposed outside a patient's body when the apparatus is at an operation position; at least one needle-holding cavity formed in the distal part to hold a plurality of needles therein and extending to the open portion formed at the proximal end of the distal part along the axis; the needle pull-in lumen formed in the proximal part and extending to the open portion formed at the distal end of the proximal part along the axis; and the lumen formed at the first end of the proximal part and extending from the open portion to the needle-holding cavity.

It is not easy to insert the central arch portion of the suturing apparatus into the organism. Further in a suturing operation, as shown in FIG. 6B of the specification of U.S. Pat. No. 5,855,585, it is necessary for a doctor to perform an operation of rotating the apparatus in a desired direction and pulling a string outside the open portion while the doctor is pulling one needle forward through the needle-holding cavity. Thereby the proximal end of the needle is pulled through the wall of the blood vessel, and a pointed portion of the needle enters the open portion thus extending into the needle pull-in lumen. Because the string to be pulled is used, the string is pulled forward until the proximal end of the needle advances from the needle pull-in lumen and held with the doctor's fingers. Then the needle is pulled out of the needle pull-in lumen 26. Thereafter as shown in FIG. 7 of the specification of U.S. Pat. No. 5,855,585, the apparatus is rotated until the central arch portion strides the wall of the blood vessel at the position corresponding to the position where the first end of the suturing thread penetrates through the wall of the blood vessel. Then the above-described operation is repeatedly performed.

In this suturing apparatus, it is necessary to insert the arch portion into the organism to suture the hole. The subcutaneous tissue of the patient who has undergone a plurality of catheter operations becomes hard. Thus it is very difficult to insert a projected portion such as the arch portion to the tissue of the organism. Further it is necessary to rotate the entire apparatus inserted into the organism, which makes a suturing operation complicated.

DISCLOSURE OF INVENTION

It is an object of the present invention to provide an organism tissue suturing apparatus that can be easily inserted into a tissue of an organism, facilitates a suturing work, and is capable of securely suturing an opening formed in the tissue of the organism.

In order to achieve the object, there is provided an organism tissue suturing apparatus for suturing a penetrated hole formed subcutaneously in a tissue membrane of an organism that comprises a body part, with a predetermined length, having a rotary portion and can be inserted into said tissue of an organism from said hole; a needle member accommodated in a portion, inside said body part, rearward from said rotary portion; and a pressing mechanism for advancing said needle member from a side surface of said body part and pressing said needle member into said rotary portion, wherein said rotary portion has a needle member receiving portion for receiving essentially a front end of said needle member pressed into said rotary portion by said pressing mechanism, with said rotary portion disposed in said tissue of said organism; and said needle member has a suturing thread or a duct for said suturing thread.

In order to achieve the object, there is provided an organism tissue suturing apparatus for suturing a penetrated hole formed subcutaneously in a tissue membrane of an organism that comprises a body part, with a predetermined length, having a rotary portion and can be inserted into said tissue of said organism from said hole; two hollow needle members accommodated in a portion, inside said body part, rearward from said rotary portion; a needle member operation portion for advancing said hollow needle members toward said rotary portion from a side surface of said body part; and two openings disposed at a rear portion of said body part and communicating with an inside of said two hollow needle members, wherein said rotary portion has two needle member receiving portions for receiving a distal end of one of said hollow needle members and that of the other of said hollow needle members respectively pressed out of said body part; and a connection duct communicating with said two needle member receiving portions; and a duct for a suturing thread is formed in a range from one of said two openings to the other of said openings through an inside of one of said two hollow needle members, said connection duct, and an inside of the other of said two hollow needle members, when said two needle member receiving portions receive said hollow needle members respectively.

In order to achieve the object, there is provided an organism tissue suturing apparatus for suturing a penetrated hole formed subcutaneously in a tissue membrane of an organism that comprises a body part, with a predetermined length, having a rotary portion and can be inserted into said tissue of said organism from said hole; at least one needle accommodated in a portion, inside said body part, rearward from said rotary portion; a thread joined with said needle; and a pressing member for advancing said needle from a side surface of said body part and pressing said needle into said rotary portion, wherein said rotary portion has a needle receiving portion for receiving said needle pressed into said rotary portion by said pressing member, with said rotary portion disposed in said tissue of said organism. In order to achieve the object, there is provided an organism tissue suturing apparatus for suturing a penetrated hole formed subcutaneously in a tissue membrane of an organism that comprises a body part, with a predetermined length, having a rotary portion and can be inserted into said tissue of said organism from said hole; a needle member accommodated inside said body part; an anchor accommodated in said needle member; a thread joined with said anchor; a needle member operation portion for advancing said needle member toward said rotary portion from a side surface, of said body part, disposed at a portion thereof rearward from said rotary portion; and an anchor pressing member for exiting said anchor from a front end of said needle member and pressing said anchor into said rotary portion, wherein said rotary portion has a anchor receiving portion for receiving said anchor pressed into said rotary portion by said anchor pressing member, with said rotary portion disposed in said tissue of said organism.

BRIEF DESCRIPTION OF DRAWING

FIG. 4 is an explanatory view for explaining suturing members for use in the organism tissue suturing apparatus of the present invention.

BEST MODE FOR CARRYING OUT THE INVENTION

An embodiment in which the organism tissue suturing apparatus of the present invention is applied to a blood suturing apparatus is described below. The organism tissue suturing apparatus of the present invention is not limited to the blood suturing apparatus but can be utilized to suture a hole formed in a tissue of an organism. It is to be noted that the left-hand side of FIG. 1 is set as the front (forward) side, whereas the right-hand side of FIG. 1 is set as the rear (rearward) side.

Figure 1:
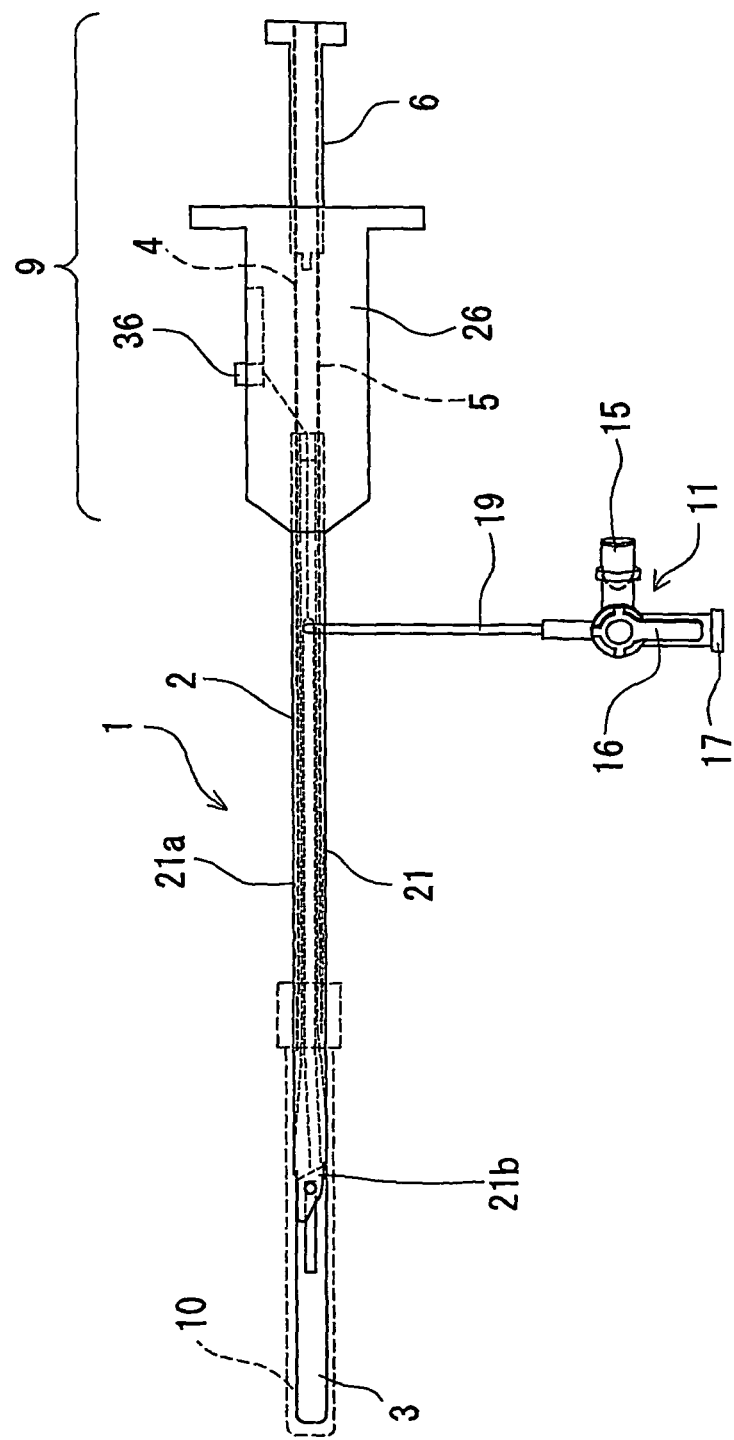
FIG. 1 shows an outlook of an organism tissue suturing apparatus according to an embodiment of the present invention.
Figure 2:
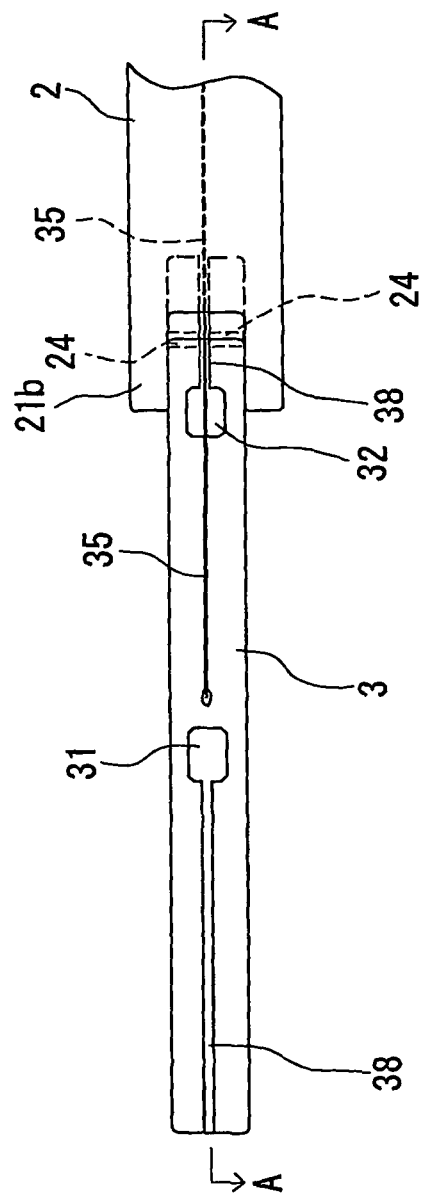
FIG. 2 is an enlarged plan view showing a front side of the organism tissue suturing apparatus shown in FIG. 1.
Figure 3:
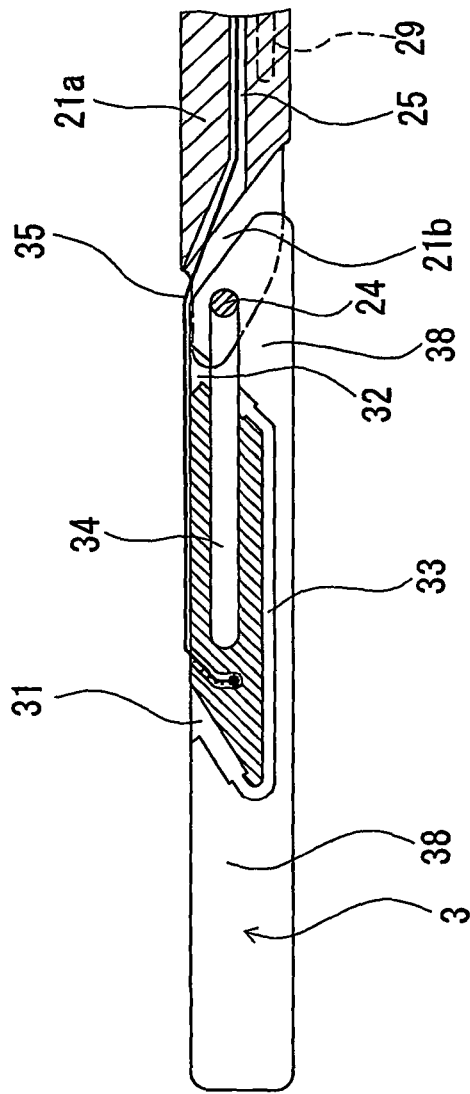
FIG. 3 is a sectional view taken along a line A-A of FIG. 2.
Figure 5:
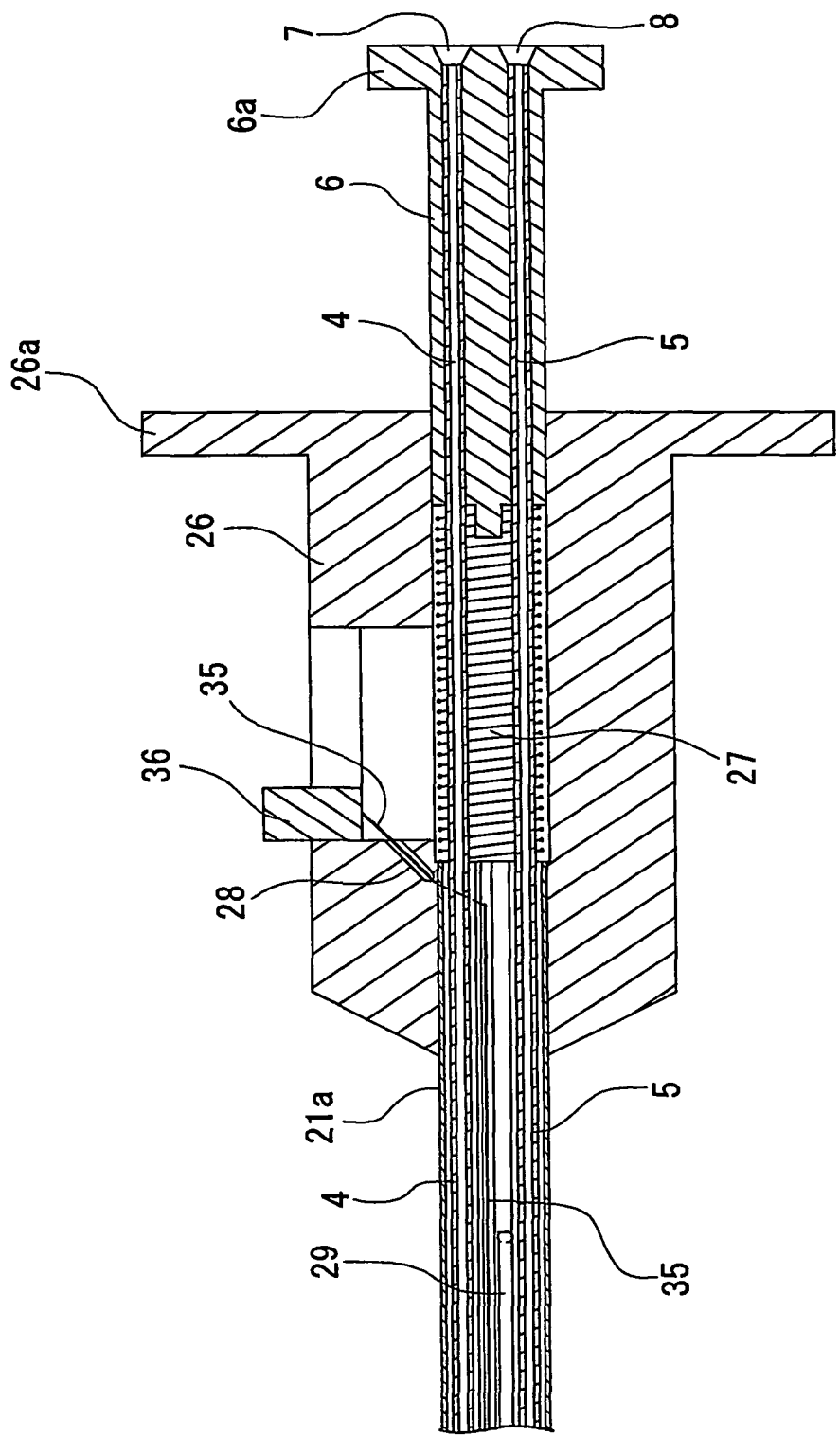
FIG. 5 is an enlarged sectional view of a rear side of the organism tissue suturing apparatus shown in FIG. 1.
Figure 6:
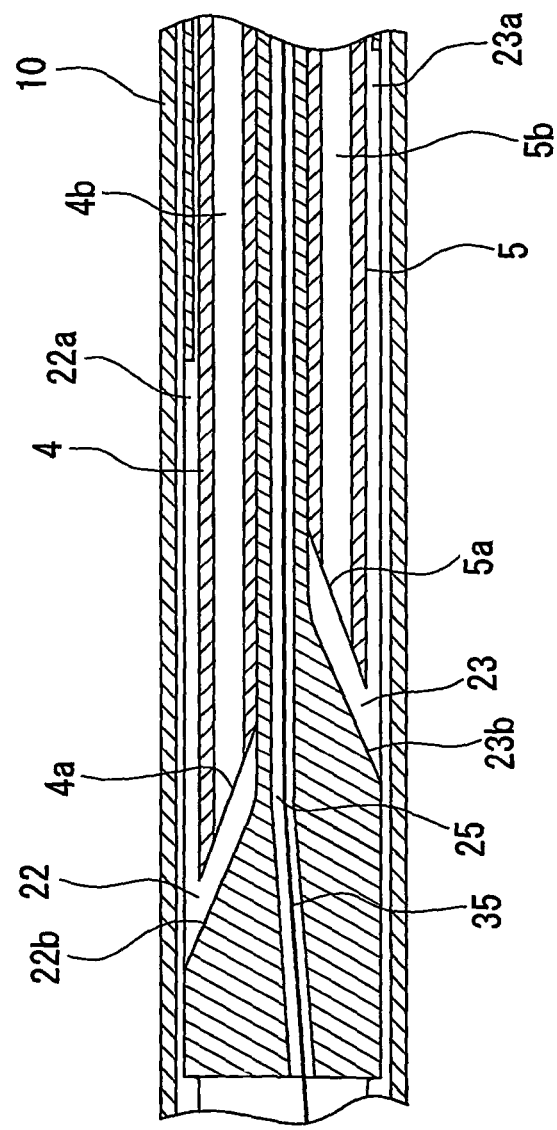
FIG. 6 is an enlarged sectional view showing the vicinity of a front end of a hollow needle member of a body part of the organism tissue suturing apparatus shown in FIG. 1.

FIG. 1 shows an outlook of an organism tissue suturing apparatus according to an embodiment of the present invention. FIG. 2 is an enlarged plan view showing a front side of the organism tissue suturing apparatus shown in FIG. 1. FIG. 3 is a sectional view taken along a line A-A of FIG. 2. FIG. 4 are an explanatory view respectively for explaining a suturing member for use in the organism tissue suturing apparatus of the present invention. FIG. 5 is an enlarged sectional view of a rear side of the organism tissue suturing apparatus shown in FIG. 1. FIG. 6 is an enlarged sectional view showing the vicinity of a front end portion of a hollow needle member of a body part of the organism tissue suturing apparatus shown in FIG. 1.

An organism tissue suturing apparatus of the present invention for suturing a penetrated hole formed subcutaneously in a tissue membrane of an organism includes a body part having a predetermined length. The body parts includes a rotary portion, disposed at a front end thereof, that can be inserted into the tissue of the organism from the hole; a needle member accommodated in a portion, inside the body part, rearward from the rotary portion; and a pressing mechanism for advancing the needle member from a side surface of the body part and pressing the needle member into the rotary portion. The rotary portion has a needle member receiving portion for receiving essentially a front end of the needle member pressed into the rotary portion by the pressing mechanism, with the rotary portion disposed in the tissue of the organism. The needle member has a suturing thread or a duct for the suturing thread.

The organism tissue suturing apparatus 1 of the embodiment is used to suture a penetrated hole formed subcutaneously in a tissue membrane of an organism. The organism tissue suturing apparatus 1 has a body part 2, with a predetermined length, having a rotary portion 3 that can be inserted into the tissue of the organism and is rotatable in the tissue of the organism. An operation part 9 is disposed at a rear portion of the body part 2. The body part 2 has hollow needle members 4, 5 accommodated therein; a needle member operation (pressing) portion 6 for advancing the hollow needle members 4, 5 toward the rotary portion 3 from a side surface of the body part 2 at its front side; and openings 7, 8 disposed at a rear portion of the body part 2 and communicating with the inside of the hollow needle members 4, 5 respectively. The rotary portion 3 has needle member receiving portions 31, 32 for receiving a front end of the hollow needle member 4 and that of the hollow needle member 5 respectively pressed out of the body part 2; and a connection duct 33 communicating with the needle member receiving portions 31, 32. In the organism tissue suturing apparatus 1, a duct for a suturing thread is formed from one opening 7 to the other opening 8 through the inside of the hollow needle member 4, the connection duct 33, and the inside of the hollow needle member 5, when the needle member receiving portions 31, 32 receive the hollow needle members 4 and 5 respectively.

The organism tissue suturing apparatus 1 has a suturing member 12 that is inserted into the duct for the suturing thread when it is used. The suturing member 12 has a guide portion 13 that can be inserted into the duct for the suturing thread and a suturing thread portion 14 having a smaller outer diameter than the guide portion 13.

As shown in FIGS. 1, 5, and 6, the body part 2 has a shaft 21 having accommodation portions 22, 23 formed on a side surface of the shaft 21 and extending axially; and a hub (shaft hub) 26 disposed at a rear end of the shaft 21. As shown in FIG. 1, the shaft 21 has a body portion 21a in which the accommodation portions 22, 23 are formed; and a front end 21b, extending forward from a front end of the body portion 21a, for rotatably supporting the rotary portion 3. As shown in FIG. 6, it is preferable that the accommodation portion 22 is a lumen having a side-surface opening 22a at its front side. Similarly, as shown in FIG. 6, it is preferable that the accommodation portion 23 is a lumen having a side-surface opening 23a at its front side. The accommodation portions 22, 23 may be a groove whose side surface is entirely open. The shaft 21 accommodates a lumen 25 (see FIG. 3) extending axially. It is preferable that the shaft 21 has a length of 30 to 700 mm and has an outer diameter of 1.0 to 10.0 mm.

It is possible to use the following macromolecular materials for the shaft 21: polyolefin such as polypropylene, polyethylene, and the like, olefin elastomer (for example, polyethylene elastomer, polypropylene elastomer), polyester such as polyethylene terephthalate, flexible polyvinyl chloride, polyurethane, urethane elastomer, polyamide, amide elastomer (for example, polyamide elastomer), polytetrafluoroethylene, fluorocarbon resin elastomer, polyimide, ethylene-polyvinyl chloride copolymer, and silicone rubber; and metals such as stairdess steel, Ni—Ti alloy, Cu—Zn alloy, Ni—Al alloy, tungsten, tungsten alloy, titanium, titanium alloy, cobalt alloy, tantalum; and an appropriate combination of these substances.

The accommodation portions 22, 23 of the shaft 21 accommodate the hollow needle members 4, 5 respectively. The needle member operation portion 6 for advancing the hollow needle members 4, 5 from the body part 2 is disposed at the rear portion (preferably, rear end) of each of the hollow needle members 4, 5. As shown in FIG. 6, the hollow needle members 4, 5 have cutting faces 4a, 5a formed at the front end thereof respectively and inner ducts 4b, 5b formed therein respectively. It is preferable that each of the hollow needle members 4, 5 has an outer diameter of 0.1 mm to 1.0 mm, has an inner diameter of 0.05 mm to 0.95 mm, and a length of 30 mm to 800 mm.

It is possible to use the following materials for the hollow needle members 4, 5: Metals such as stainless steel, Ni—Ti alloy, Cu—Zn alloy, Ni—Al alloy, tungsten, tungsten alloy, titanium, titanium alloy, cobalt alloy, tantalum; macromolecular materials having a comparatively high rigidity such as polyamide, polyimide, ultra-high-molecular-weight polyethylene, polypropylene, fluorocarbon resin; and a combination of these substances.

Resins having low frictional properties may be applied to the side surface of each of the hollow needle members 4, 5 to increase the lubricity thereof. As the resins having low frictional properties, it is possible to use fluorocarbon resin, nylon 66, polyether ether ketone, and high-density polyethylene. The fluorocarbon resin is more favorable than other resins. As the fluorocarbon resin, it is possible to use polytetrafluoroethylene, polyvinylidene fluoride, ethylene tetrafluoroethylene, and perfluoroalkoxy resin. Polytetrafluoroethylene is more favorable than the other fluorocarbon resins. Silicon or hydrophilic resins may be applied to the side surface of each of the hollow needle members 4, 5.

The hollow needle members 4, 5 do not necessarily have to be hollow to the rear end thereof. For example, the hollow needle members 4, 5 may be hollow to the openings 7, 8 which are disposed at the rear end of the body part 2 and communicate with the inside of the hollow needle members 4, 5.

The accommodation portions 22, 23 are formed inside the shaft 21 at positions in the vicinity of the side surface thereof. The accommodation portions 22, 23 extend parallel with the axis of the shaft 21 to accommodate the hollow needle members 4, 5 therein respectively. At the front end portion of the accommodation portions 22, 23, there are formed guide portions 22b, 23b for respectively advancing the hollow needle members 4, 5 obliquely and forwardly from the side surface of the body part 2. The guide portions 22b, 23b are formed by inclining the inner surface of the front end of the accommodation portions 22, 23 respectively toward the side surface of the shaft 21. It is preferable that the distance between the front end of the guide portions 22b, 23b and that of the body portion 21a of the shaft 21 is 3.0 mm to 60.0 mm. As shown in FIG. 6, the guide portion 23b of the second accommodation portion 23 is disposed a little nearer to the rear end of the body part 2 than the guide portion 22b of the first accommodation portion 22 so that the hollow needle member 5 advances a little nearer to the rear end of the body part 2 than the hollow needle member 4. That is, the front end of the second guide portion 23b is disposed nearer to the rear end of the body part 2 than the front end of the first guide portion 22b. This construction is suitable for suturing a blood vessel through an oblique (for example, 30 degrees to 60 degrees) hole formed subcutaneously in penetration through the tissue membrane of the organism.

As shown in FIGS. 1 and 5, the body part 2 has a hub 26 disposed at its rear side. The hub 26 has a duct accommodating the rear side of each of the hollow needle members 4, 5. The hub 26 has a flange portion 26a to be operated by an operator.

As shown in FIGS. 1 and 5, each of the hollow needle members 4, 5 extends to the rear end of the shaft 21 through the accommodation portion, thus protruding rearward from the rear end of the shaft 21 and extending rearward inside the duct of the hub 26. The rear end of each of the hollow needle members 4, 5 is stopped to the needle member operation portion 6 slidable in the duct of the hub 26. Therefore by pressing the needle member operation portion 6 forward, the hollow needle members 4, 5 can be moved forward and the front portion thereof can be pressed out of the body part 2. The needle member operation portion 6 may be provided for each of the hollow needle members 4, 5. It is preferable that the hollow needle members 4, 5 are urged by an urging means in a direction in which they do not advance. More specifically, the needle member operation portion 6 is always urged rearward by a elastic member 27 accommodated in the duct of the hub 26. It is preferable that as shown in FIG. 5, a coil spring is used as the elastic member 27. The elastic member 27 may be provided between the flange portion 6a of the needle member operation portion 6 and the hub 26.

The organism tissue suturing apparatus 1 has the openings 7, 8 disposed at the rear portion (preferably, rear end) of the body part 2 and communicating with the hollow needle members 4, 5 respectively. In the organism tissue suturing apparatus 1, each of the hollow needle members 4, 5 terminates inside the needle member operation portion 6. The openings 7, 8 are formed at the rear end of the duct of the needle member operation portion 6. The diameter of each of the openings 7, 8 becomes gradually larger toward the rear end thereof. Each of the hollow needle members 4, 5 may extend to the rear end of the needle member operation portion 6 to form openings respectively at the rear end thereof. In addition, an opening may be formed on the side surface of each of the hollow needle members 4, 5, and two openings may be formed on the side surface of the shaft 21 at its rear portion in such a way that the positions of the two openings of the hollow needle members 4, 5 correspond to the positions of the openings formed on the shaft 21, when the needle member operation portion 6 is operated. Thereby the two openings of the hollow needle members 4, 5 and those of the shaft 21 communicate respectively.

As shown in FIG. 3, the rotary portion 3 including the needle member receiving portions 31, 32 for receiving the front end portion of the hollow needle members 4, 5 respectively and the connection duct 33 communicating with the needle member receiving portions 31, 32 is rotatably supported at the front end 21b of the shaft 21. In the organism tissue suturing apparatus 1 of the embodiment, the body part 2 has a supporting pin 24 for rotatably supporting the rotary portion 3. The rotary portion 3 has a side-surface opening (in other words, slit for sliding supporting pin 24) 34 long and axially extending to receive the supporting pin 24 and allow sliding of the supporting pin 24.

The organism tissue suturing apparatus 1 has a rotary portion towing wire 35 which extends inside the body part 2 and is fixed to the rotary portion 3 at one end thereof. The rotary portion towing wire 35 is provided with a wire operation portion 36 at its other end. The towing wire 35 penetrates through a lumen 25 formed inside the body portion 21a of the shaft 21. One end of the towing wire 35 penetrates into and is fixed to a concavity formed inwardly in the rotary portion 3. The concavity is disposed in the vicinity of the center of the rotary portion 3 in the front-to-back direction thereof. As shown in FIG. 5, the other end of the towing wire 35 protrudes from the side surface of the rear end of the body portion 21a of the shaft 21, passes through a duct 28 formed inside the hub 26, and is fixed to the wire operation portion 36. The wire operation portion 36 is slidable inside a long opening formed on the side surface of the hub 26. By pulling the towing wire 35 rearward, namely, by moving the wire operation portion 36 rearward, the rotary portion 3 moves rearward from the state shown in FIG. 8 to the state shown in FIG. 9. By allowing the rotary portion 3 to slide on the front end 21b of the body part 2, it is possible to reduce the length of the front side part of the body part for storing a proximal portion of the rotary portion 3 (in other words, front end 21b of shaft 21) rotatably supporting the rotary portion 3. Consequently it is possible to reduce the distance between the front end portion of the hollow needle member and the rotary portion during a suturing work. Thereby a piercing stroke of the hollow needle member can be shortened in a suturing work. It is possible be reduce the length of the body part 2 that must insert it into the blood vessel.

FIG. 3 is a sectional view taken along a line A-A of FIG. 2. More specifically, FIG. 3 is a sectional view obtained by cutting the rotary portion 3 at the center of a towing wire mounting portion along a line parallel with the axial direction of the organism tissue suturing apparatus. As shown in FIGS. 2 and 3, the rotary portion 3 has the needle member receiving portions 31, 32 open at the upper end thereof. An open portion of the needle member receiving portions 31, 32 disposed at the upper end thereof forms a guide portion respectively for guiding the front end of the hollow needle members 4, 5. The needle member receiving portions 31 and 32 communicate with each other through the connection duct 33. As shown in FIG. 3, the connection duct 33 communicates with the needle member receiving portion 31 at its one end, extends toward the rear end of the rotary portion 3, and is curved. The other end of the connection duct 33 communicates with the needle member receiving portion 32. The rotary portion 3 has a thread pull-out slit 38 (area in FIG. 3 not having hatched portion) which communicates with the needle member receiving portions 31, 32 and the connection duct 33 and which surrounds the connection duct 33. That is, the rotary portion 3 has a connection portion (hatched area in FIG. 3) only in the central portion and is divided into right and left portions. The thread pull-out slit 38 is narrower than the connection duct 33. The suturing thread portion 14 is capable of passing through the thread pull-out slit 38, but the guide portion 13 is incapable of passing therethrough. The thread pull-out slit 38 may be formed obliquely to avoid that the thread pull-out slit 38 becomes the front of the connection duct 33.

It is preferable that the rotary portion 3 has a width of 0.5 to 9.0 mm; a height of 0.8 to 10.0 mm, a length of 2.0 to 6.0 mm.

The sectional area of the needle member receiving portions 31, 32 shown in FIG. 2 is much larger than that of the outer diameter of the hollow needle members 4, 5 at the front end portion thereof. The sectional area of the connection duct 33 in the axial direction of the body part 2 is larger than that of the guide portion 13 of the suturing member 12. It is preferable that the width of the thread pull-out slit 38 is equal to or larger than that of a suturing thread to be used. It is preferable that the width of the thread pull-out slit 38 is smaller than that of the outer diameter of the guide portion 13 of the suturing member 12 to be used. The portion of the thread pull-out slit 38 of the rotary portion 3 may be made of an elastic material. In that case, so the width of the thread pull-out slit is 0 mm in a normal state, it is possible to expand the thread pull-out slit 38 owing to a tensile force generated, when the suturing thread portion 14 is pulled out of the organism tissue suturing apparatus 1. Thereby the suturing thread portion 14 can be pulled out of the thread pull-out slit 38. As the elastic material, it is possible to use the following materials: macromolecular materials including polyolefin such as polypropylene, polyethylene, and the like, olefin elastomer (for example, polyethylene elastomer, polypropylene elastomer), polyester such as polyethylene terephthalate, flexible polyvinyl chloride, polyurethane, urethane elastomer, polyamide, amide elastomer (for example, polyamide elastomer), polytetrafluoroethylene, fluorocarbon resin elastomer, polyimide, ethylene-polyvinyl chloride copolymer, and silicone rubber.

It is possible to use the following materials for the rotary portion: Metals such as stainless steel, Ni—Ti alloy, Cu—Zn alloy, Ni—Al alloy, tungsten, tungsten alloy, titanium, titanium alloy, cobalt alloy, tantalum; macromolecular materials having a comparatively high rigidity such as polyamide, polyimide, ultra-high-molecular-weight polyethylene, polypropylene, fluorocarbon resin; and a combination of these substances.

As shown in FIGS. 1 and 5, the organism tissue suturing apparatus 1 has a liquid-filing lumen 29, extending inside the body part 2, whose one end is open at a position in the vicinity of a front end thereof which can be inserted into the tissue of the organism and whose other end is open at the rear side of the body part 2; a three-way cock 11 connected to the liquid-filling lumen 29; a pulsation confirmation member 15 mounted on one port of the three-way cock 11; and a liquid-filling port 17 formed on another port of the three-way cock 11. The three-way cock 11 has an operation portion 16 for selectively communicating the liquid-filling lumen 29 with one port thereof and another port thereof. The three-way cock 11 is connected to the body part 2 through a connection tube 19. The pulsation confirmation member 15 allows the operator from outside to visually observe a liquid surface that is deformed by a pressure applied to a liquid filled inside the three-way cock 11. The pulsation confirmation member 15 may have a pressure-sensitive film which is deformed by a change of the pressure applied to the liquid filled inside the three-way cock 11. As the liquid to be filled inside the three-way cock 11, physiologic saline can be preferably used.

Figure 7:
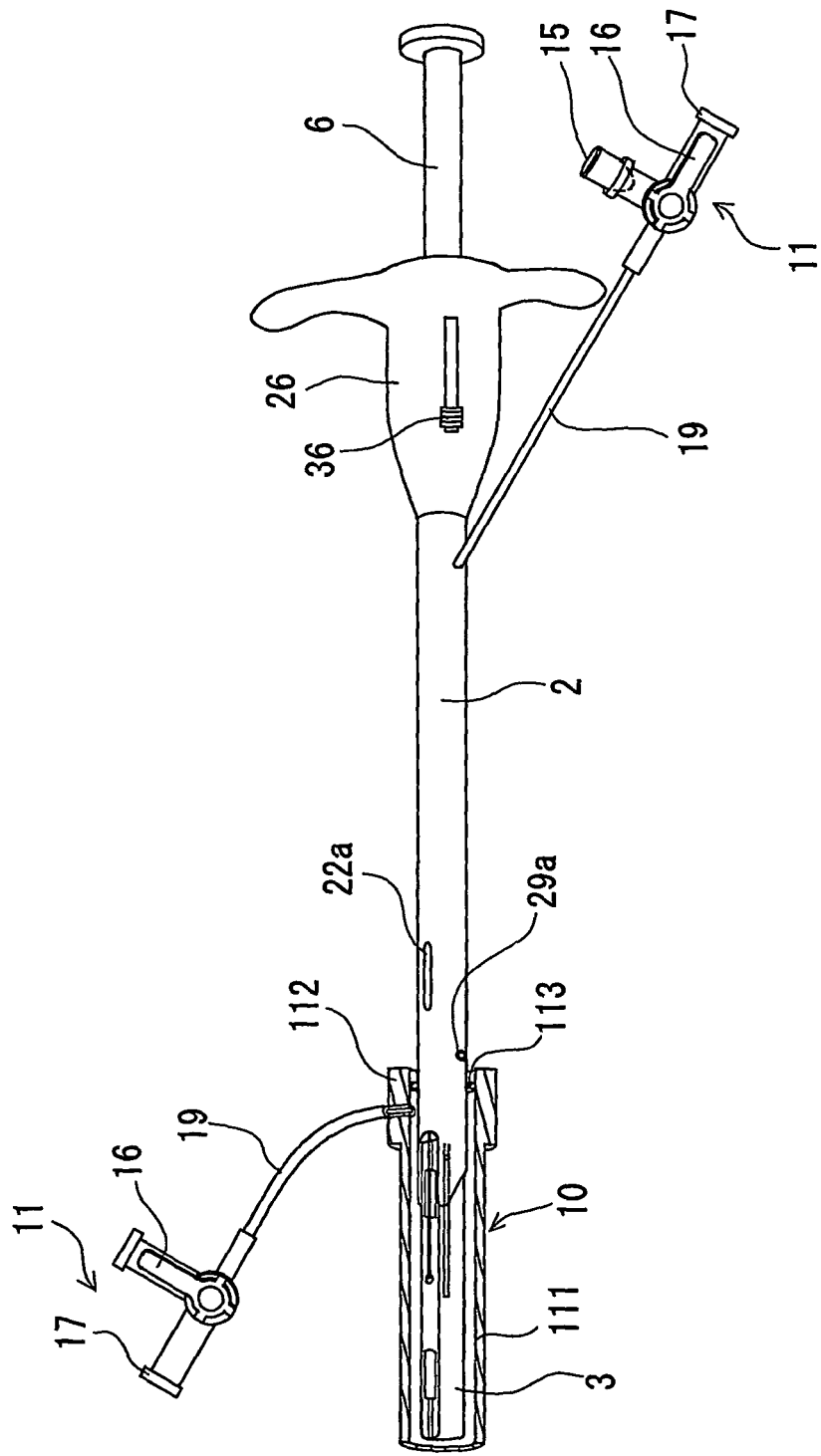
FIG. 7 is an explanatory view for explaining the operation of the organism tissue suturing apparatus of the present invention.

As a cylindrical sheath 10 shown in FIG. 7, an introducer sheath that is utilized for a catheter operation and inserted in the blood vessel can be used.

Figure 12:
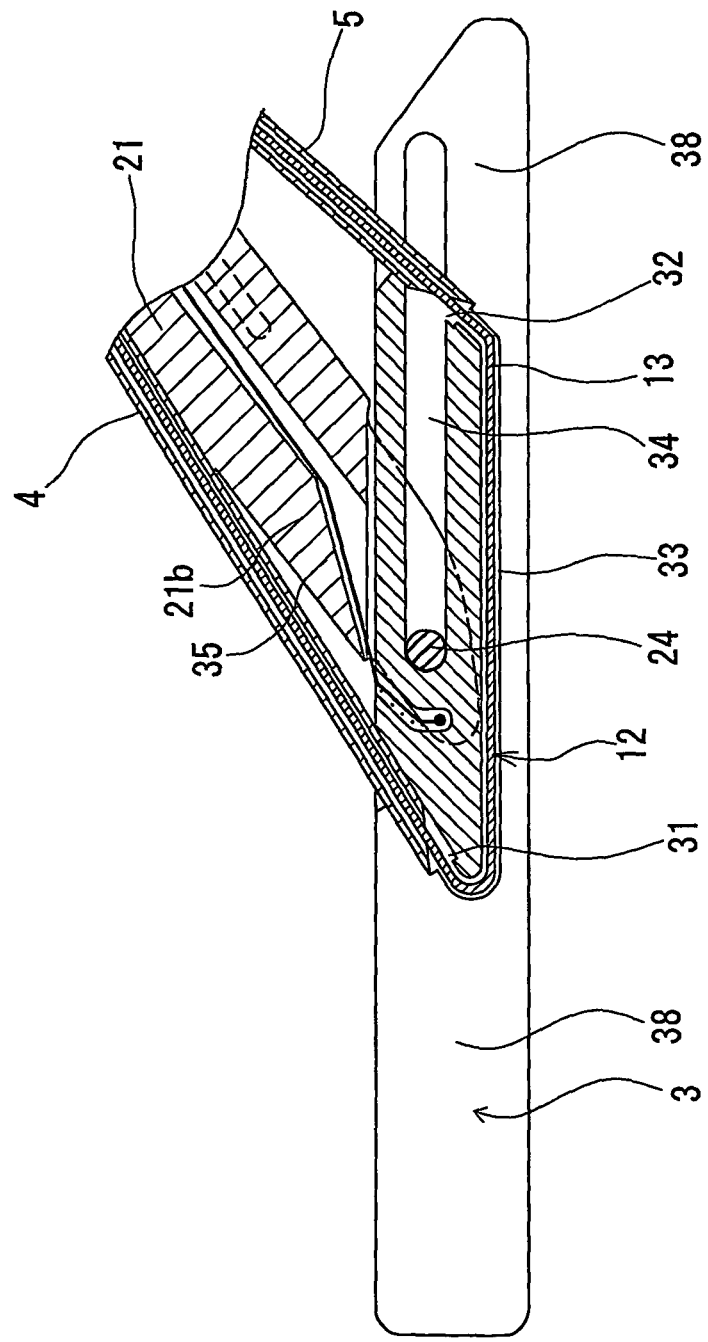
FIG. 12 is an explanatory view for explaining the operation of the organism tissue suturing apparatus of the present invention.
Figure 13:
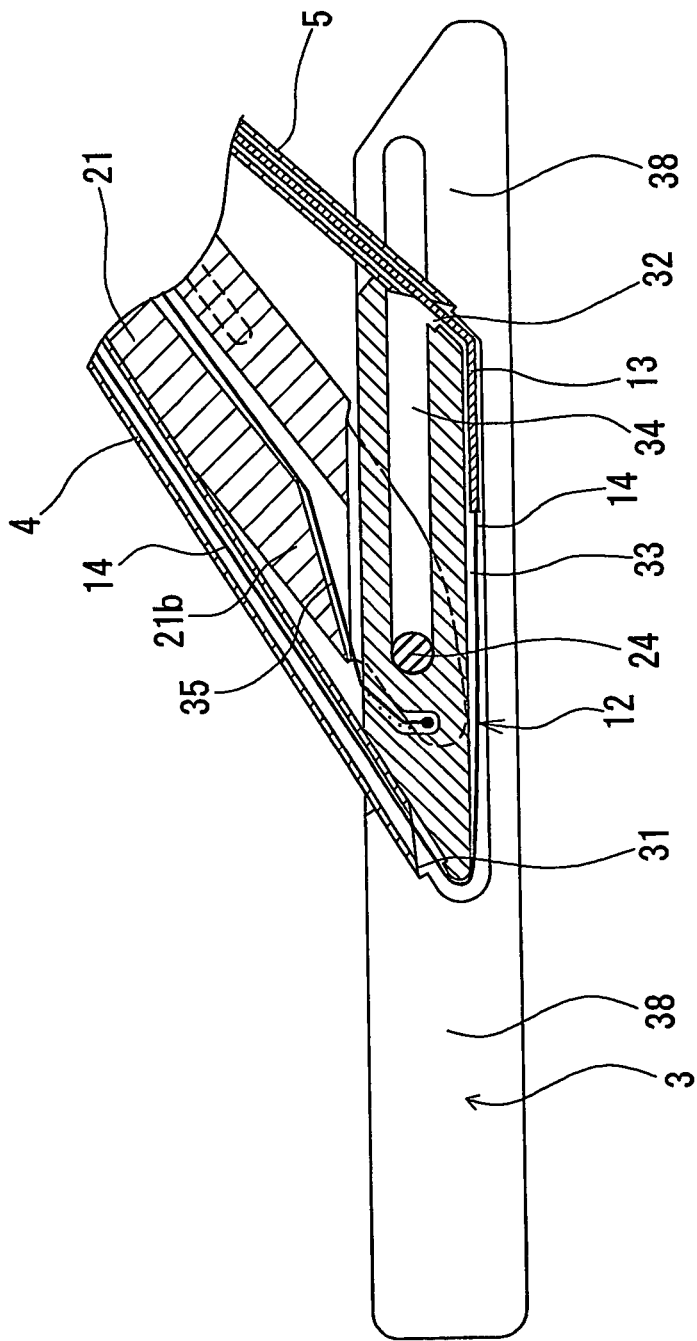
FIG. 13 is an explanatory view for explaining the operation of the organism tissue suturing apparatus of the present invention.
Figure 14:
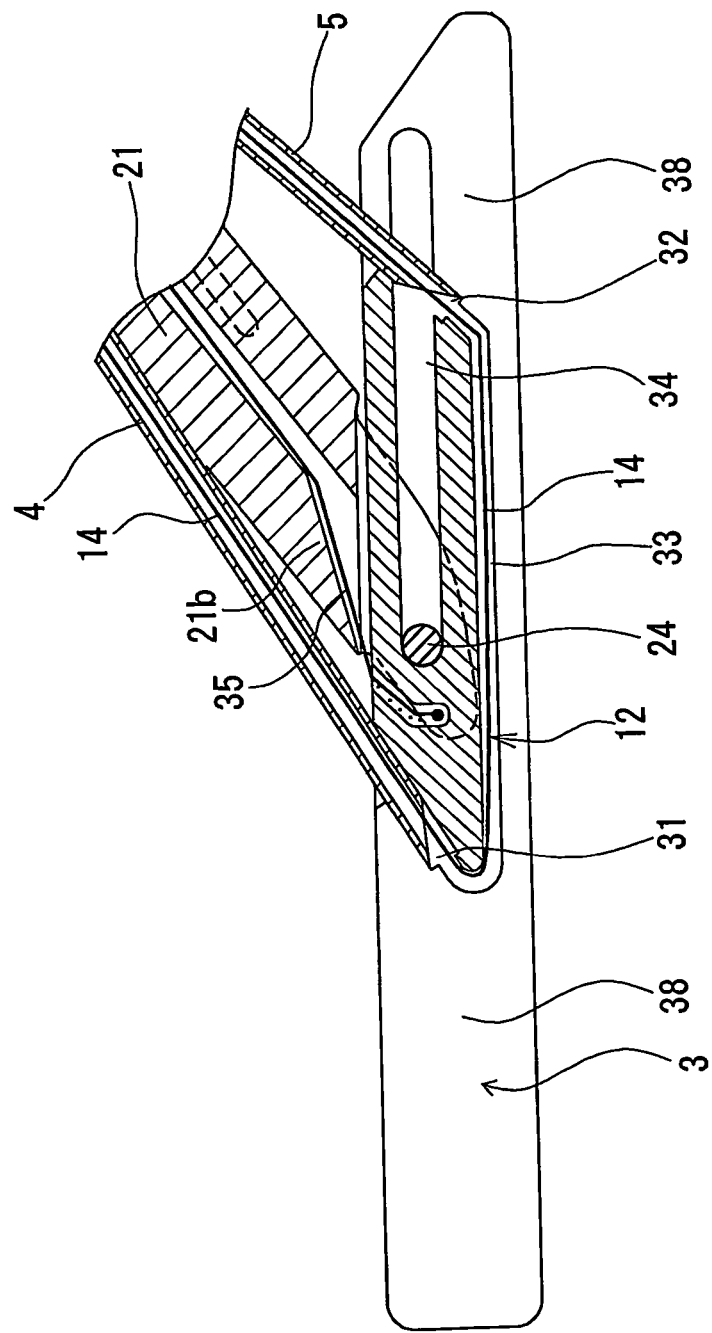
FIG. 14 is an explanatory view for explaining the operation of the organism tissue suturing apparatus of the present invention.
Figure 15:
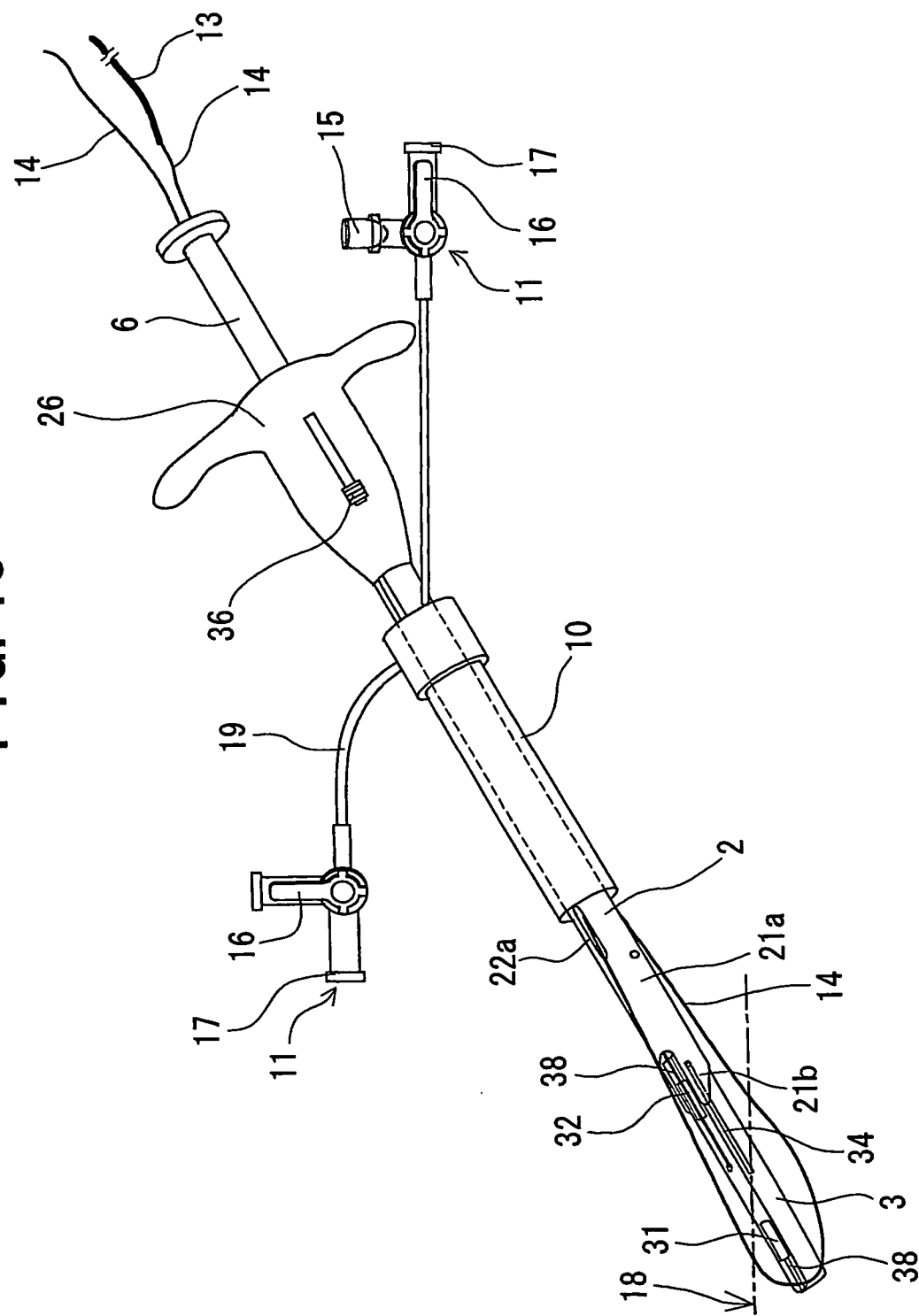
FIG. 15 is an explanatory view for explaining the operation of the organism tissue suturing apparatus of the present invention.

As shown in FIGS. 12, 13, and 14, the suturing member 12 for use in the organism tissue suturing apparatus 1 is linear and includes the guide portion 13 at its front end and the suturing thread portion 14 at its rear end. It is preferable that the outer diameter of the guide portion 13 is 0.1 to 1.0 mm and that the length thereof is longer than the entire length of the duct for the suturing thread formed inside the organism tissue suturing apparatus 1. More specifically, it is preferable that the length of the guide portion 13 is longer than the length of the duct for the suturing thread formed inside the organism tissue suturing apparatus 1 by 20 to 100 mm. It is preferable that the guide portion 13 has a length of 60 to 1600 mm.

The outer diameter of the guide portion 13 is larger than that of the suturing thread portion 14 to thereby allow only the suturing thread portion 14 to pass through the thread pull-out slit 38 without the guide portion 13. As the construction of the suturing member 12, it is possible to utilize the following four constructions: In the suturing member 12 shown in FIG. 4, the guide portion 13 and the suturing thread portion 14 are made of the same thread material and a portion in the vicinity of the center of the suturing member 12 is tapered; In the suturing member 12a shown in FIG. 4, a coil-shaped or blade-shaped elastic material is wound on an end of the guide portion 13 to which a thread material constituting the suturing thread portion 14 extends to thereby form the guide portion 13; The suturing member 12b shown in FIG. 4 has a two-layer construction in which only the guide portion 13 is covered with an elastic material; The suturing member 12 (not shown) having a composite construction in which a wire as shown in FIG. 4 is wound on the construction as shown in FIG. 4; and in the suturing member 12c shown in FIG. 4, the guide portion 13 and the suturing thread portion 14 are made of different materials, having different outer diameters, joined with each other.

Elastic metal or flexible resin is preferable as elastic materials for the above-described construction. A super-elastic alloy is preferable as the elastic metal. The super-elastic alloy is called a shape memory alloy. The super-elastic alloy shows elasticity at the normal temperature of the organism (in the vicinity of 37° C.). A Ti—Ni alloy having an atomic percent of 49 to 53 is particularly preferable. In addition, a Ti—Ni—X (X=Co, Fe, Mn, Cr, V, Al, Nb, W, and B) alloy is obtained by replacing a part of the Ti—Ni alloy with X having an atomic percent of 0.01 to 10.0. Further a Ti—Ni—X (X=Cu, Pb, Zr) alloy is obtained by replacing a part of the Ti—Ni alloy with X having an atomic percent of 0.01 to 30.0. By using these Ti—Ni—X alloys, it is possible to change the mechanical characteristic of the Ti—Ni alloy by appropriately selecting the cooling processing rate or/and the condition of final heat treatment. As the flexible resins, it is possible to use the following macromolecular materials: Polyolefin such as polypropylene, polyethylene, and the like, olefin elastomer (for example, polyethylene elastomer, polypropylene elastomer), polyester such as polyethylene terephthalate, flexible polyvinyl chloride, polyurethane, urethane elastomer, polyamide, amide elastomer (for example, polyamide elastomer), polytetrafluoroethylene, fluorocarbon resin elastomer, polyimide, ethylene-polyvinyl chloride copolymer, and silicone rubber; and an appropriate combination of these substances. Resins having low frictional properties may be applied to the side surface of the guide portion 13 or its outer surface to increase the lubricity thereof. As the resins having low frictional properties, it is possible to use the above-described substances.

As the material for the suturing thread portion 14, known thread materials can be used. It is possible to use a thread material that is absorbed or not absorbed by the organism. It is preferable that a thread has a thickness of 0.01 to 0.90 mm and a length of 60 to 1600 mm.

The operation of the organism tissue suturing apparatus 1 of the present invention is described below with reference to FIGS. 9 through 16.

Figure 16:
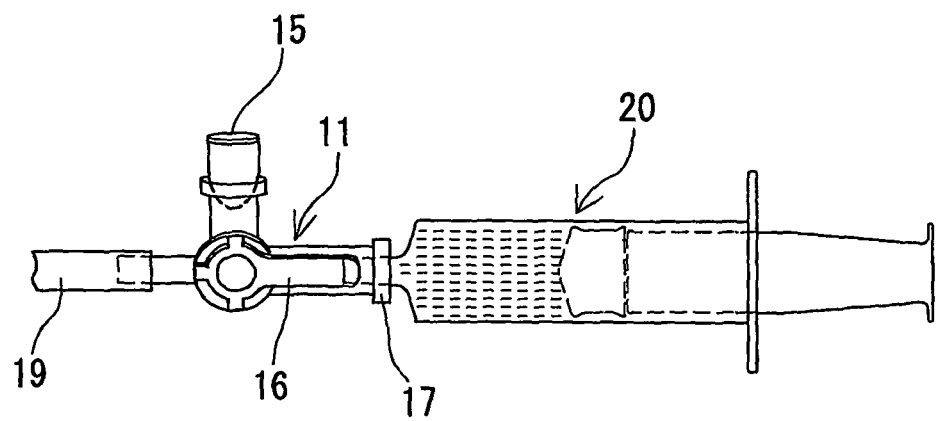
FIG. 16 is an explanatory view for explaining a pressure detection function provided on the organism tissue suturing apparatus of the present invention.

As shown in FIGS. 7 and 16, initially a liquid injection instrument 20 containing a liquid is mounted on the liquid-filling port 17 of the three-way cock 11. Thereafter with the pulsation confirmation member 15 removed from one port of the three-way cock 11, the liquid-filling port 17 and the liquid-filling lumen 29 are communicated with each other. Then a plunger of the liquid injection instrument 20 is pressed to fill the liquid into the lumen 29. Then the pulsation confirmation member 15 is mounted on a pulsation confirmation member installing port, and the operation portion 16 is switched to communicate the pulsation confirmation member installing port and the liquid-filling lumen 29 with each other. By filling the liquid into the lumen, it is possible to prevent blood from being exposed to the outside from the three-way cock 11. Further discarding of blood can be prevented, because the blood is not filled into the lumen 29 nor the three-way cock 11.

Figure 8:
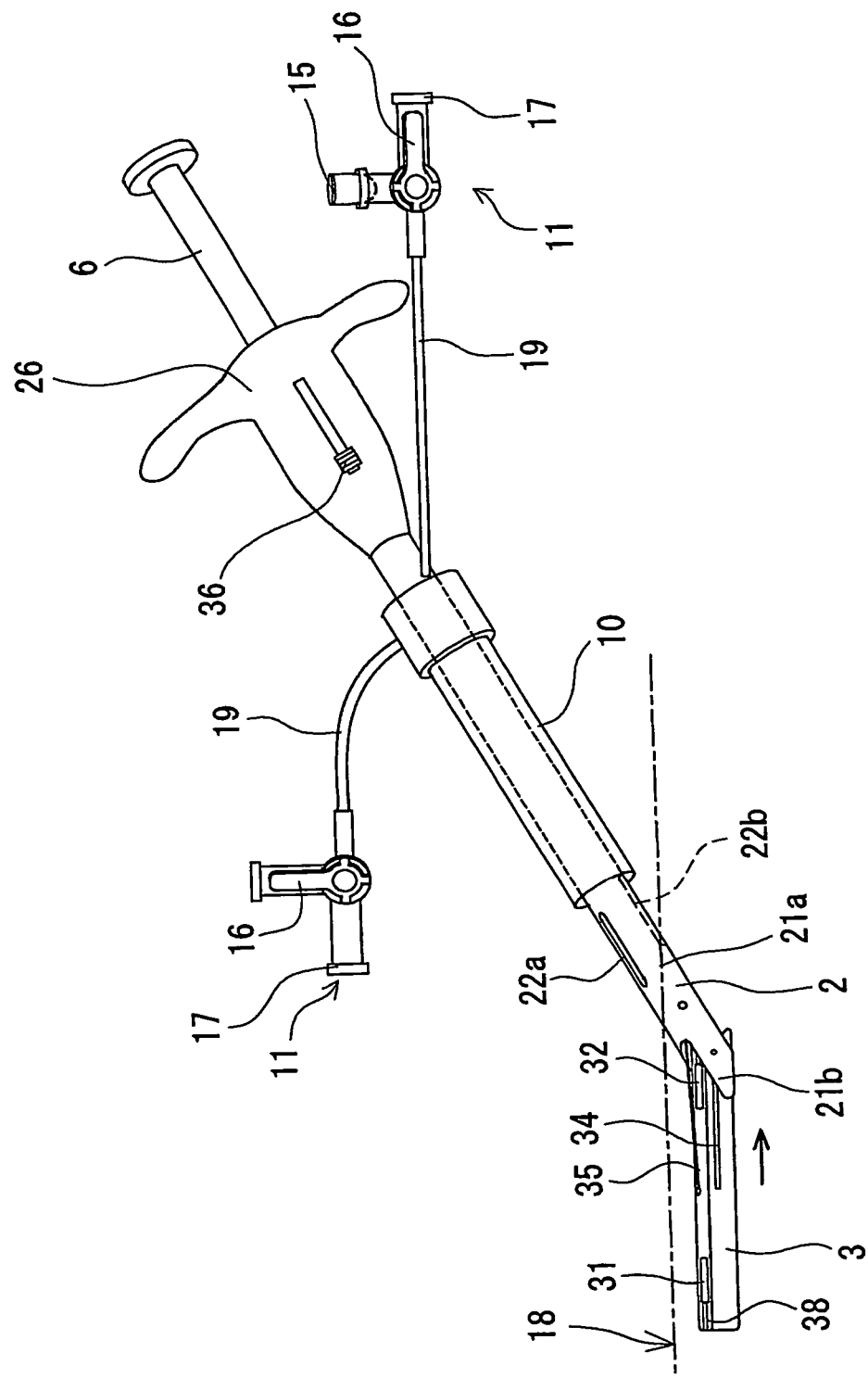
FIG. 8 is an explanatory view for explaining the operation of the organism tissue suturing apparatus of the present invention.

Thereafter the organism tissue suturing apparatus 1 is inserted into the introducer sheath 10, for use in treatment or diagnosis, whose front end has reached the tissue of the organism through the hole formed in the tissue membrane of the organism. The rotary portion 3 of the organism tissue suturing apparatus 1 and the front end 29a of the body part 2 are inserted into the tissue of the organism (into blood). FIG. 8 shows this state. Pulsation of the interface between the liquid filled in the pulsation confirmation member (in other words, pulsation indicator cap) 15 and air is confirmed. The broken lines 18 of the drawings show a blood vessel wall which is the tissue membrane of the organism.

Figure 9:
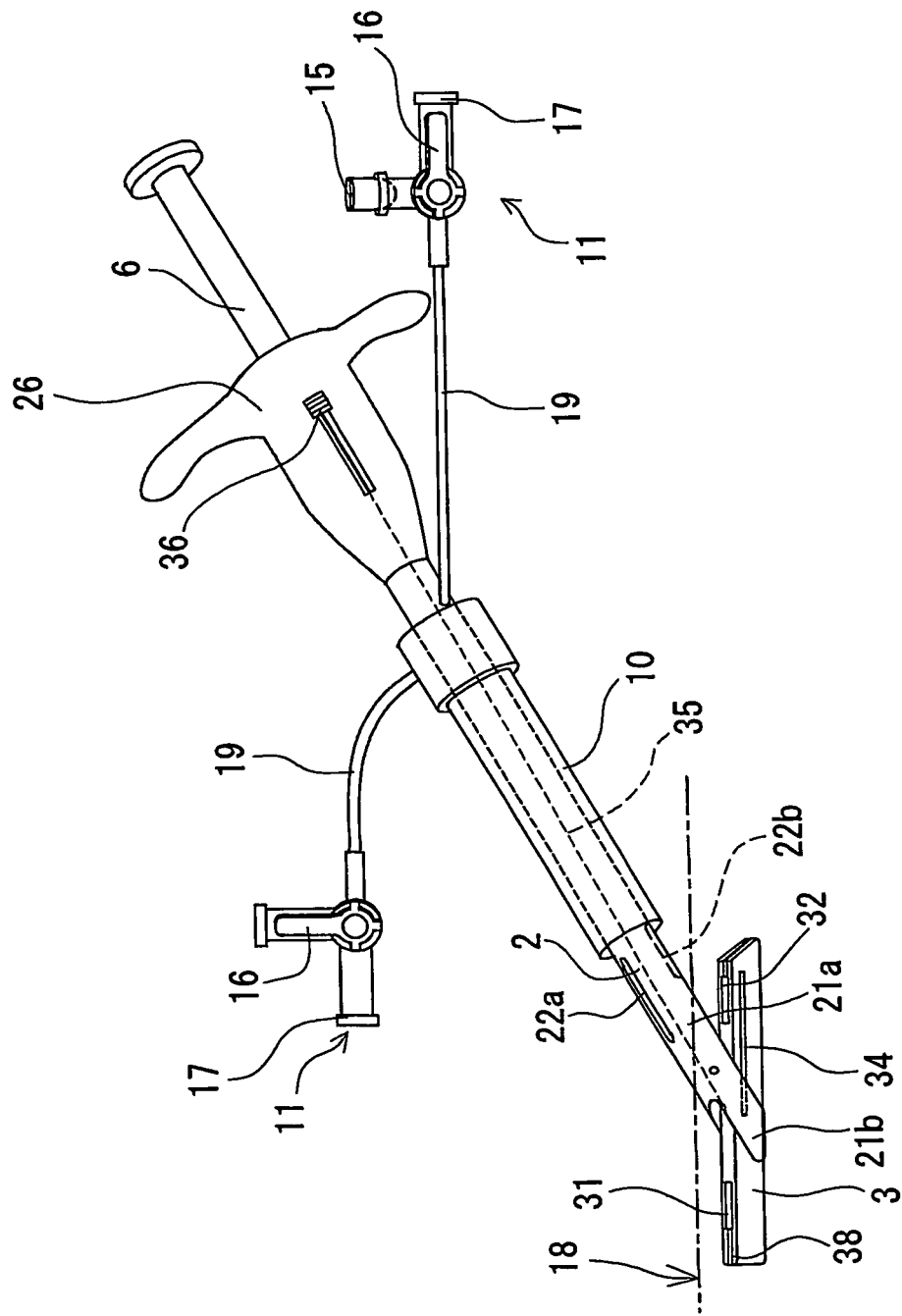
FIG. 9 is an explanatory view for explaining the operation of the organism tissue suturing apparatus of the present invention.

As shown in FIG. 8, when the rotary portion 3 rotates, the shaft 21 of the body part 2 becomes oblique at a predetermined angle with respect to the axis of the rotary portion 3. Thereafter the towing wire operation portion 36 is pulled rearward to move the rotary portion 3 in a direction shown with an arrow of FIG. 8. Thereby a state shown in FIG. 9 is obtained. While the state is kept, the organism tissue suturing apparatus is pulled toward the operator until the pulsation is not confirmed by the pulsation confirmation member 15.

Figure 10:
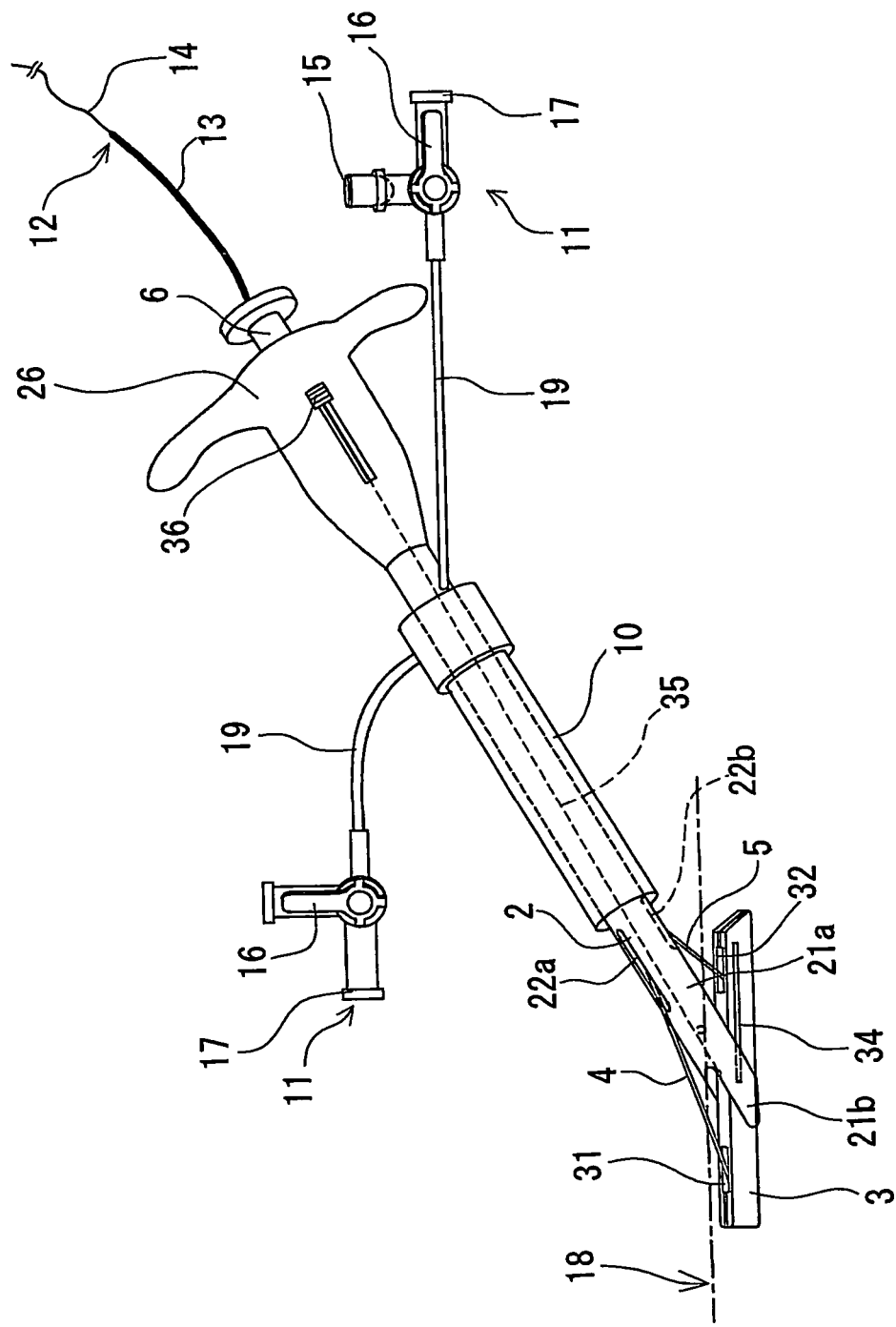
FIG. 10 is an explanatory view for explaining the operation of the organism tissue suturing apparatus of the present invention.
Figure 11:
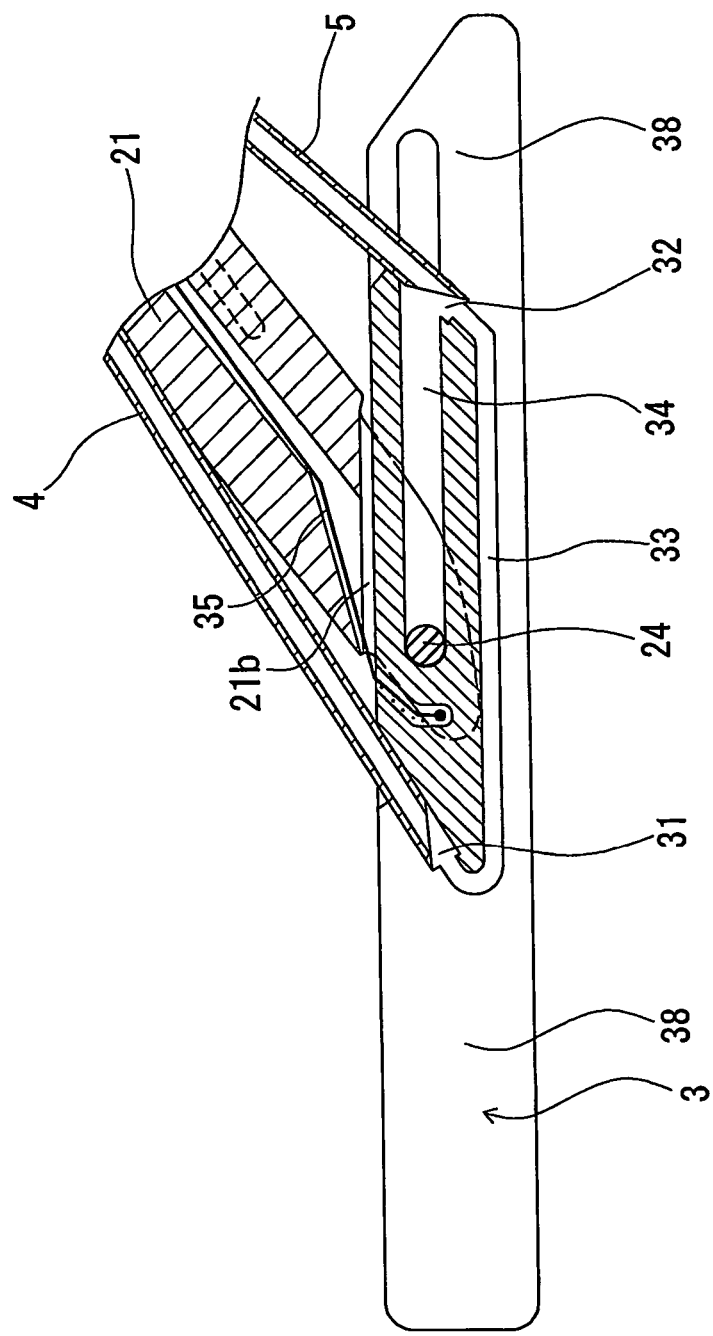
FIG. 11 is an explanatory view for explaining the operation of the organism tissue suturing apparatus of the present invention.

Thereafter as shown in FIG. 10, the needle member operation portion 6 is pressed forward to advance the hollow needle members 4, 5 obliquely from the front-side side surface of the body portion 21a of the body part 2 so that the hollow needle members 4, 5 penetrate through the blood vessel. Thereby as shown in FIG. 11, the front end of the hollow needle member 4 and that of the hollow needle members 5 reach the inside of the needle member receiving portion 31 of the rotary portion 3 and that of the needle member receiving portion 32 thereof respectively. At this time, the needle member operation portion 6 is stopped by a stopper (not shown). Thereby in the state where the needle member receiving portions 31, 32 receive the hollow needle members 4, 5 respectively, in the organism tissue suturing apparatus, the duct for the suturing thread is formed in the range from one opening 7 to the other opening 8 through the inside of the hollow needle member 4, the needle member receiving portion 31 of the rotary portion 3, the connection duct 33, the needle member receiving portion 32, and the inside of the hollow needle member 5.

As shown in FIG. 10, the suturing member 12 is inserted into the organism tissue suturing apparatus from the opening 7, with the guide portion 13 thereof disposed forward. As shown in FIG. 12, the guide portion 13 inserted into the suturing apparatus 1 penetrates into the hollow needle member 4, the needle member receiving portion 31 of the rotary portion 3, the connection duct 33, the needle member receiving portion 32, and the hollow needle member 5. By further inserting the suturing member 12 into the organism tissue suturing apparatus, the front end of the guide portion 13 protrudes from the other opening 8. Then by pulling the front end of the protruded guide portion 13, as shown in FIG. 13, the suturing thread portion 14 reaches the inside of the rotary portion 3. Finally, as shown in FIG. 14, the suturing thread portion 14 penetrates through the rotary portion 3 and into the hollow needle member 5. It is preferable that in the forward movement of the suturing member 12, the guide portion 13 is discharged from the suturing apparatus 1 and only the suturing thread portion 14 is disposed in the duct for the suturing thread formed inside the suturing apparatus 1.

In the organism tissue suturing apparatus, it is possible to perform an operation of piercing the blood vessel wall 18 with the hollow needle members 4, 5 by pressing the operation portion forward in a short stroke so that the hollow needle members 4, 5 disposed a little outward from the blood vessel wall 18 are accommodated respectively in the needle member receiving portions 31, 32 of the rotary portion 3 disposed a little inward from the blood vessel wall 18. Thus the suturing operation can be performed easily. Further the suturing member 12 inserted into the duct for the suturing thread formed inside the organism tissue suturing apparatus 1 from one end thereof is exited from the other end thereof. Therefore from the outside of the patient, it is possible to confirm that the suturing operation is being performed.

Figure 17:
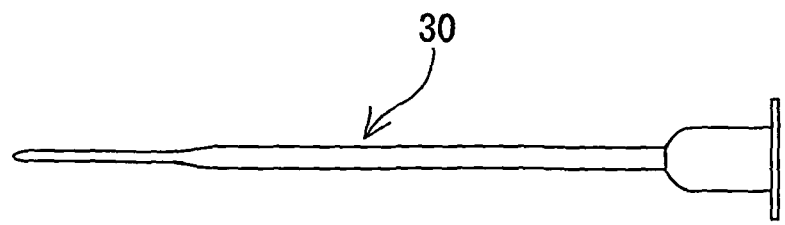
FIG. 17 shows an outlook of a pressing instrument for pressing a suturing thread into an organism after the organism tissue suturing apparatus of the present invention performs a suturing operation.

After the confirmation of the suturing operation, the needle member operation portion 6 is released from the stopper. The needle member operation portion 6 is returned in the first condition by the elastic force of the elastic member 27 or a manual operation. The hollow needle members 4, 5 are accommodated in the body part 2. Then the wire operation portion 36 is pressed forward, and the towing of the rotary portion 3 by means of the towing wire 35 terminates to return the rotary portion 3 to the initial position. Then the suturing apparatus 1 and the cylindrical sheath 10 are pulled out of the puncture site, with both ends of the suturing thread portion 14 being pulled. At this time, the suturing thread portion 14 comes out from the thread pull-out slit 38 of the rotary portion 3. That is, the suturing thread portion 14 exposes from the suturing apparatus 1. Then the suturing thread portion 14 is tied and is advanced to a pierced hole of the blood vessel with a pressing instrument 30, as shown in FIG. 17. After the pressing instrument 30 is removed from the pierced hole of the blood vessel, the suturing thread portion 14 is cut at a position close to the tied portion. Thereby the suturing operation terminates.

Figure 18:
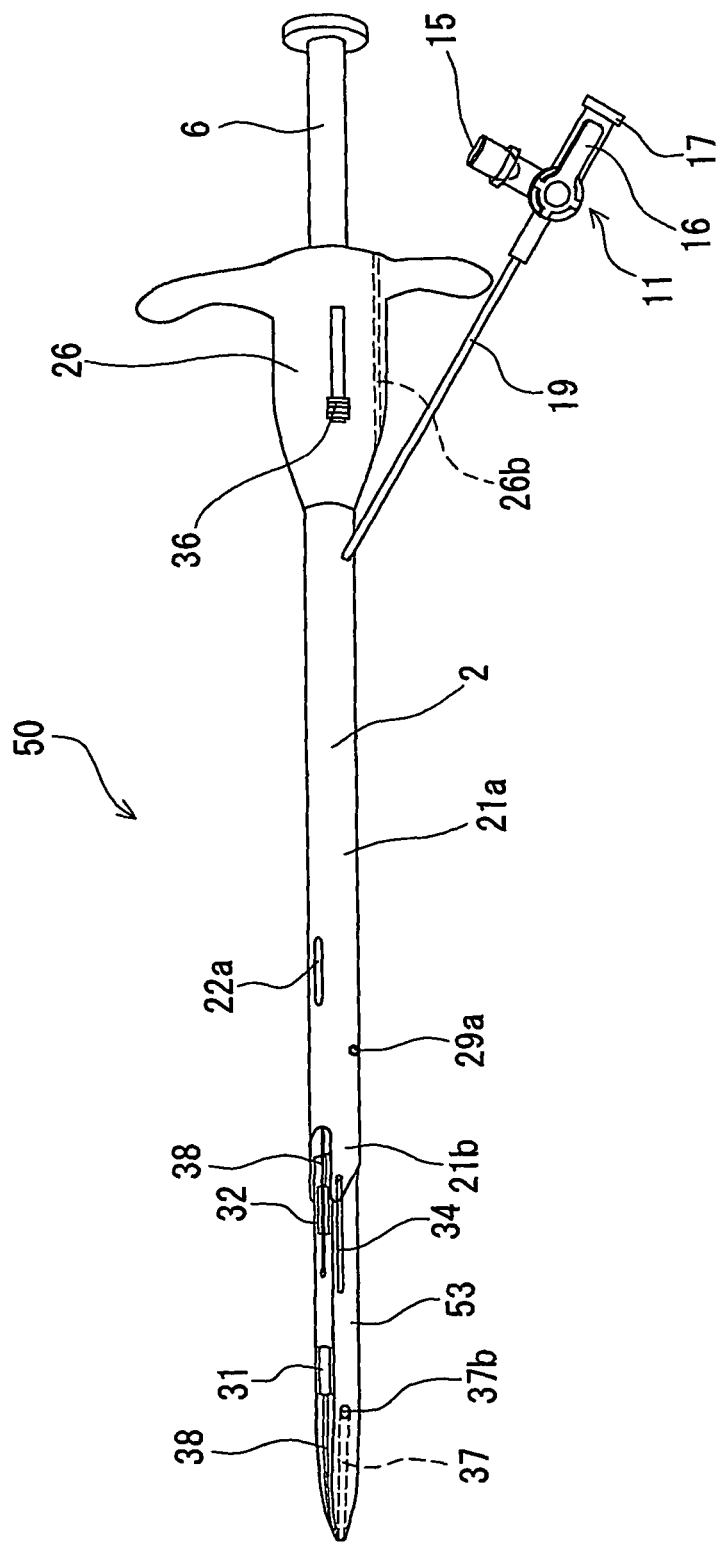
FIG. 18 shows an outlook of an organism tissue suturing apparatus according to another embodiment of the present invention.
Figure 19:
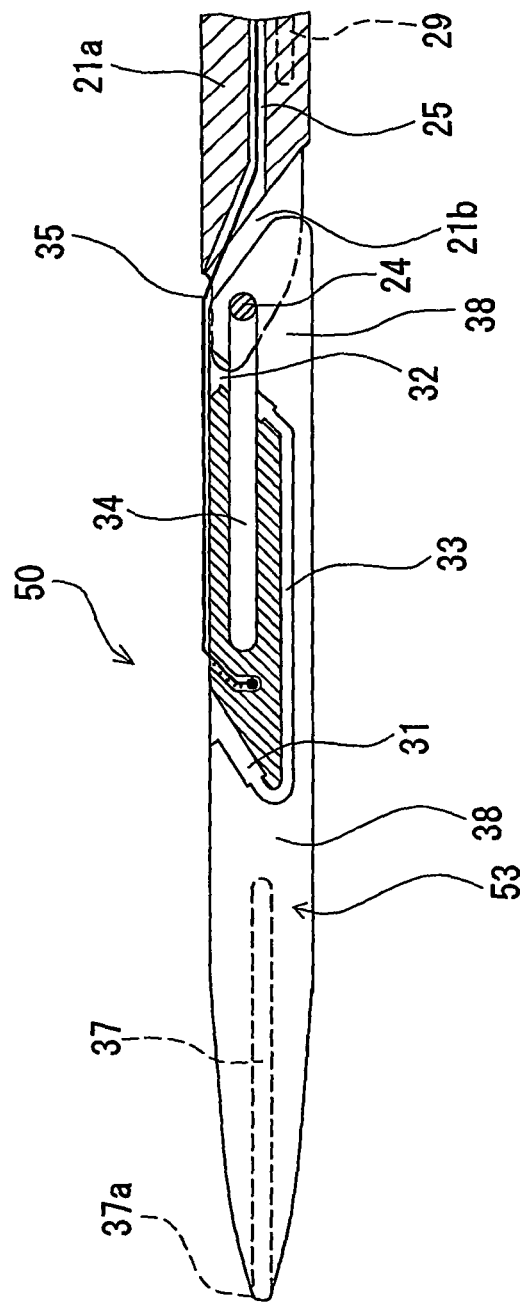
FIG. 19 is an enlarged sectional view of a front side of the organism tissue suturing apparatus shown in FIG. 18.
Figure 20:
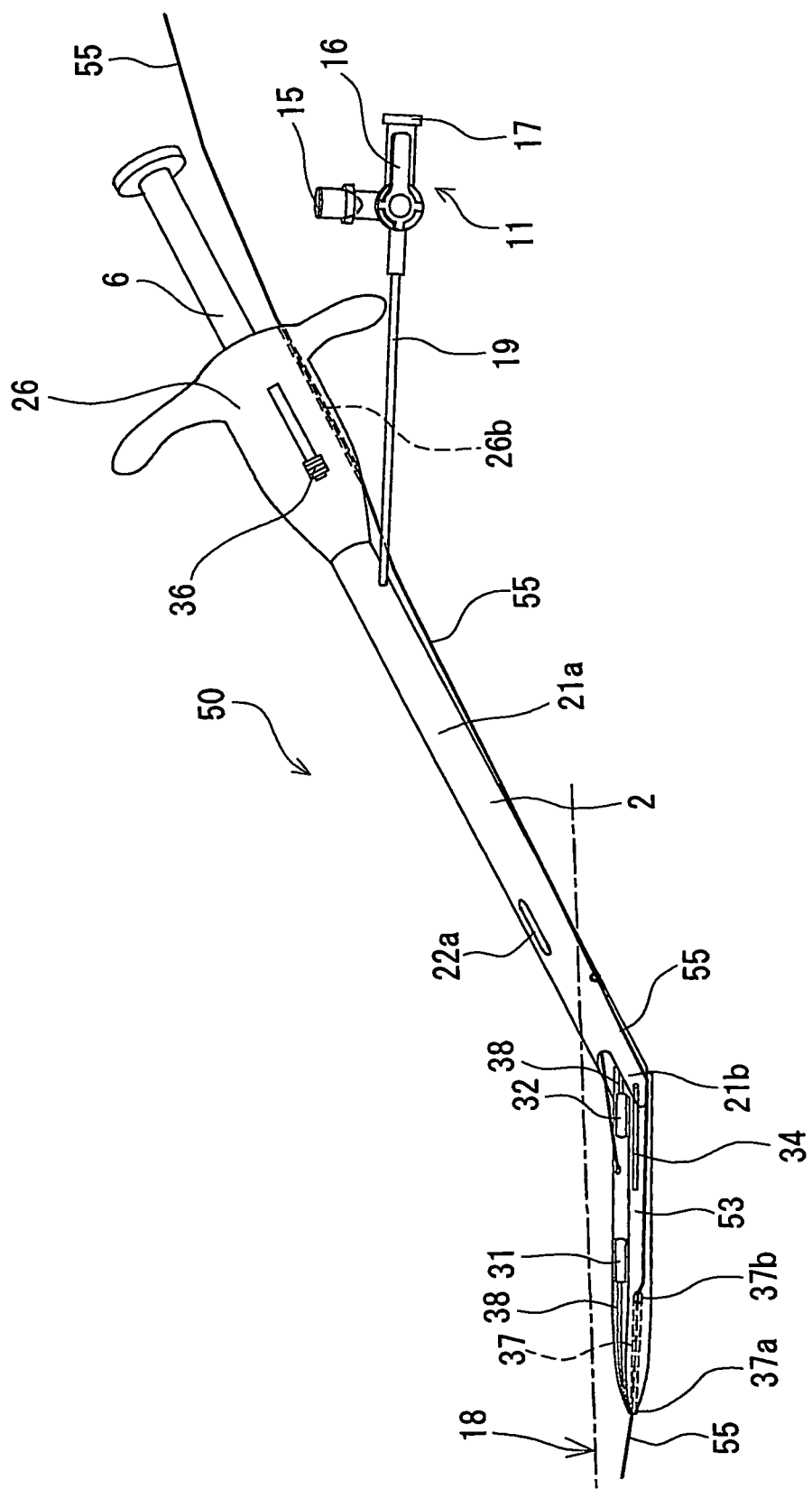
FIG. 20 is an explanatory view for explaining the operation of the organism tissue suturing apparatus shown in FIG. 18.

An organism tissue suturing apparatus 50 of an embodiment shown in FIGS. 18 through 20 is described below. The organism tissue suturing apparatus 50 of this embodiment is different from the above-described organism tissue suturing apparatus 1 in that a rotary portion 53 of the former has a guide wire insertion lumen 37 disposed in the range from its front side to its side surface and that the shaft hub 26 of the former has a guide wire insertion duct 26b. The other constructions of the organism tissue suturing apparatus 50 are the same as those of the organism tissue suturing apparatus 1. Thus description of parts of the organism tissue suturing apparatus 50 common to those of the organism tissue suturing apparatus 1 are omitted herein. The organism tissue suturing apparatus 50 can be used without using the sheath 10.

As shown in FIGS. 18 and 19, the rotary portion 53 has the guide wire insertion lumen 37 having an opening 37a at its front end and a side opening 37b at its rear end. The lumen 37 terminates at a position forward from the needle member receiving portion 31. It is preferable that the axial length of the guide wire insertion lumen 37 is 1.0 to 4.0 mm. The sectional area of the front side of the rotary portion 53 becomes gradually smaller toward its front end. It is preferable that the rotary portion 53 has a width of 0.5 to 9.0 mm, a height of 0.8 to 10.0 mm, and a length of 2.0 to 6.0 mm.

As shown in FIGS. 18 and 20, the shaft hub 26 has the guide wire insertion duct 26b. One end of the guide wire insertion duct 26b is open at the front end of the shaft hub 26 and the other end thereof is open at the rear end of the shaft hub 26. By providing the shaft hub with the guide wire insertion duct, it is possible to operate the guide wire, together with the organism tissue suturing apparatus and perform a suturing operation easily.

The construction of the organism tissue suturing apparatus 50 is the same as that of the above-described organism tissue suturing apparatus 1 except that the organism tissue suturing apparatus 50 has the guide wire insertion lumen 37 and the guide wire insertion duct 26b.

The operation of the organism tissue suturing apparatus 50 of the embodiment is described below with reference to FIG. 20.

As in the case of the organism tissue suturing apparatus 1, the three-way cock 11 is operated to fill a liquid into the liquid-filling lumen 29. Thereafter the operation portion 16 is switched to communicate the pulsation confirmation member installing port and the liquid-filling lumen 29 with each other.

Thereafter a guide wire 55 is inserted into the introducer sheath (not shown), for use in treatment or diagnosis, whose front end has reached the tissue of the organism through the hole formed in the tissue membrane of the organism. Thereafter the introducer sheath 10 is removed from the tissue of the organism. The guide wire 55 is inserted into the guide wire insertion lumen 37 from an opening 37a thereof disposed at the front end of the organism tissue suturing apparatus 50 and extended rearward from the side opening 37b. Thereafter the guide wire 55 is penetrated through the guide wire insertion duct 26b formed in the shaft hub 26. Then the organism tissue suturing apparatus 50 is inserted into the organism along the guide wire 55. Thereafter the organism tissue suturing apparatus 50 is inserted into a blood vessel through a puncture site until pulsation of the interface between the liquid filled in the pulsation confirmation member (in other words, pulsation indicator cap) 15 and air appears, in other words, until a front-end opening 29a of the lumen 29 of the body part reaches the inside of the blood vessel. FIG. 20 shows this state. The broken line 18 of FIG. 20 shows a blood vessel wall which is the tissue membrane of the organism.

As shown in FIG. 20, when the rotary portion 53 rotates, the shaft 21 of the body part 2 becomes oblique at a predetermined angle with respect to the axis of the rotary portion 53. The organism tissue suturing apparatus is inserted further into the puncture site by about 30 mm from the position at which the pulsation is confirmed by the pulsation confirmation member. Thereafter the towing wire operation portion 36 is pulled rearward to move the rotary portion 53 rearward. While the state is kept, the organism tissue suturing apparatus is pulled toward the operator until the pulsation can not be confirmed by the pulsation confirmation member 15.

Thereafter the needle member operation portion 6 is pressed forward to advance the hollow needle members 4, 5 obliquely from the front-side side surface of the body portion 21a of the body part 2 so that the hollow needle members 4, 5 penetrate through the blood vessel. Thereby similarly to the operation described with reference to FIG. 11, the front end portion of the hollow needle member 4 and that of the hollow needle members 5 reach the inside of the needle member receiving portion 31 of the rotary portion 3 and that of the needle member receiving portion 32 thereof respectively. In this case, the needle member operation portion 6 may be fixed by an unshown stopper. Thereby in the state where the needle member receiving portions 31, 32 receive the hollow needle members 4, 5 respectively, in the organism tissue suturing apparatus 50, the duct for the suturing thread is formed in the range from one opening 7 to the other opening 8 through the inside of the hollow needle member 4, the needle member receiving portion 31 of the rotary portion 3, the connection duct 33, the needle member receiving portion 32, and the inside of the hollow needle member 5.

As in the case of the organism tissue suturing apparatus 1, the suturing member 12 is inserted into the organism tissue suturing apparatus 50 in such a way that the suturing thread portion 14 of the suturing member 12 penetrates through the duct for the suturing thread formed in the organism tissue suturing apparatus 50, as shown in FIG. 14.

After the confirmation of the suturing operation, the needle member operation portion 6 is released from the stopper. The needle member operation portion 6 is returned in the first condition by the elastic force of the elastic member 27 or a manual operation. The hollow needle members 4, 5 are accommodated in the body part 2. Then the wire operation portion 36 is pressed forward and the towing 35 of the rotary portion 53 by means of the towing wire 35 terminates to return the rotary portion 53 to the initial position.

Then the organism tissue suturing apparatus 50 is pulled out of the puncture site, with the guide wire 55 remaining in the lumen 37 and with both ends of the suturing thread exposed to the outside from the organism tissue suturing apparatus 50 pulled with the operator's hand. At this time, the suturing thread portion 14 separates from the thread pull-out slit 38 of the rotary portion 53. That is, the suturing thread portion 14 separates from the rotary portion 53 and remains in the blood vessel.

Then the suturing thread portion 14 is tied and is advanced to a pierced hole of the blood vessel with the pressing instrument 30, as shown in FIG. 17. Then the pressing instrument 30 is removed from the pierced hole of the blood vessel. If no bleeding is visually observed, the guide wire 55 is removed from the lumen. After the suturing thread portion 14 is tied further to secure stopping of bleeding, the suturing thread portion 14 is cut at a position close to the tied portion. Thereby the suturing operation terminates.

Figure 21:
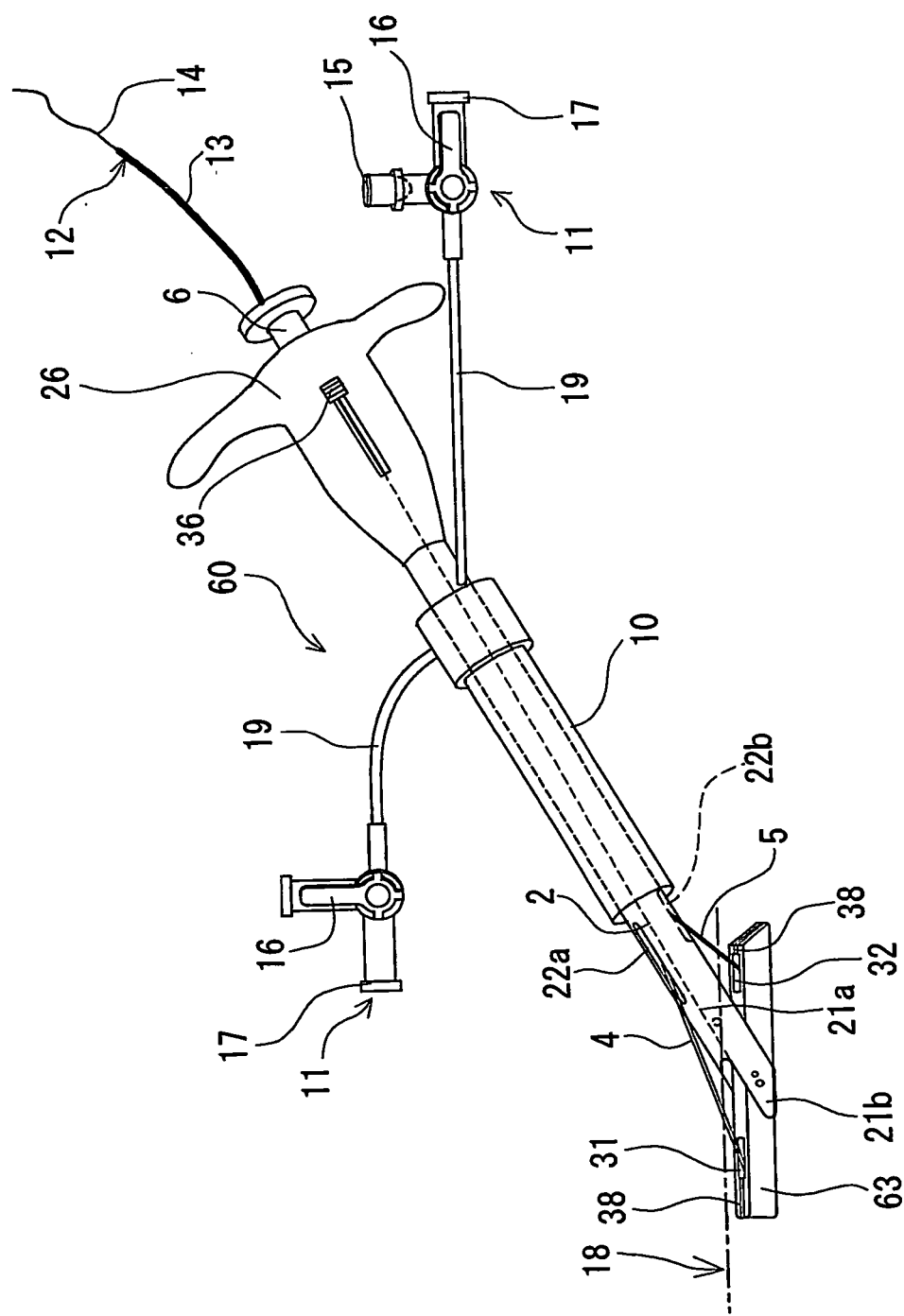
FIG. 21 is an explanatory view for explaining the operation of an organism tissue suturing apparatus according to another embodiment of the present invention.
Figure 22:
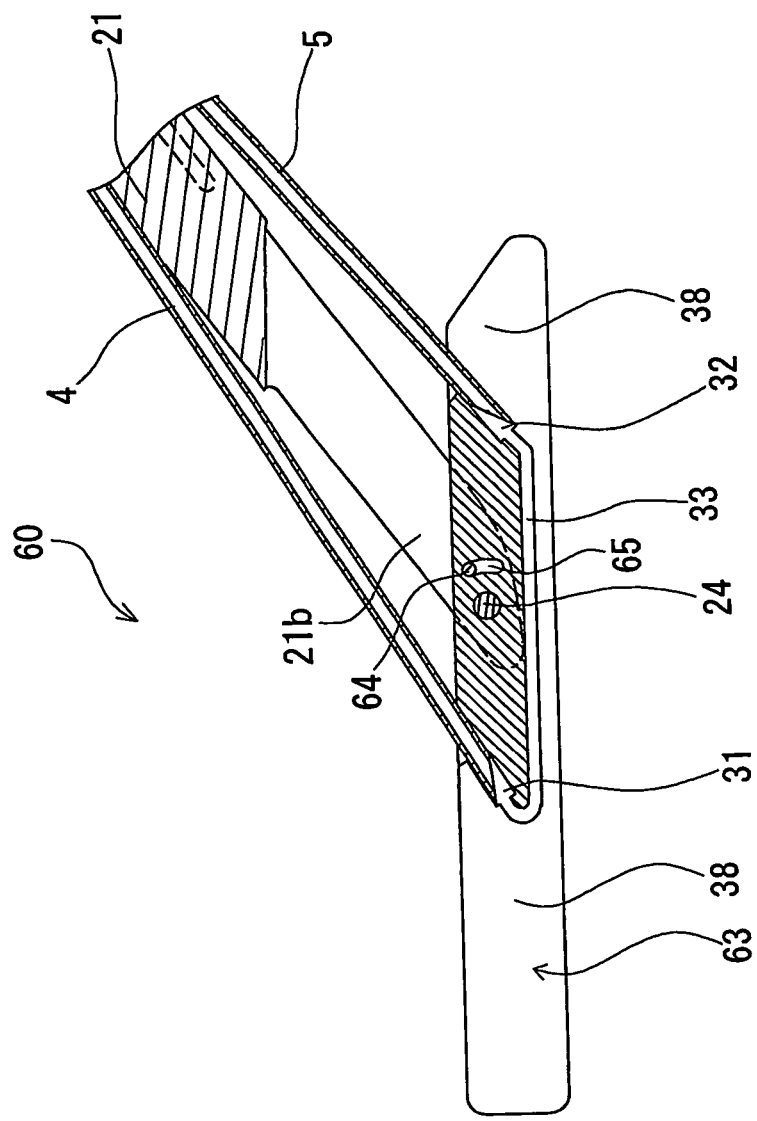
FIG. 22 is an explanatory view for explaining the operation of the organism tissue suturing apparatus of the present invention shown in FIG. 21.

An organism tissue suturing apparatus 60 of an embodiment shown in FIGS. 21 and 22 is described below. The organism tissue suturing apparatus 60 of this embodiment is different from the above-described organism tissue suturing apparatus 1 in the mode of supporting the rotary portion by means of the body part 2. The other constructions of the organism tissue suturing apparatus 60 are the same as those of the organism tissue suturing apparatus 1. Thus description of parts of the organism tissue suturing apparatus 60 common to those of the organism tissue suturing apparatus 1 are omitted herein.

The slidable rotary portion of the organism tissue suturing apparatus 1 is preferable. However, the rotary portion of the organism tissue suturing apparatus 60, shown in FIGS. 21 and 22, that does not slide but is rotatably supported by the body part can be adopted. In the organism tissue suturing apparatus 60 of the embodiment, the rotary portion 63 has a rotation angle restriction function permitting the rotation thereof between a state in which the rotary portion 63 is on an approximate extension line of the axis of the body part 2 and a predetermined angle less than 90 degrees. It is preferable that the rotation angle restriction function permits the rotary portion to pivot at a predetermined angle less than 60 degrees. The rotation angle restriction function allows the hollow needle members 4, 5 to be received in the rotary portion 63 securely. As shown in FIG. 22, the rear side of the rotary portion 63 is disposed between the front ends 21b and 21b of the shaft. The rotary portion 63 is supported by a shaft 24 fixed to the front end 21b. The rotary portion 63 has a loose opening 65 formed on the side surface thereof. The loose opening 65 slidably accommodates pins 64 provided on an inner surface of each of the opposed bifurcated front ends 21b of the shaft. The loose opening 65 has the shape of a circular arc having an axis 24 and a predetermined length. Thus the rotary portion 63 is pivotal within an angle formed on the loose opening 65 with respect to the axis 24. It is preferable that the angle of the loose opening 65 with respect to the axis 24 is 10 to 90 degrees. As the rotary portion 63, it is possible to form the loose opening on each of the side surfaces of the bifurcated front ends 21b of the shaft and form a pin slidable in the loose opening 65. It is suitable that the rotary portion 63 has a width of 0.5 to 9.0 mm, a height of 0.8 to 10.0 mm, and a length of 2.0 to 6.0 mm.

The operation of the organism tissue suturing apparatus 60 is similar to that of the organism tissue suturing apparatus 1 except that the towing wire operation portion is not operated.

Figure 23:
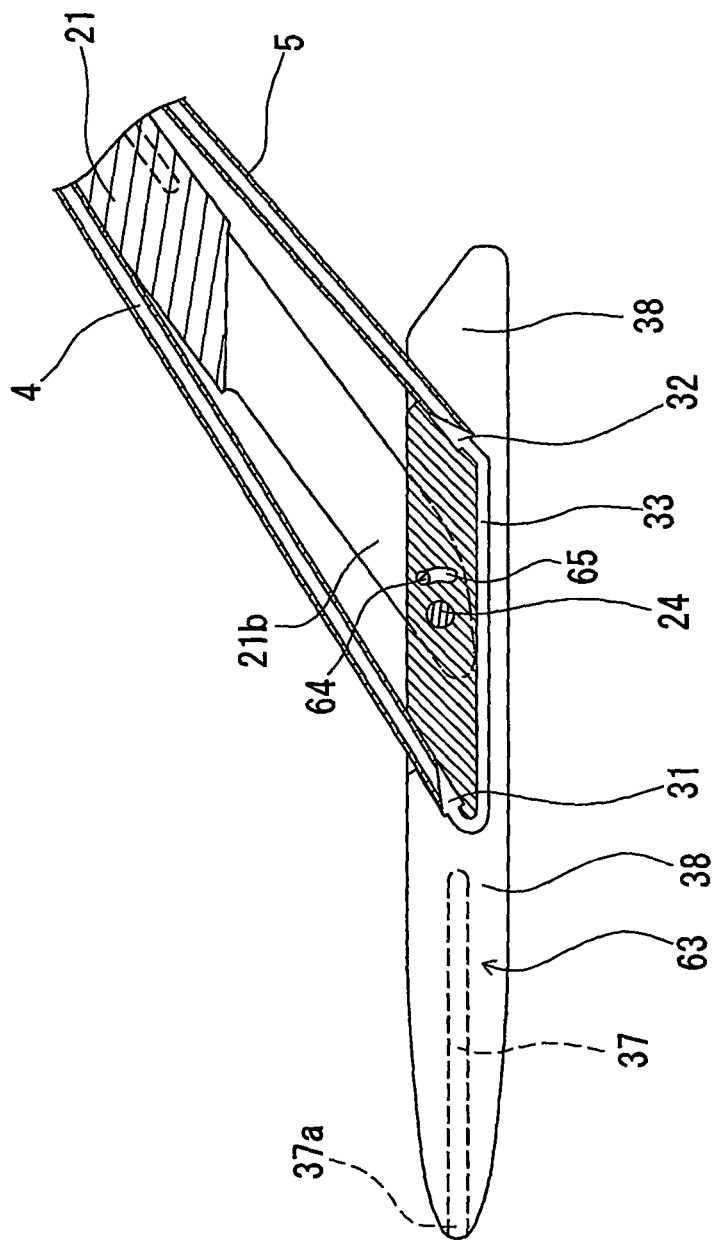
FIG. 23 is an explanatory view for explaining the operation of the organism tissue suturing apparatus of the present invention shown in FIG. 21.

Similarly to the suturing apparatus 50, the rotary portion 63 of the organism tissue suturing apparatus 60 may have the guide wire insertion lumen 37, as shown in FIG. 23. In this case, it is preferable that the shaft hub has a guide wire insertion duct The guide wire insertion lumen 37 has an opening 37a at its front end and a side opening 37b at its rear end. The lumen 37 terminates at a position forward from the needle member receiving portion 31. It is preferable that the axial length of the guide wire insertion lumen 37 is 1.0 to 4.0 mm. The sectional area of the front side portion of the rotary portion 63 becomes gradually smaller toward its front end. It is preferable that the rotary portion 63 has a width of 0.5 to 9.0 mm, a height of 0.8 to 10.0 mm, and a length of 2.0 to 6.0 mm.

It is preferable that the shaft hub has the guide wire insertion duct shown in FIGS. 18 and 20. One end of the guide wire insertion duct 26b is open at the front end of the shaft hub 26 and the other end thereof is open at the rear end of the shaft hub 26. By providing the shaft hub with the guide wire insertion duct, it is possible to operate the guide wire, together with the organism tissue suturing apparatus and perform a suturing operation easily.

The operation of the organism tissue suturing apparatus 60 is similar to that of the organism tissue suturing apparatus 50 except that the towing wire operation portion is not operated.

Figure 24:
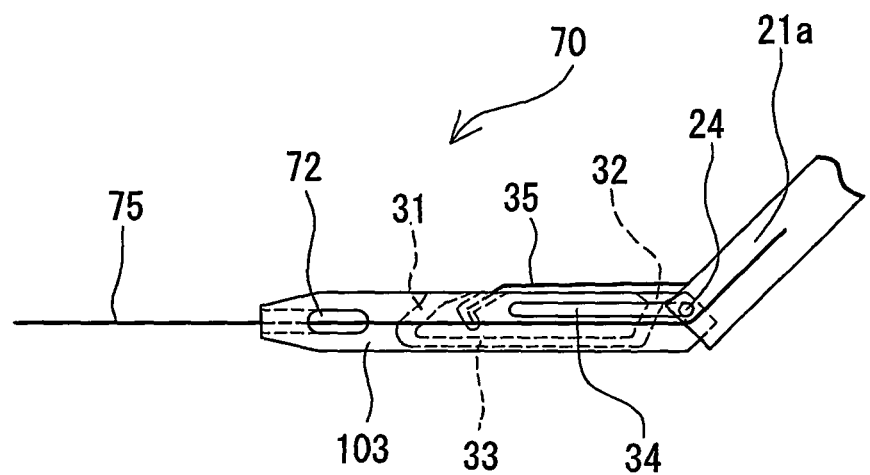
FIG. 24 is an explanatory view for explaining an organism tissue suturing apparatus according to another embodiment of the present invention.

The above-described organism tissue suturing apparatus 1 may have an introduction wire 75 as in the case of an organism tissue suturing apparatus 70 shown in FIG. 24. The introduction wire 75 extends inside a lumen 72 formed inside a rotary portion 73. The front end of the introduction wire 75 protrudes from the rotary portion. The introduction wire 75 is not fixed to the rotary portion 73 but the rear end thereof is fixed to the body part. Because the introduction wire 75 is not fixed to the rotary portion 73, the rotation and slide of the rotary portion 73 are not inhibited.

More specifically, the rotary portion 73 has the lumen 72 whose one end is open at its front end and whose other end is open at a side surface in the vicinity of the center of the rotary portion 73. The introduction wire 75 penetrates through the lumen 72 formed inside the rotary portion 73. The front side of the introduction wire 75 protrudes from the front-end opening of the rotary portion 73, whereas the other side of the introduction wire 75 protrudes from the opening formed on the side surface of the rotary portion 73 and is fixed to the front end 21a of the body portion of the shaft A guide wire-fixing groove or a guide wire-fixing lumen is formed at the front side of the body portion of the shaft The rear side of the guide wire is fixedly accommodated in the guide wire-fixing groove or the guide wire-fixing lumen. The introduction wire 75 and the front end 21a of the body portion of the shaft are fixed to each other by applying an adhesive agent, thermal fusing or mechanical fitting to the guide wire-fixing groove or to the guide wire-fixing lumen. The proximal side of the introduction wire 75 is fixed with the same method in the hub.

It is preferable that the axial length of the guide wire insertion lumen 72 is 1.0 to 4.0 mm. The sectional area of the front side of the rotary portion 73 becomes gradually smaller toward its front end. It is preferable that the rotary portion 73 has a width of 0.5 to 9.0 mm, a height of 0.8 to 10.0 mm, and a length of 2.0 to 6.0 mm.

It is preferable that the length of the introduction wire 75 extending forward from the rotary portion 73 is 10 to 500 mm.

It is preferable that the introduction wire 75 has a length of 10 to 600 mm and an outer diameter of 1.0 to 10.0 mm. It is possible to use the following materials for the introduction wire 75: Metals such as stainless steel, Ni—Ti alloy, Cu—Zn alloy, Ni—Al alloy, tungsten, tungsten alloy, titanium, titanium alloy, cobalt alloy, tantalum; and macromolecular materials including polyolefin such as polypropylene, polyethylene, and the like, olefin elastomer (for example, polyethylene elastomer, polypropylene elastomer), polyester such as polyethylene terephthalate, flexible polyvinyl chloride, polyurethane, urethane elastomer, polyamide, amide elastomer (for example, polyamide elastomer), polytetrafluoroethylene, fluorocarbon resin elastomer, polyimide, ethylene-polyvinyl chloride copolymer, and silicone rubber. These macromolecular materials are applied to the surface of a wire consisting of any of the above-described metals. Silicon or hydrophilic resins may be applied to the surface of the wire to increase the lubricity of its surface.

Figure 25:
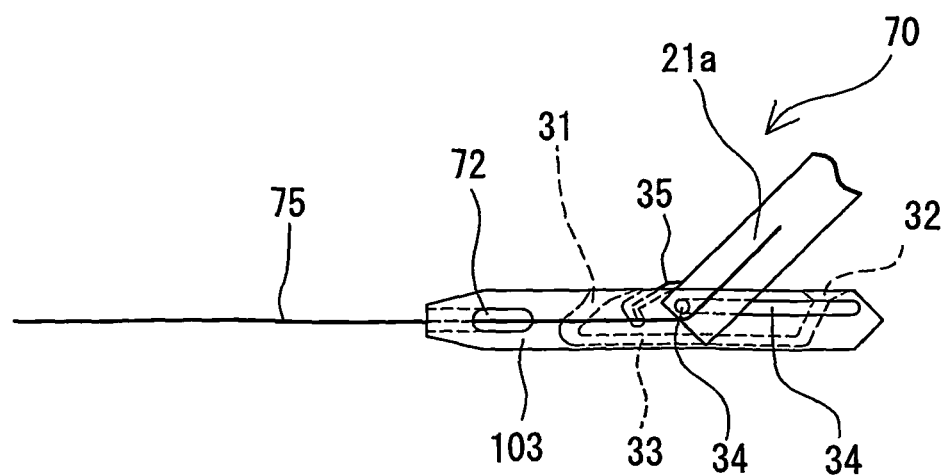
FIG. 25 is an explanatory view for explaining the operation of the organism tissue suturing apparatus of the present invention shown in FIG. 24.

The operation of the organism tissue suturing apparatus 70 of this embodiment is described below. The fundamental operation of the organism tissue suturing apparatus 70 is the same as that of the organism tissue suturing apparatus 1. The organism tissue suturing apparatus 70 can be inserted easily by the guide of the introduction wire 75. Thus the organism tissue suturing apparatus 70 is safe for the organism. As shown in FIG. 25, when the rotary portion-towing wire 35 is pulled, only the rotary portion 73 moves toward the rear side but the introduction wire 75 does not move. Therefore the rotary portion 73 is capable of sliding smoothly. Let it be supposed that only the front end of the wire 75 remains in the blood vessel in removing the apparatus 70 from the organism after an operation of piercing the blood vessel wall with the needle member and inserting the thread into the pierced portion. In this case, a first thread and a second thread are tied with each other on the skin, and the knot is moved to the pierced hole formed in penetration through the blood vessel wall with the pressing instrument 30, with the front end of the wire 75 remaining in the blood vessel. In the case where the hole has been sutured after confirming that bleeding has not occurred, the entire apparatus 70 is removed from the organism. Thereafter the knot is pressed a little. Thereby the suturing operation is completed. The operator feels assured in the suturing operation because the operator can confirm that the hole has been sutured securely, with the front end of the wire 75 remaining in the blood vessel. This is because if the suturing is incomplete and bleeding has occurred, the suturing operation can be performed again by inserting the apparatus into the organism.

In the organism tissue suturing apparatus of this embodiment, it is possible to perform an operation of piercing the tissue membrane of the organism with the needle by pressing the needle member operation portion forward in a short stroke so that the needle disposed a little outward from the tissue membrane of the organism are accommodated in the accommodation portion of the rotary portion disposed a little inward from the tissue membrane of the organism. Thus the suturing operation can be performed easily. Further by inserting the suturing thread into the duct for the suturing thread, it is possible to confirm the penetration of the suturing therethrough. Therefore it is possible to confirm that the operation of suturing the hole formed in the tissue membrane of the organism is being performed.

By providing the organism tissue suturing apparatus with an urging member for urging the needle member operation portion rearward and a stopper for stopping the needle member operation portion at the pushed condition, it is unnecessary to perform an operation of pulling back the needle member operation portion after the needle member operation portion is operated and the stopper is released. Thus a suturing operation can be performed easily.

The organism tissue suturing apparatus has a liquid-filling lumen, extending inside the body part, whose one end can be inserted into the tissue of the organism and is open at a position in the vicinity of the front end side of the lumen and whose other end is open at the rear side of the body part; a three-way cock connected to the lumen; a pulsation confirmation member mounted on one port of the three-way cock; and a liquid-filling port formed on another port of the three-way cock. The three-way cock has an operation portion for selectively communicating the lumen with one port thereof and another port thereof. Thereby without flowing blood into the apparatus directly, it is possible to confirm the arrival of the body part in the inside the blood vessel.

The body part 2 has a supporting pin for rotatably supporting the rotary portion. The rotary portion has an opening on its side surface. The opening is axially long to allow sliding of the supporting pin. The organism tissue suturing apparatus 70 has a towing wire which extends inside the body part 2, with one end thereof fixed to the rotary portion. Thereby it is possible for the rotary portion to slide on the front end of the body part and reduce the distance between the front end of the hollow needle member and the rotary portion during a suturing work. Thereby a stroke in a suturing work can be shortened.

The organism tissue suturing apparatus of the above-described embodiment may have a projectable portion formed at a position of a body part which can be inserted into a blood vessel or a body cavity from a penetrated hole formed subcutaneously in a tissue membrane of an organism in such a way that the projectable portion has a projection state of projecting from the body part, when the projectable portion is disposed in the blood vessel or the body cavity and a non-projection state of not projecting from the body part until the projectable portion reaches the blood vessel or the body cavity; and a position confirmation mechanism including a display portion, formed in a portion of the organism tissue suturing apparatus which is not inserted into the organism, for discriminating the projection state and the non-projection state of the projectable portion from each other.

Figure 26:
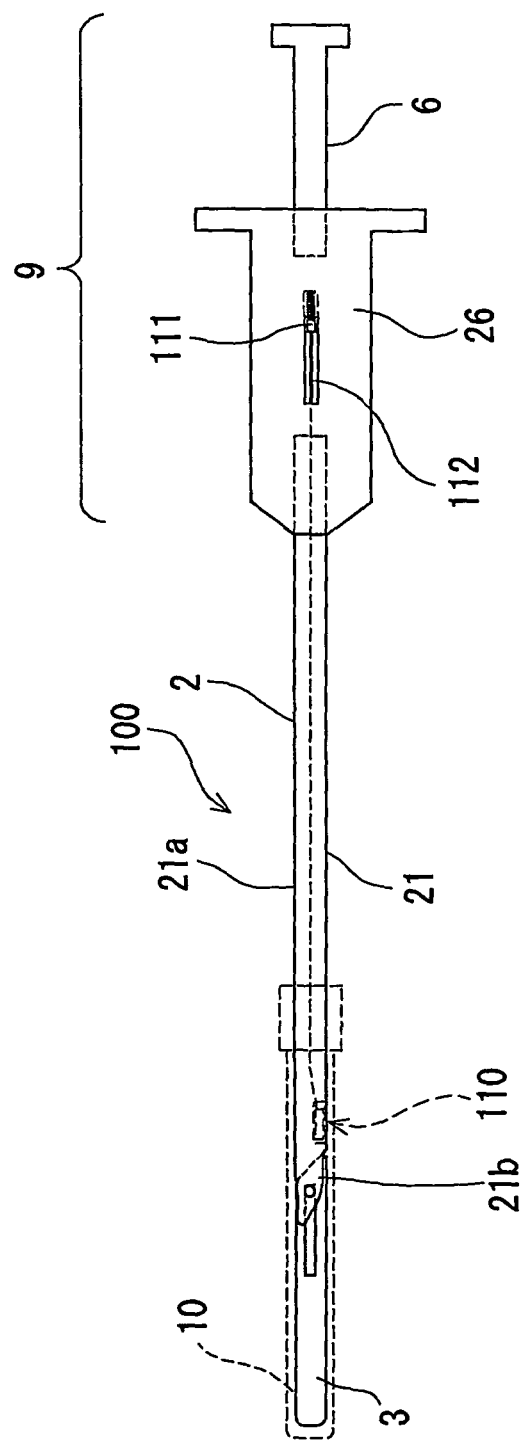
FIG. 26 shows an outlook of an organism tissue suturing apparatus according to another embodiment of the present invention.
Figure 27:
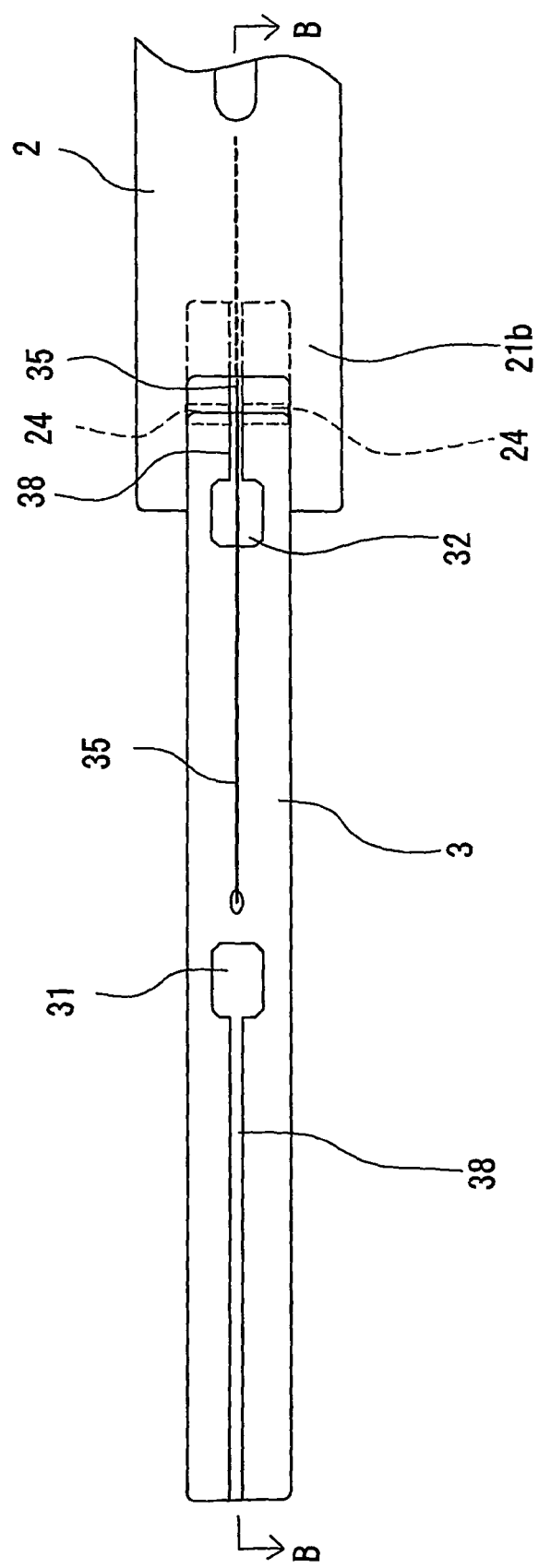
FIG. 27 is a partly broken-away enlarged plan view showing a front side of the organism tissue suturing apparatus shown in FIG. 26.
Figure 28:
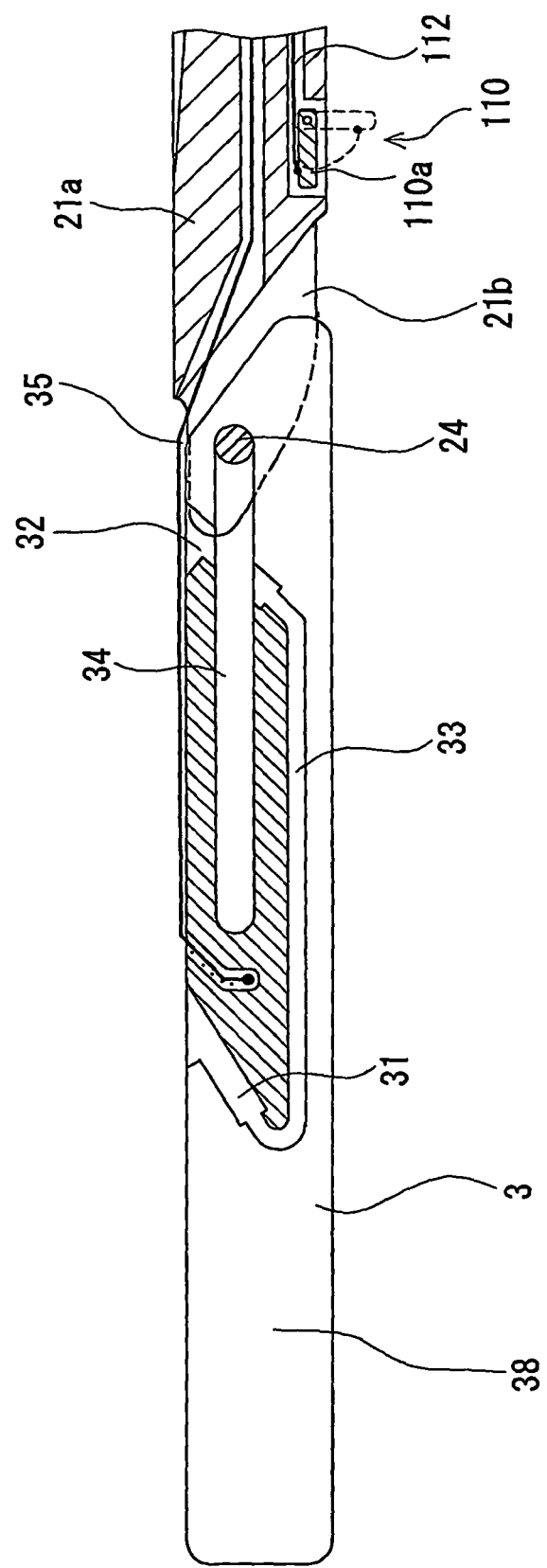
FIG. 28 is a sectional view taken along a line B-B of FIG. 27.
Figure 29:
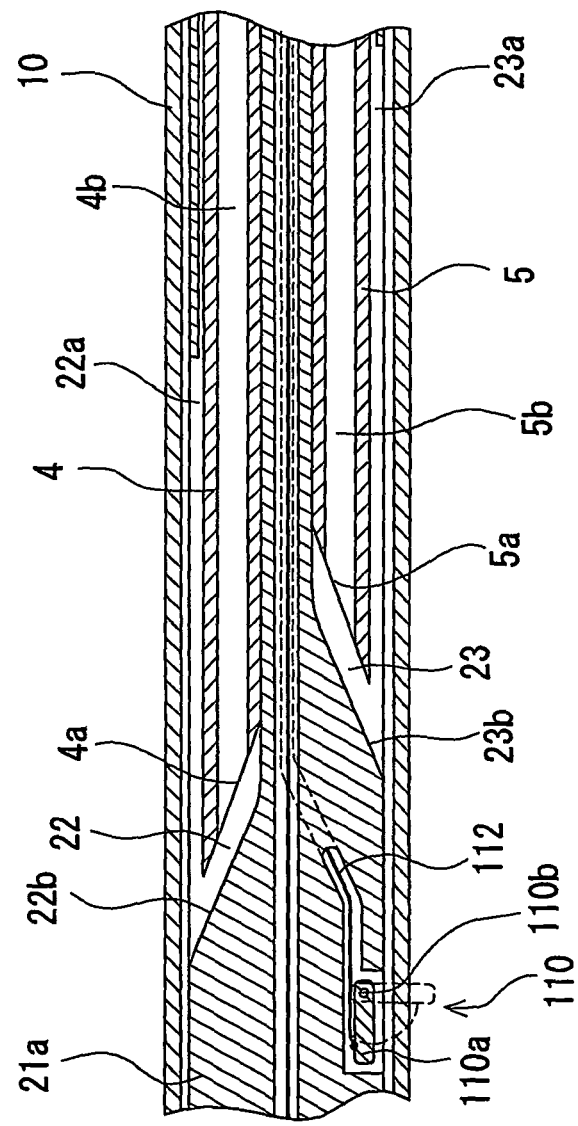
FIG. 29 is an enlarged sectional view showing the vicinity of a front side of a hollow needle member of a body part of the organism tissue suturing apparatus shown in FIG. 26.
Figure 30:
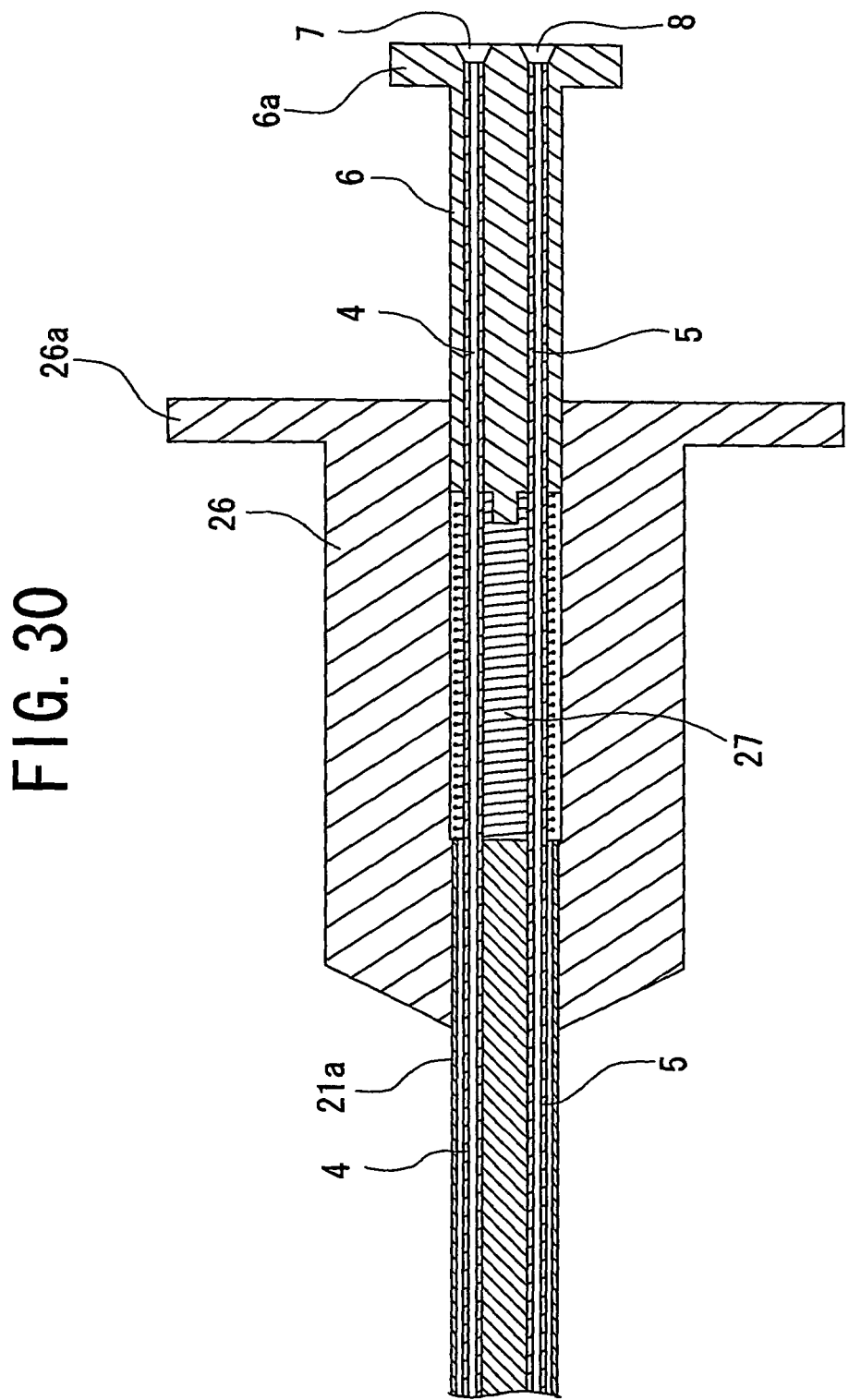
FIG. 30 is an enlarged sectional view showing a rear side of the organism tissue suturing apparatus shown in FIG. 26.
Figure 31:
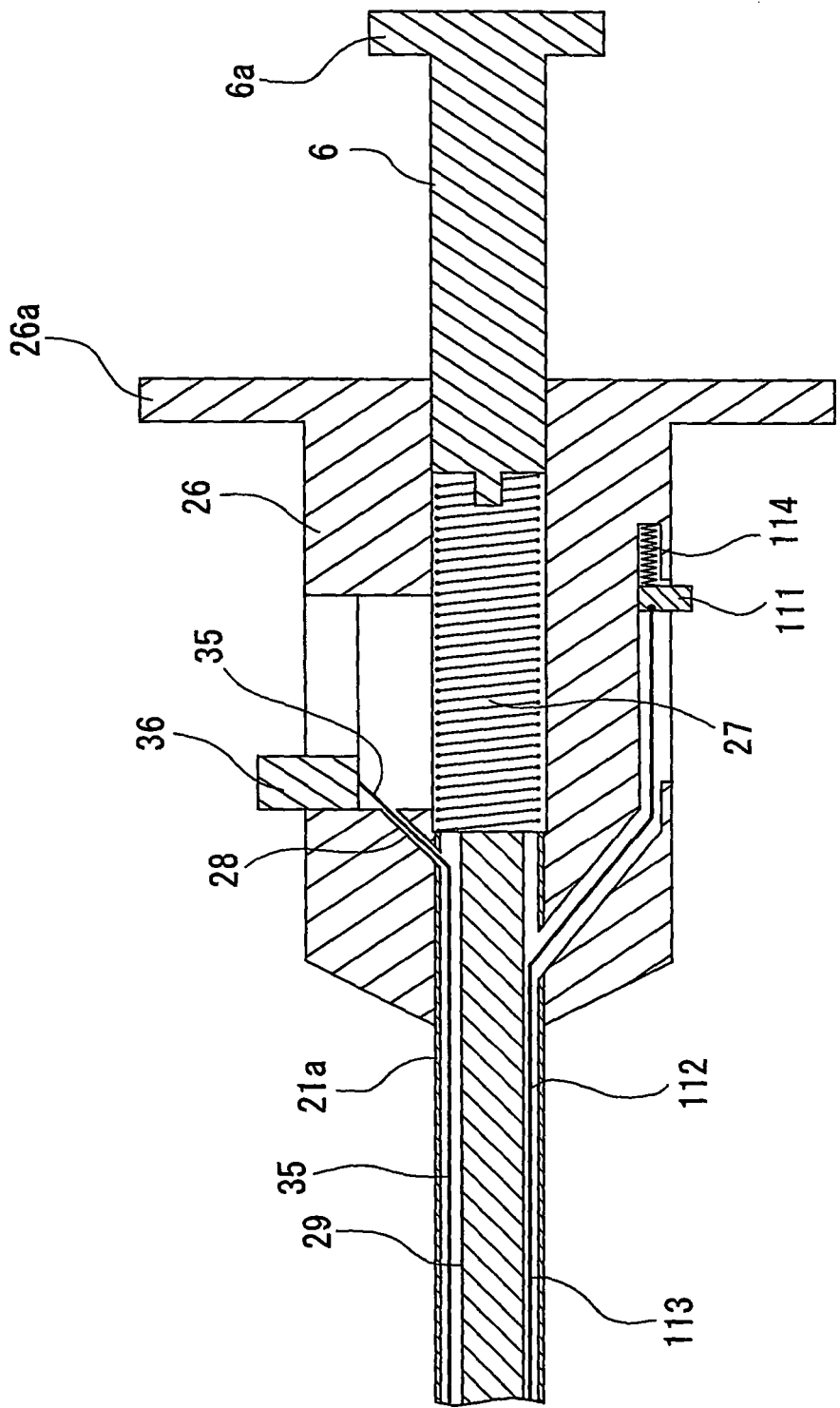
FIG. 31 is an enlarged sectional view showing the rear side of the organism tissue suturing apparatus cut at an angle different by 90 degrees from an angle of FIG. 30.

FIG. 26 shows an outlook of an organism tissue suturing apparatus according to another embodiment of the present invention. FIG. 27 is a partly broken-away enlarged plan view showing a front side of the organism tissue suturing apparatus shown in FIG. 26. FIG. 28 is a sectional view taken along a line B-B of FIG. 27. FIG. 29 is an enlarged sectional view showing the vicinity of a front side of a hollow needle member of a body part of the organism tissue suturing apparatus shown in FIG. 26. FIG. 30 is an enlarged sectional view showing a rear side of the organism tissue suturing apparatus shown in FIG. 26. FIG. 31 is an enlarged sectional view showing the rear side of the organism tissue suturing apparatus cut at an angle different by 90 degrees from an angle of FIG. 30.

As shown in FIGS. 28 and 29, the organism tissue suturing apparatus 100 has a projectable portion 110, a display portion 111, and a member for the projectable portion 110. The content of the projectable portion 100, the display portion 111, and the member for the projectable portion 110 are similar to those of an organism tissue suturing apparatus 200 which will be described later. Thus the projectable portion 110, the display portion 111, and the member for the projectable portion 110 will be described later. The projectable portion 100 may be a projectable portion 180, shown in FIG. 42, which will be described later. It is preferable that similarly to the organism tissue suturing apparatus 200 which will be described later, the organism tissue suturing apparatus 100 has a non-projection state holding function for holding the projectable portion in a non-projection state.

Figure 32:
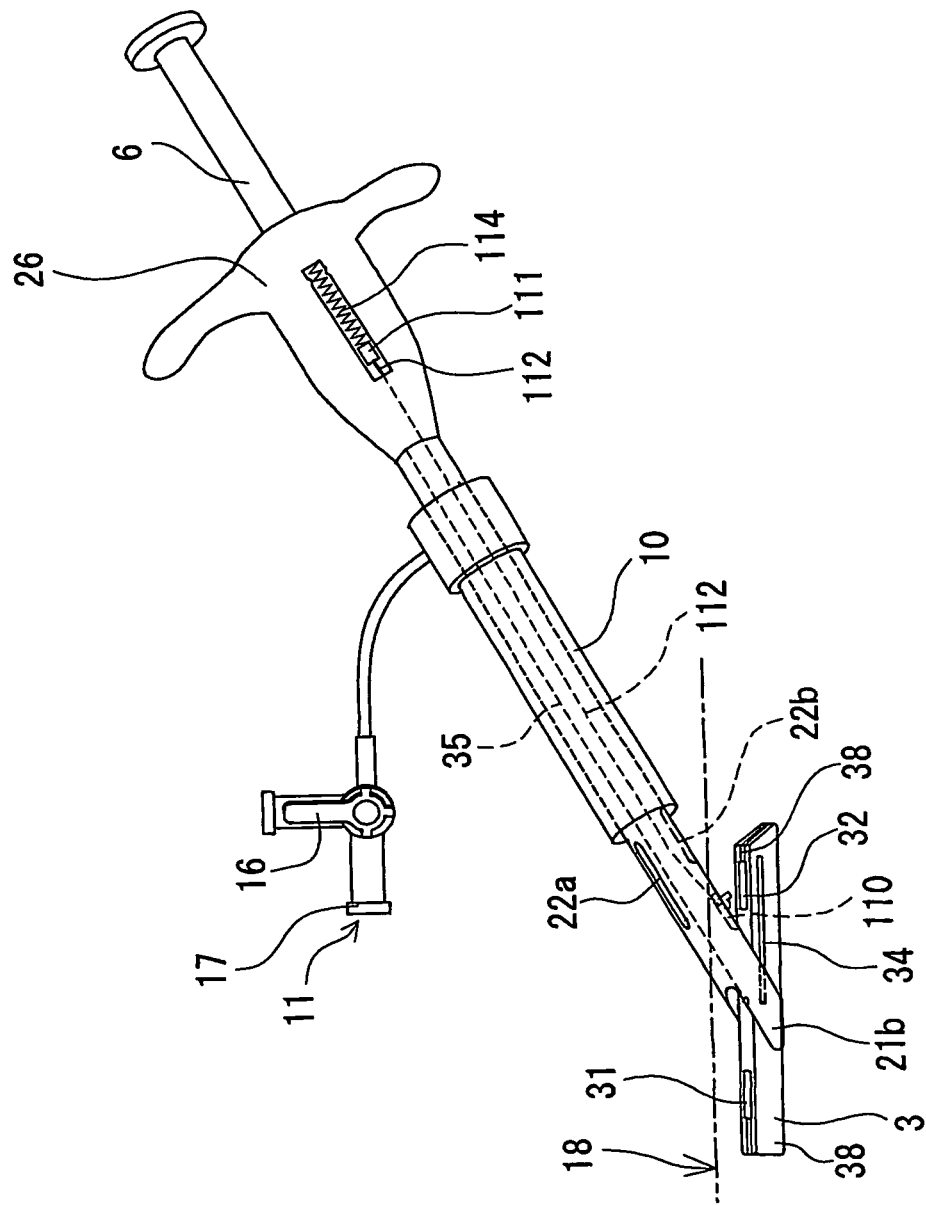
FIG. 32 is an explanatory view for explaining the operation of the organism tissue suturing apparatus of the present invention.
Figure 33:
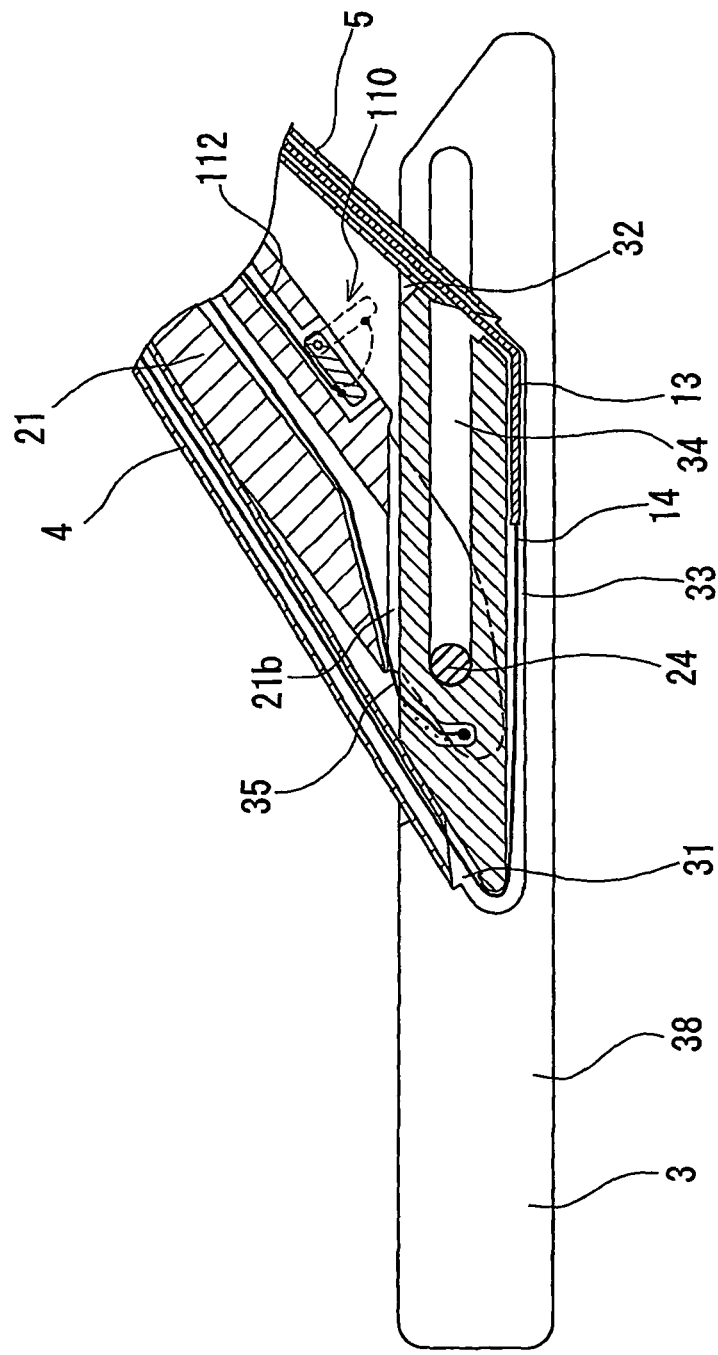
FIG. 33 is an explanatory view for explaining the operation of the organism tissue suturing apparatus of the present invention.

The operation of the organism tissue suturing apparatus 100 of the present invention is described below with reference to FIGS. 32 and 33.

The display portion 111 is engaged by projections 115a, 115b to hold the projectable portion 110 in a non-projection state. Thereafter the organism tissue suturing apparatus 100 is inserted into the introducer sheath 10, for use in treatment or diagnosis, whose front end has reached the tissue of the organism through the hole formed in the tissue membrane of the organism. After a projectable member 110a is inserted into the sheath 10, the display portion 111 is pressed forward to disengage the display portion 111 from the projections 115a, 115b.

As the organism tissue suturing apparatus 100 is inserted into the introducer sheath 10, the organism tissue suturing apparatus 100 is inserted into the blood vessel. Thereby the projectable member 110a is exposed in the blood vessel and is not pressed by the sheath 10. Thus the projectable member 110a projects into the blood vessel, and the display portion 11 moves forward. Thus it is possible to confirm that the projectable member 110a is disposed in the blood vessel.

When the projectable member 110a is disposed in a subcutaneous tissue outside the blood vessel as a result of slow pulling of the organism tissue suturing apparatus 100 toward the operator, the projectable member 110a is pulled into a body part 62. This fact can be confirmed by the display portion 111. The organism tissue suturing apparatus 100 is placed in position. At this time, the rotary portion 3 and the front end 21b of the body part of the shaft are disposed in the blood vessel, and the body portion 21a of the shaft are not disposed in the blood vessel.

An organism tissue suturing apparatus according to another embodiment of the present invention will be described below.

Figure 34:
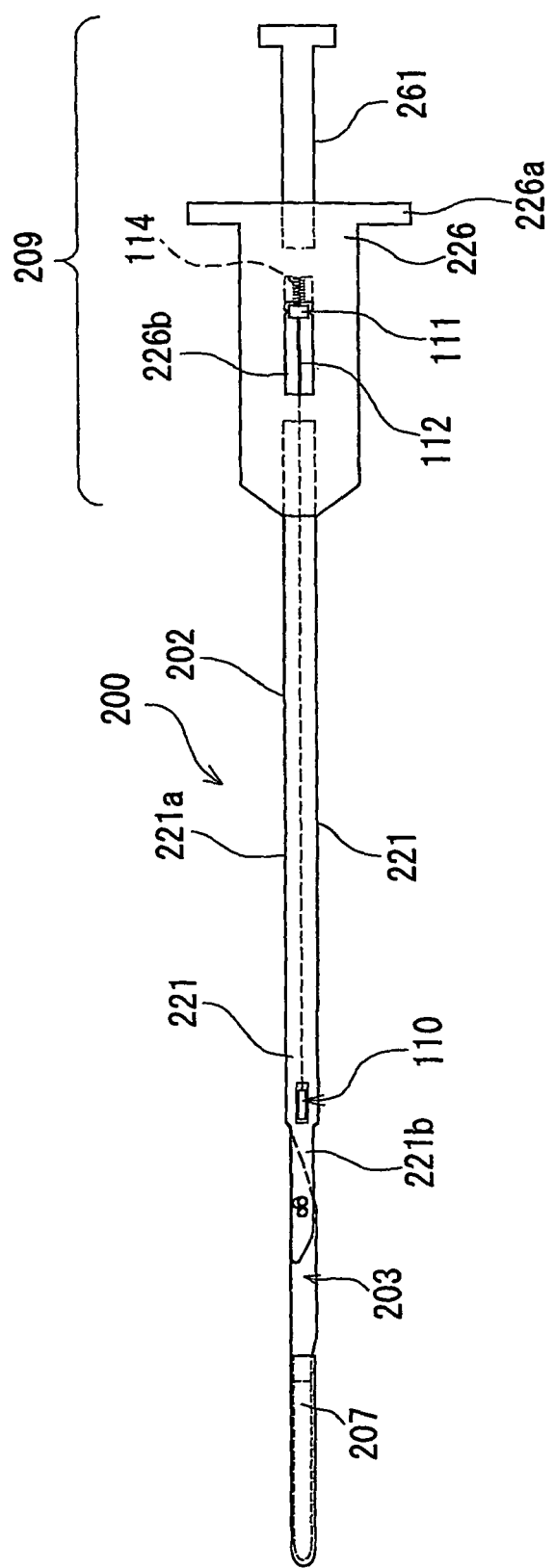
FIG. 34 shows an outlook of an organism tissue suturing apparatus according to an embodiment of the present invention.
Figure 35:
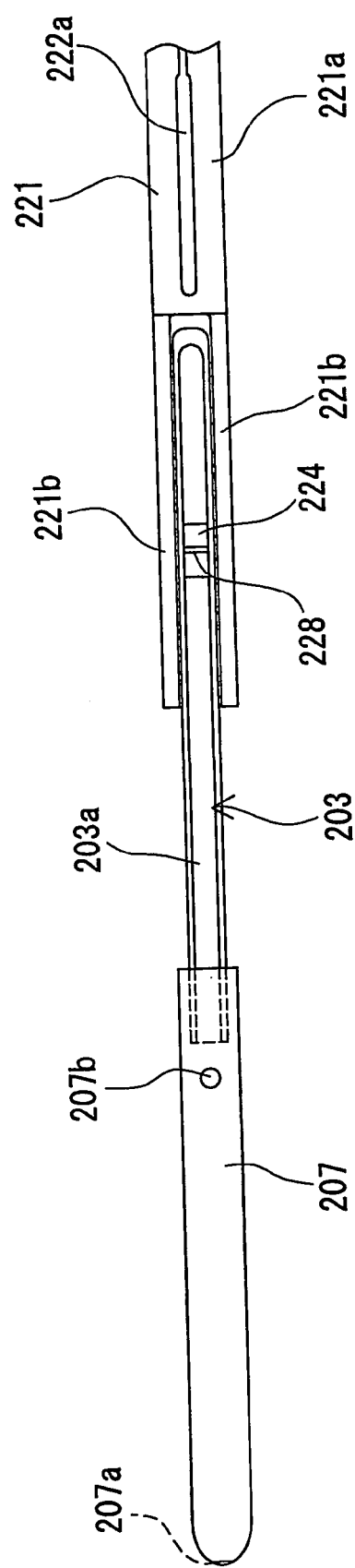
FIG. 35 is an enlarged plan view showing a front side of a body part of the organism tissue suturing apparatus shown in FIG. 34.
Figure 36:
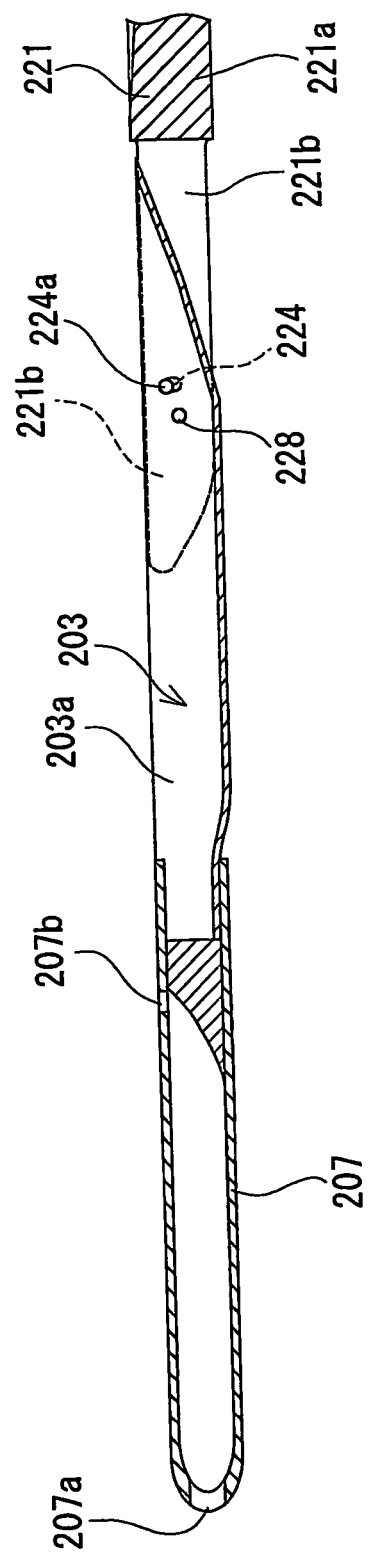
FIG. 36 is an enlarged plan view showing the front side of the organism tissue suturing apparatus shown in FIG. 34.
Figure 37:
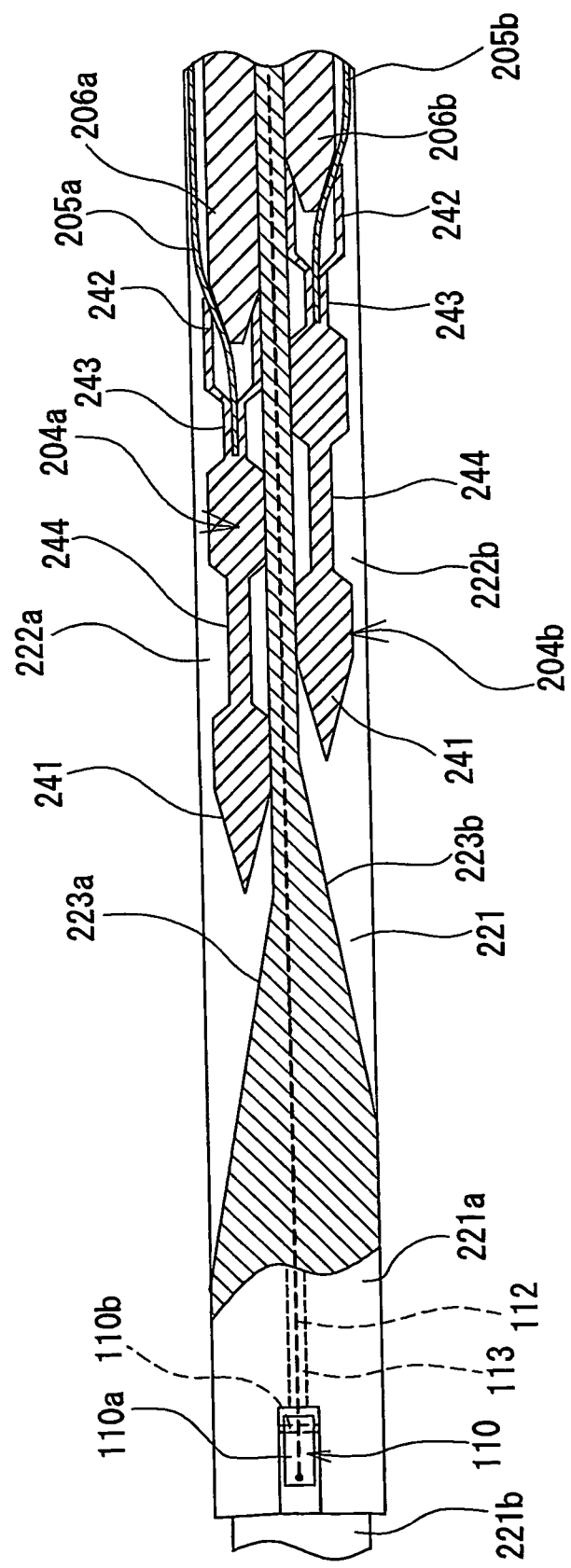
FIG. 37 is a partly enlarged sectional view showing showing the body part of the organism tissue suturing apparatus shown in FIG. 34.
Figure 38:
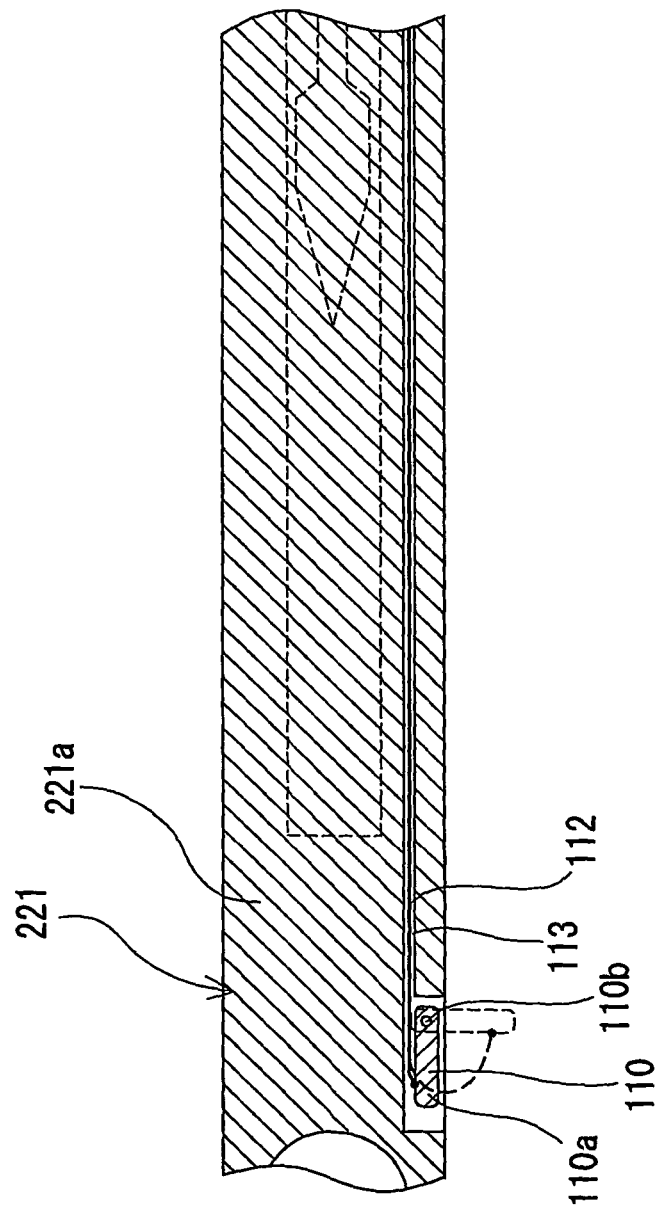
FIG. 38 is an enlarged sectional view showing the vicinity of the projectable portion of the organism tissue suturing apparatus shown in FIG. 34.
Figure 39:
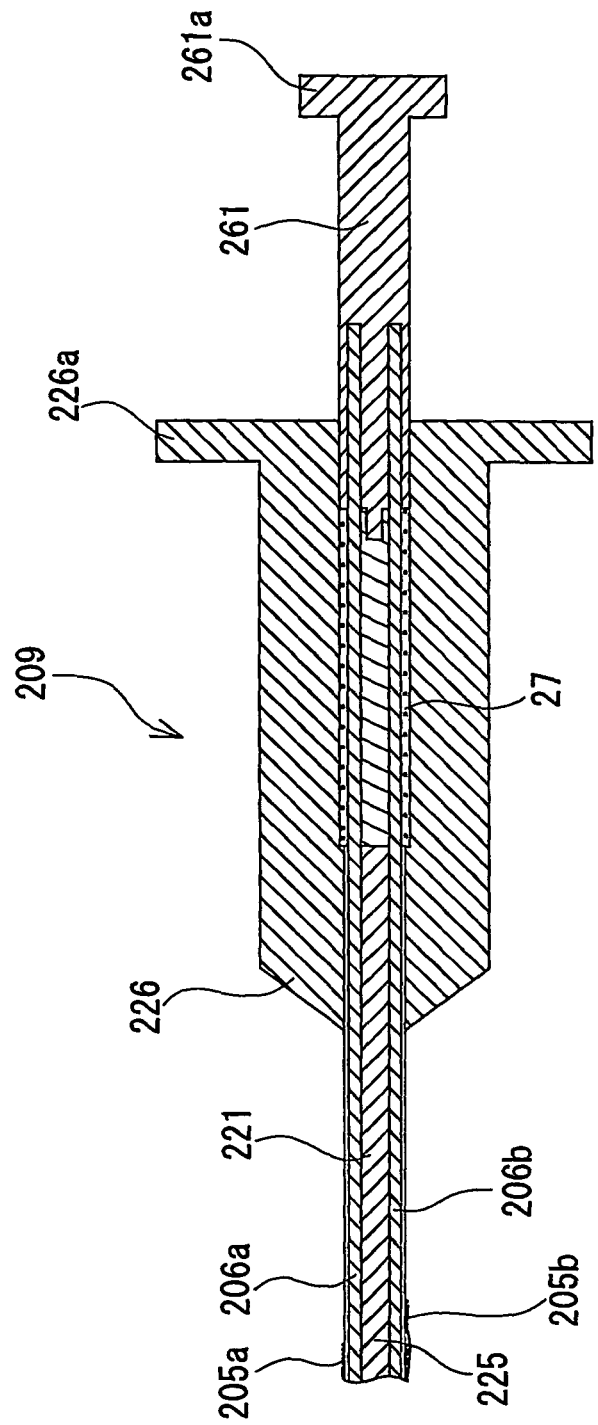
FIG. 39 is an enlarged sectional view showing a rear side of the organism tissue suturing apparatus shown in FIG. 34.
Figure 40:
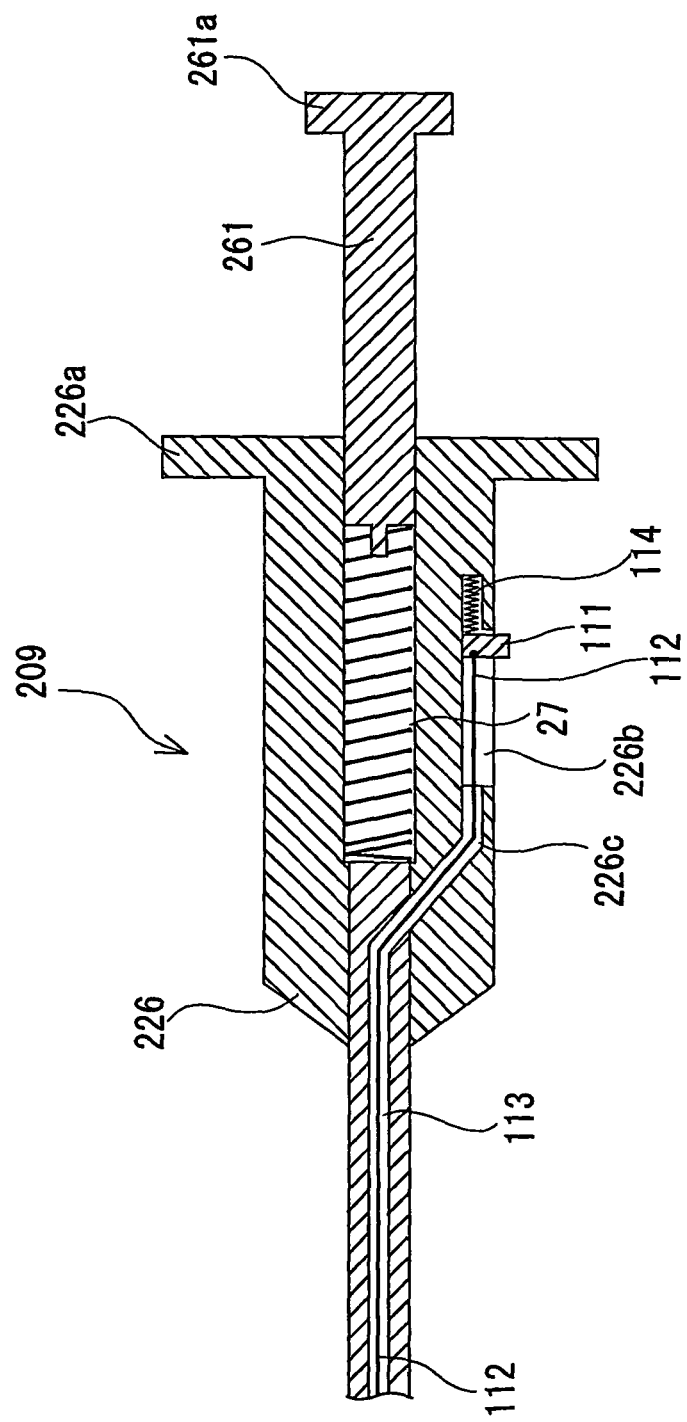
FIG. 40 is an enlarged sectional view showing the rear side of the organism tissue suturing apparatus cut at an angle different by 90 degrees from an angle of FIG. 39.
Figure 41:
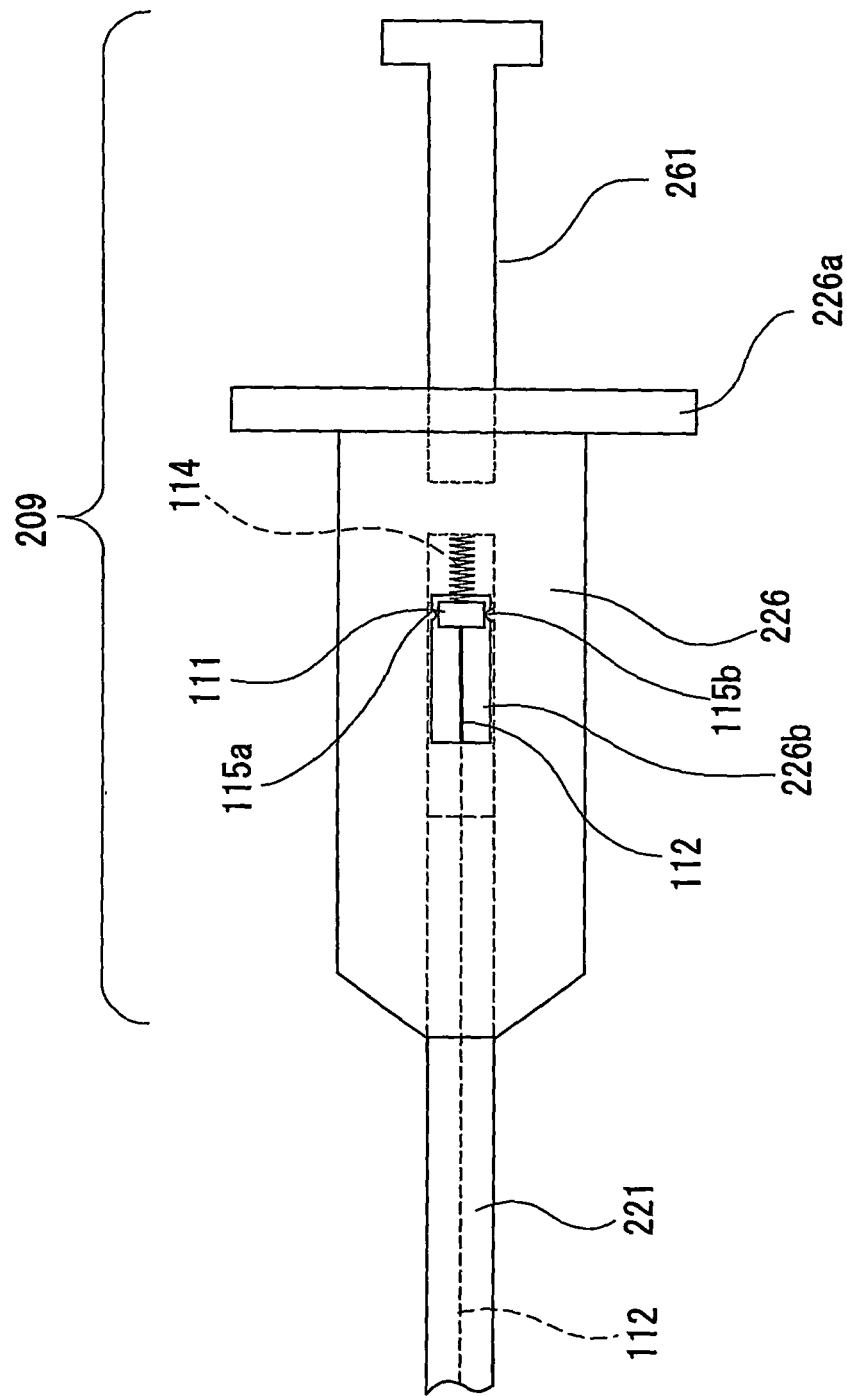
FIG. 41 is an enlarged plan view of the rear side of the organism tissue suturing apparatus shown in FIG. 34.

FIG. 34 shows an outlook of an organism tissue suturing apparatus according to an embodiment of the present invention. FIG. 35 is an enlarged plan view showing a front side of a body part of the organism tissue suturing apparatus shown in FIG. 34. FIG. 36 is an enlarged plan view showing the front side of the organism tissue suturing apparatus shown in FIG. 34. FIG. 37 is a partly enlarged sectional view showing the body part of the organism tissue suturing apparatus shown in FIG. 34. FIG. 38 is an enlarged sectional view showing the vicinity of a projectable portion of the organism tissue suturing apparatus shown in FIG. 34. FIG. 39 is an enlarged sectional view showing a rear side of the organism tissue suturing apparatus shown in FIG. 34. FIG. 40 is an enlarged sectional view showing the rear side of the organism tissue suturing apparatus cut at an angle different by 90 degrees from an angle of FIG. 39. FIG. 41 is an enlarged plan view of the rear side of the organism tissue suturing apparatus shown in FIG. 34.

The organism tissue suturing apparatus 200 of the embodiment for suturing a penetrated hole formed subcutaneously in a tissue membrane of an organism has a body part with a predetermined length. The body parts includes a rotary portion, disposed at a front end thereof, that can be inserted into the tissue of the organism from the hole; at least one needle accommodated in a portion, inside the body part, rearward from the rotary portion; a thread joined with the needle; and a pressing member for advancing the needle from a side surface of the body part and pressing the needle into the rotary portion. The rotary portion has a needle receiving portion for receiving the needle pressed into the rotary portion by the pressing member, with the rotary portion disposed in the tissue of the organism.

As shown in FIG. 34, the organism tissue suturing apparatus 200 of the embodiment has a body part 202, having a predetermined length, which can be inserted into the tissue of the organism. As shown in FIGS. 35 and 36, the body part 202 has a rotary portion 203 that can be inserted into the tissue of the organism and is rotatably supported by the body part so that the rotary portion 203 is rotatable in the tissue of the organism. As shown in FIG. 34, the body part 202 has an operation portion 209 provided at its rear side. The rotary portion 203 has a tube 207 provided at its front side.

The organism tissue suturing apparatus 200 of the embodiment has a position confirmation function for confirming the position of a blood vessel or a body cavity wall and a suturing function for suturing or dosing a penetrated hole which is formed subcutaneously in a tissue membrane of an organism. The organism tissue suturing apparatus 200 does not have to be necessarily provided with the position confirmation function.

More specifically, as shown in FIG. 34, the body part 202 has a shaft 221 and a hub (shaft hub) 226 disposed at the rear side thereof. As shown in FIGS. 34, 37, and 38, the shaft 221 has a body portion 221a thereof and a front end 221b thereof, for supporting the rotary portion 203, extending forward from the front end of the body portion 221a. A projectable portion 110 is formed at the front end of body portion 221a of the shaft of the body part 202. As shown in FIG. 38, body portion 221a has a projectable portion accommodation portion provided at the front end thereof and a lumen 113 communicating with the projectable portion accommodation portion and extending rearward. The projectable portion 110 has a projectable member 110a rotatably supported on the body portion 221a by a pin 110b.

It is preferable that the axial length of the projectable member 110a is 1.5 to 6.0 mm and that the axial width is 0.5 to 5.0 mm.

It is possible to use the following materials for the projectable member: Macromolecular materials including polyolefin such as polypropylene, polyethylene, and the like, olefin elastomer (for example, polyethylene elastomer, polypropylene elastomer), polyester such as polyethylene terephthalate, flexible polyvinyl chloride, polyurethane, urethane elastomer, polyamide, amide elastomer (for example, polyamide elastomer), polytetrafluoroethylene, fluorocarbon resin elastomer, polyimide, ethylene-polyvinyl chloride copolymer, and silicone rubber; and metals such as stainless steel, Ni—Ti alloy, Cu—Zn alloy, Ni—Al alloy, tungsten, tungsten alloy, titanium, titanium alloy, cobalt alloy, tantalum; and an appropriate combination of these substances.

The projectable portion 110 has a projectable member 110a accommodated in the body part 202, rotatably supported, and projecting from a side surface of the body part 202, when the projectable member 110a pivots; and a wire 112 whose one end is fixed to the projectable member 110a and other end is fixed to a display portion 111 and movably accommodated in the body part 202.

More specifically, as shown in FIGS. 37, 38, and 40, a front end portion of the wire 112 is fixed to a front end portion of the projectable member 110a, and a rear end of the wire 112 is fixed to the display portion 111. The wire 112 movably passes inside a lumen 113 formed inside the body portion 221a of the shaft, reaches the inside of the hub 226, passes a duct 226c formed inside the hub 226, thus being fixed to the display portion 111, as shown in FIG. 40.

The display portion 111 is slidable inside a slide port 226b formed in the hub 226. An urging member 114 urges the display portion 111 forward. The urging force of the urging member 114 is transmitted to the projectable member 110a through the wire 112. As a result, the projectable member 110a is urged in its projection direction. That is, the projectable portion 110 keeps a projection state when no external force is applied thereto, whereas it keeps a non-projection state when an external force is applied thereto. In other words, the position confirmation device has the urging means for keeping the projectable portion 110 in the projection state.

The following materials are suitable for the wire 112: Stainless steel wire (preferably, stainless steel having high tensile force for spring), piano wire (preferably, nickel-plated or chromium-plated), super-elastic alloy wire, Ni—Ti alloy, Cu—Zn alloy, Ni—Al alloy, tungsten, tungsten alloy, titanium, titanium alloy, cobalt alloy, tantalum; macromolecular materials having a comparatively high rigidity such as polyamide, polyimide, ultra-high-molecular-weight polyethylene, polypropylene, fluorocarbon resin; and a combination of these substances.

Resins having low frictional properties may be applied to the side surface of the towing wire to increase the lubricity thereof. As the resins having low frictional properties, it is possible to use fluorocarbon resin, nylon 66, polyether ether ketone, and high-density polyethylene. The fluorocarbon resin is more favorable than other resins. As the fluorocarbon resin, it is possible to use polytetrafluoroethylene, polyvinylidene fluoride, ethylene tetrafluoroethylene, and perfluoroalkoxy resin. Silicon or hydrophilic resins may be applied to the side surface of the towing wire.

An elastic member is preferable as the urging member 114. For example, a coil spring and rubber that are used in the embodiment are suitable. Instead of the urging member for pressing the display portion, a member of pressing the wire forward can be adopted.

The projectable portion 110 is pressed by a subcutaneous tissue and in a non-projection state until the projectable portion 110 reaches a blood vessel or a body cavity. When the projectable portion 110 is disposed (reaches) in the blood vessel or the body cavity, the projectable portion 110 is not pressed by the subcutaneous tissue and thus projects from the body part That is, until the projectable portion 110 reaches the blood vessel or the body cavity, the projectable portion 110 has the non-projection state (accommodated state) shown with a solid line of FIG. 38. When the projectable portion 110 reaches the blood vessel or the body cavity, the projectable portion 110 is not pressed by the subcutaneous tissue and thus moves to the projection state shown with a broken line of FIG. 38.

Owing to the transition from the non-projection state to the projection state, the wire 112 and the display portion 111 move to the front side. By checking the display portion 111, whether the projectable member 110a is positioned in the blood vessel or the body cavity can be easily visually observed. In the organism tissue suturing apparatus 200, the urging member urges the display portion 111 and the projectable member 110a in the projected direction. Thus when the projectable member 110a is disposed in the blood vessel or the body cavity, the display portion moves automatically. Thus whether the projectable member 110a is positioned in the blood vessel or the body cavity can be easily confirmed.

The organism tissue suturing apparatus 200 of the embodiment has a non-projection state holding function for holding the projectable portion in a non-projection state. More specifically, as shown in FIG. 41, the organism tissue suturing apparatus 200 has projections 115a, 115b, constituting the non-projection state holding function, provided on a side surface of a slide port 226b of the shaft hub 226. The projections 115a, 115b lock the display portion 111 thereto removably. The distance between the projections 115a and 115b is a little smaller than the width of the display portion 111 to grip the side surface of the display portion 111 so that the display portion is incapable of moving. The non-projection state holding function does not necessarily have to be provided with the opposed projections, but is necessary to removably lock the display portion 111.

For example, the non-projection state holding function may be constituted of one projection. Otherwise, the non-projection state holding function may be constituted by narrowing the width of the slide port In the case where the organism tissue suturing apparatus 200 has the non-projection state holding function, as shown in FIG. 41, the organism tissue suturing apparatus 200 is inserted into the organism, with the display portion held in the non-projection state by the non-projection state holding function. When it is determined that the organism tissue suturing apparatus has reached the blood vessel or the body cavity or when it is determined that the organism tissue suturing apparatus is proximate thereto, holding of the display portion by the non-projection state holding function is disclosed and the display portion is operated. The provision of the non-projection state holding function facilitates the insertion of the organism tissue suturing apparatus into the organism.

Figure 42:
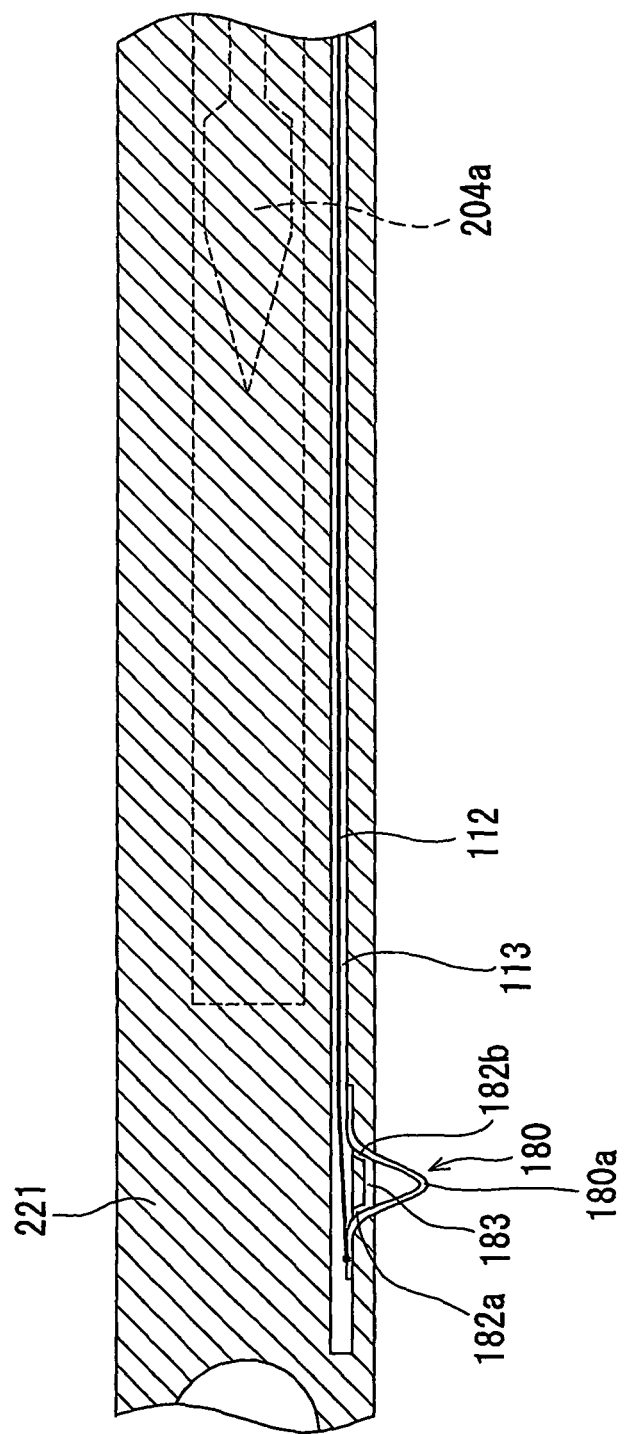
FIG. 42 is an explanatory view of an organism tissue suturing apparatus according to another embodiment of the present invention.

The projectable portion is not limited to the above-described embodiment For example, a projectable portion of an organism tissue suturing apparatus as shown in FIG. 42 may be adopted. The organism tissue suturing apparatus has a projectable portion accommodation portion provided at a front portion of a body portion 221a of a shaft; and a lumen 113 communicating with the projectable portion accommodation portion and extending rearward. The projectable portion has a projectable member 180a which can be deformed in a curved configuration by an elastic material. The rear end of the projectable member 180a is fixed to the body portion 221a of the shaft. The front end of the projectable member 180a is movable forward.

It is preferable that the projectable member 180a has an axial length of 4.0 to 20.0 mm and an axial width of 0.5 to 5.0 mm. It is possible to use the following materials for the projectable member 180a: Metals such as stainless steel, Ni—Ti alloy, Cu—Zn alloy, Ni—Al alloy, tungsten, tungsten alloy, titanium, titanium alloy, cobalt alloy, tantalum; and a combination of these substances. It is also possible to use the following macromolecular materials for the projectable member 180a: polyolefin such as polypropylene, polyethylene, and the like, olefin elastomer (for example, polyethylene elastomer, polypropylene elastomer), polyester such as polyethylene terephthalate, flexible polyvinyl chloride, polyurethane, urethane elastomer, polyamide, amide elastomer (for example, polyamide elastomer), polytetrafluoroethylene, fluorocarbon resin elastomer, polyimide, ethylene-vinylacetate copolymer, and silicone rubber; and an appropriate combination of these macromolecular materials.

More specifically, as shown in FIG. 42, the front end portion of the wire 112 is fixed to the front end portion of the projectable member 180a, and the rear end portion of the wire 112 is fixed to the display portion 111. The wire 112 movably passes inside the lumen 113 formed inside the body portion 221a of the shaft, reaches the inside of the hub 266, passes the duct 226c formed inside the hub 226, thus being fixed to the display portion 111, as in the case of the organism tissue suturing apparatus shown in FIG. 40. The display portion 111 is slidable inside the slide port 226b formed in the hub 226. The urging member 114 urges the display portion 111 toward the front end of the organism tissue suturing apparatus. The urging force of the urging member 114 is transmitted to the projectable member 180a through the wire 112. As a result, the projectable member 180a is urged in the projection direction.

That is, a projectable portion 180 is towed rearward when no external force is applied thereto. Thus the projectable portion 180 always keeps a curved state, in other words, a projection state. On the other hand, when an external force is applied thereto, the projectable portion 180 keeps a non-projection state. An elastic member is preferable as the urging member. For example, a coil spring and rubber that are used in the embodiment are suitable. Instead of the urging member for pressing the display portion, a member of pressing the wire forward can be adopted. In this embodiment, the projectable member and the wire may be integral with each other. The organism tissue suturing apparatus of this embodiment has side openings 182a, 182b for exposing the projectable member and a concave projectable portion accommodation portion 183 formed between the side openings 182a and 182b.

Until the projectable portion 180 reaches subcutaneously the blood vessel or the body cavity, it is pressed by a subcutaneous tissue and corrected in such a way that its curvature becomes low. Therefore the front end of the projectable portion 180 moves forward and the display portion is disposed at the forward side. When the projectable portion 180 is disposed (reaches) in the blood vessel or the body cavity, the projectable portion 180 is not pressed by the subcutaneous tissue and restored to the curved state. Therefore the front end of the projectable portion 180 moves rearward and thereby the display portion moves rearward. Accordingly by checking the display portion 111, it is easy to visually observe whether the projectable member 180a is disposed in the blood vessel or the body cavity.

In particular, in the embodiment, the urging means urges the display portion and the projectable member 180a in a projection direction. Thus when the projectable member 180a is disposed in the blood vessel or the body cavity, the display portion moves automatically, which can be confirmed easily. In the embodiment, it is preferable that the organism tissue suturing apparatus has the non-projection state holding function for holding the projectable portion in the non-projection state. The non-projection state holding function described in the above embodiment can be used.

As described above, it is preferable that the projectable portion 110 shifts automatically from the projection state in the blood or the body cavity to the non-projection state because the projectable portion 110 is pressed by the subcutaneous tissue, when the apparatus is pulled to the subcutaneous tissue. When the projectable portion 110 is pulled rearward in the state shown with the broken line of FIG. 38, the subcutaneous tissue presses the projectable member 110a forward. More specifically, the projectable member 110a pivots forward on a pin 110b and is accommodated in the body portion of the shaft. Therefore when the apparatus is pulled to the subcutaneous tissue, the degree of a resistance caused by the projectable member 110a is very low. Similarly, when the apparatus is pulled rearward in the state shown in FIG. 42, the subcutaneous tissue presses the projectable member 180a forward. The rear side of the projectable member 180a is fixed to the shaft, whereas its front side is not fixed thereto. Therefore the front side of the projectable member 180a moves to the front side to deform its curved portion. Consequently the curvature of the curved portion becomes small. Thus the projectable member 180a is accommodated in the body portion of the shaft. Therefore when the apparatus is pulled to the subcutaneous tissue, the degree of a resistance caused by the projectable member 180a is very low.

The body part of the organism tissue suturing apparatus 200 of the embodiment has the suturing function for suturing or closing a penetrated hole formed subcutaneously in the tissue membrane of the organism. The suturing function is described below.

The organism tissue suturing apparatus 200 of the embodiment has a body part 202, with a predetermined length, that can be inserted into the tissue of the organism from a hole and has a rotary portion 203 disposed at a front end portion thereof. The body part 202 has one needle 204 accommodated in a portion, inside the body part 202, rearward from the rotary portion 203; a thread 205 joined with the needle 204; and a pressing member 206 for advancing the needle 204 from a side surface of the body part 202 rearward from the projectable portion 110 and pressing the needle 204 into the rotary portion 203. The rotary portion 203 has a needle receiving portion 203a for receiving the needle 204 pressed into the rotary portion 203 by the pressing member 206, with the rotary portion 203 disposed in the tissue of the organism.

The organism tissue suturing apparatus 200 of this embodiment has two needles 204a, 204b; two pressing members 206a, 206b for pressing the two needles 204a, 204b respectively; and two accommodation portions 222a, 222b accommodating the needles 204a, 204b and the two pressing members 206a, 206b. It is preferable that the organism tissue suturing apparatus has a plurality of needles.

The body part 202 has the two needles 204a, 204b; threads 205a, 205b joined with the two needles 204a, 204b respectively; and two pressing members 206a, 206b for advancing the two needles 204a, 204b respectively from the side surface of the body part 202 and pressing them respectively into the rotary portion 203. The rotary portion 203 has a needle receiving portion 203a for receiving the needles 204a, 204b pressed into the rotary portion 203 by the pressing members 206a, 206b, with the rotary portion 203 disposed in the tissue of the organism. It is preferable that the needle receiving portion 203a is capable of holding the received needles.

More specifically, as shown in FIGS. 36 and 37, the body part 202 has a shaft 221 having accommodation portions 222a, 222b formed on a side surface of the shaft 221 and extending axially; and a hub (shaft hub) 226 disposed at a rear end of the shaft 221. The shaft 221 has a body portion 221a in which the accommodation portions 222a, 222b are formed; and a front end 221b, extending forward from a front end of the body portion 221a, for rotatably supporting the rotary portion 203. It is preferable that each of the accommodation portions 222a, 222b is a groove as shown in FIGS. 36 and 37. Each of the accommodation portions 222a, 222b may be a lumen having an opening at its front side.

It is preferable that the shaft 221 has a length of 30 to 500 mm and has an outer diameter of 1.0 to 10.0 mm. A comparatively hard resin or metal can be used as the material of the shaft 221.

The shaft 221 has the needles 204a, 204b accommodated in the accommodation portions 222a, 222b and the pressing members 206a, 206b. The tips of the threads 205a, 205b are fixed to the needles 204a, 204b. The threads 205a, 205b extend inside the accommodation portions 222a, 222b respectively and wound on the distal surface of the shaft or a part of the threads is accommodated (not shown) inside the shaft, with the threads 205a, 205b exposed from the accommodation portions at the rear side of the shaft 221.

The accommodation portions 222a, 222b are formed on the side surface of the shaft 221. The accommodation portions 222a, 222b extend axially to accommodate the pressing members and the needles. At the front end portion of the accommodation portions 222a, 222b, there are formed guide portions 223a, 223b for respectively advancing the needles 204a, 204b and the pressing members 206a, 206b obliquely and forwardly from the side surface of the body part 202. The guide portions 223a, 223b are formed by inclining the inner surface of the front end of the accommodation portions 222a, 222b respectively toward the side surface of the shaft 221. It is preferable that the distance between the front end of the guide portions 223a, 223b and that of the body portion 221a of the shaft 221 is 3.0 mm to 60.0 mm. The guide portions 223a, 223b are disposed rearward from the projectable portion 110.

As shown in FIG. 37, the guide portion 223b of the second accommodation portion 222b is disposed a little nearer to the rear end of the body part 202 than the guide portion 223a of the first accommodation portion 22a so that the needle 204b and the pressing member 206b advance nearer to the rear end of the body part 202. That is, the front end of the second guide portion 223b is disposed nearer to the rear end of the body part 202 than the front end of the first guide portion 223a. This construction is suitable for suturing a blood vessel through an oblique (for example, 30 degrees to 60 degrees) hole formed subcutaneously in penetration through the tissue membrane of the organism. The guide portions 223a, 223b of the accommodation portions 222a, 222b are formed wider than the width of other openings of the accommodation portions.

As shown in FIG. 37, the needles 204a, 204b have a cutting face 241 for piercing an internal membrane at a front portion thereof and a concavity 242 for receiving the front end of the pressing members 206a, 206b. The needles 204a, 204b have a thread-fixing portion 243 and a deformation-assistant portion 244 for assisting deformation of the needles. In this embodiment, the diameter of the deformation-assistant portion 244 is smaller than that of other portions of the needle. The thread-fixing portion 243 is formed by caulking a portion for accommodating the tip of the thread inserted into a hollow portion of the needles 204a, 204b at the rear side thereof.

The needles 204a, 204b may be solid or hollow. It is preferable that each of the needles 204a, 204b has an outer diameter of 0.1 to 1.0 mm and a length of 5.0 to 50.0 mm. Metal and macromolecular materials having comparatively high rigidities can be used for the needles 204a, 204b. Resins having low frictional properties may be applied to the side surface or outer surface of the needles 204a, 204b to increase the lubricity thereof. The above-described resins having low frictional properties can be used.

The tips of the threads 205a, 205b are fixed to the needles 204a, 204b respectively. As shown in FIG. 37, the threads 205a, 205b extend rearward inside the accommodation portions 222a, 222b respectively along the side surface of the pressing members 206a, 206b respectively and wound on the distal surface of the shaft 221, with the threads 205a, 205b exposed to the outside at the rear side of the shaft 221. The threads may be accommodated inside the shaft As the material for the threads, known suturing threads can be used. It is possible to use a suturing thread that is absorbed or not absorbed by the organism. It is preferable that the suturing thread has a diameter of 0.01 to 1.0 mm and a length of 100 to 1500 mm.

As shown in FIGS. 34, 39, 40, and 41, the body part 202 has a hub 226 disposed at its rear side. The hub 226 has a duct accommodating the rear side of each of the pressing members 206a, 206b. The hub 226 has a flange portion 226a to be operated by an operator As shown in FIGS. 37 and 39, each of the pressing members 206a, 206b extends to the rear end of the shaft 221 through the accommodation portion, thus protruding rearward from the rear end of the shaft 221 and extending inside the duct of the hub 226. The rear end of each of the pressing members 206a, 206b is fixed to the pressing member operation portion 261 slidable in the duct of the hub 226. Therefore by pressing the pressing member operation portion 261 forward, the pressing member can be moved forward and the needles thereof can be pressed out of the body part 202.

The pressing member operation portion 261 may be provided for each of the pressing members 206a, 206b. It is preferable that the pressing members are urged by an urging means in a direction in which they do not advance. More specifically, the pressing member operation portion 261 is urged rearward by an elastic member 27 accommodated in the duct of the hub 226. It is preferable that as shown in FIGS. 39 and 40, a coil spring is used as the elastic member 27. The elastic member 27 may be provided between the flange portion 261a of the pressing member operation portion 261 and the hub 226.

As shown in FIG. 37, the pressing members 206a, 206b have a portion for pressing the needles 204a, 204b forward respectively. More specifically, the front end of each of the pressing members 206a, 206b is tapered and is thus capable of penetrating into the rear end of the needles 204a, 204b respectively. However, the pressing member presses the needle, and the pressing member and the needle do not engage each other. Thus when the pressing member is moved rearward, the pressing member separates from the needle.

It is preferable that each of the pressing members 206a, 206b has a diameter of 0.1 to 2.0 mm and a length of 30 to 600 mm. The pressing members 206a, 206b solid or hollow can be used.

Resins having low frictional properties may be applied to the side surface or outer surface of the needles 204a, 204b to increase the lubricity thereof. The above-described resins having low frictional properties can be used.

As shown in FIGS. 35 and 36, the rotary portion 203 having the needle accommodation portion 203a is rotatably supported by the front end 221b of the shaft 221. In the organism tissue suturing apparatus 200 of the embodiment, the rotary portion 203 has a rotation angle restriction function permitting the rotation thereof between a state (state shown in FIGS. 35 and 36) in which the rotary portion 203 is on an extension line of the axis of the body part 202 and a predetermined angle less than 90 degrees. It is preferable that the rotation angle restriction function permits the rotary portion to pivot at a predetermined angle less than 60 degrees. The rotation angle restriction function allows the needles 204a, 204b to be received in the rotary portion 203 securely. In the embodiment, as shown in FIGS. 35 and 36, the rotary portion 203 has a predetermined length and is open in the upper portion thereof entirely or partly and in the front portion thereof and cage-shaped.

The rotary portion 203 has a flat side surface. The rear side of the rotary portion 203 is disposed between the front ends 221b and 221b of the shaft. The rotary portion 203 is rotatably supported by a shaft 228 fixed to the front end 221b of the shaft 221. The rotary portion 203 has a pin 224 movable inside a loose opening 224a formed at the front end 221b of the shaft. The loose opening 224a has the shape of a circular arc having an axis 228 and a predetermined length. Thus the rotary portion 203 is pivotal within an angle formed on the loose opening 224a with respect to the axis 228. The inner bottom surface of the rear side of the rotary portion is inclined to guide the needle. The inside of the rotary portion 203 is axially hollow to form the needle receiving portion 203a. The loose opening 224a may be formed at the side of the rotary portion. In this case, the pin 224 is provided at the front end 221b of the shaft It is suitable that the rotary portion 203 has a width of 0.5 to 9.0 mm, a height of 0.8 to 10.0 mm, and a length of 2.0 to 60.0 mm.

The organism tissue suturing apparatus 200 has a tube 207 provided at the front end of the rotary portion 203. The tube 207 has an opening 207a at its front end and an opening 207b at its side surface. The tube 207 is provided to insert a guide wire thereinto. It is preferable that the tube 207 has a length of 10 to 600 mm and an outer diameter of 1.0 to 10.0 mm.

The operation of the organism tissue suturing apparatus 200 of the embodiment is described below with reference to FIGS. 43 through 48.

As shown in FIGS. 34 and 41, the display portion 111 is engaged by projections 115a, 115b to hold the projectable portion 110 in a non-projection state.

Thereafter a guide wire (not shown) is inserted into an introducer sheath (not shown), for use in treatment or diagnosis, whose front end has reached the tissue of the organism through the hole formed in the tissue membrane of the organism. Then the introducer sheath is removed from the tissue of the organism.

Figure 43:
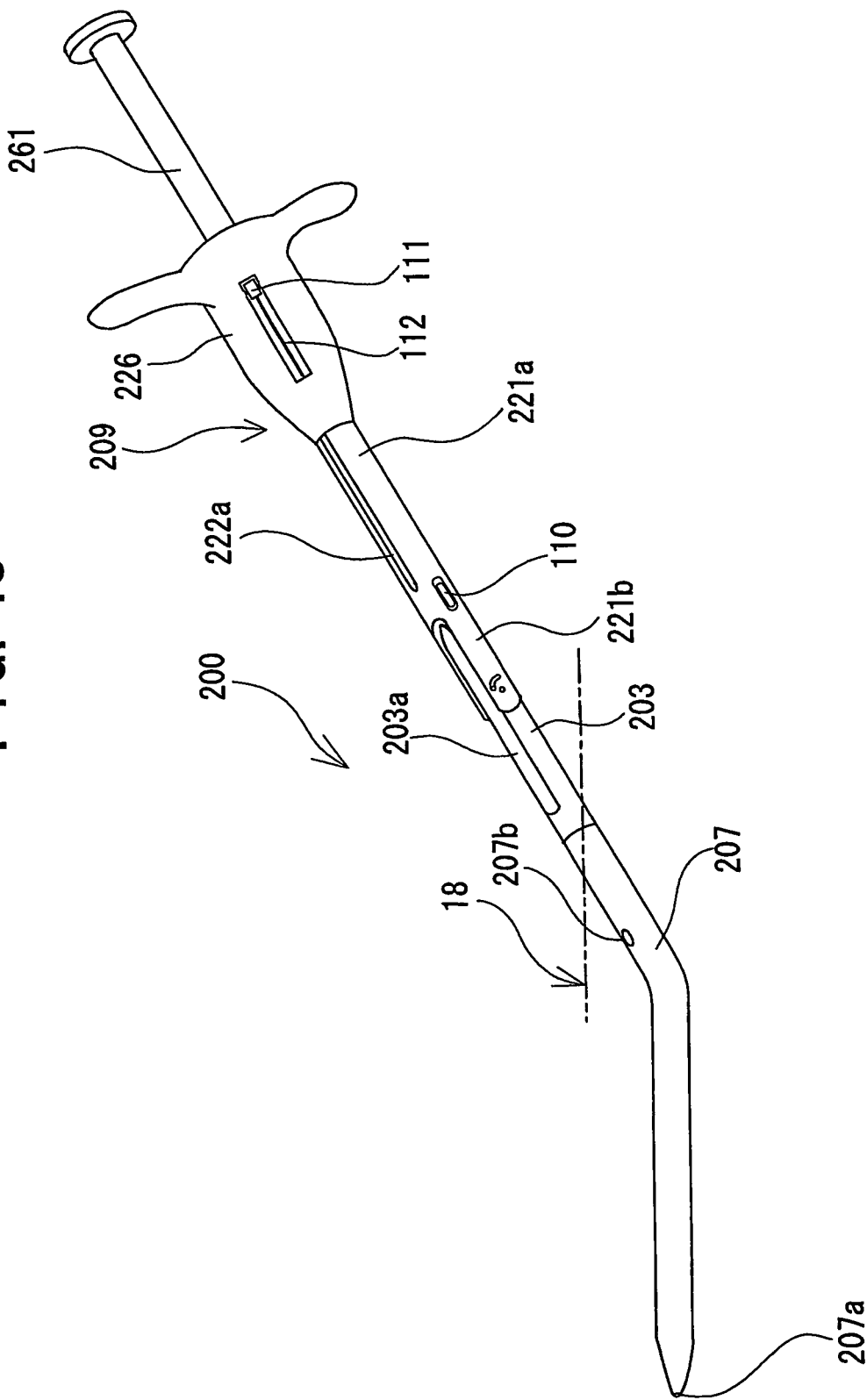
FIG. 43 is an explanatory view for explaining the operation of the organism tissue suturing apparatus of the present invention.

Thereafter the guide wire is inserted into the tube 207 from a front-end opening 207a of the tube 207 disposed at the front side of the organism tissue suturing apparatus 200 and then extended from a side opening 207b. After the tube 207 is inserted into the organism up to the side opening 207b, the guide wire is pulled out of the tube 207. Then as shown in FIG. 40, the organism tissue suturing apparatus 200 is inserted into the puncture site (tissue of organism having hole). FIG. 43 shows this state. After the projectable member 110a is inserted into the organism, the display portion 111 is pressed forward to disengage the display portion 111 from the projections 115a, 115b.

Figure 44:
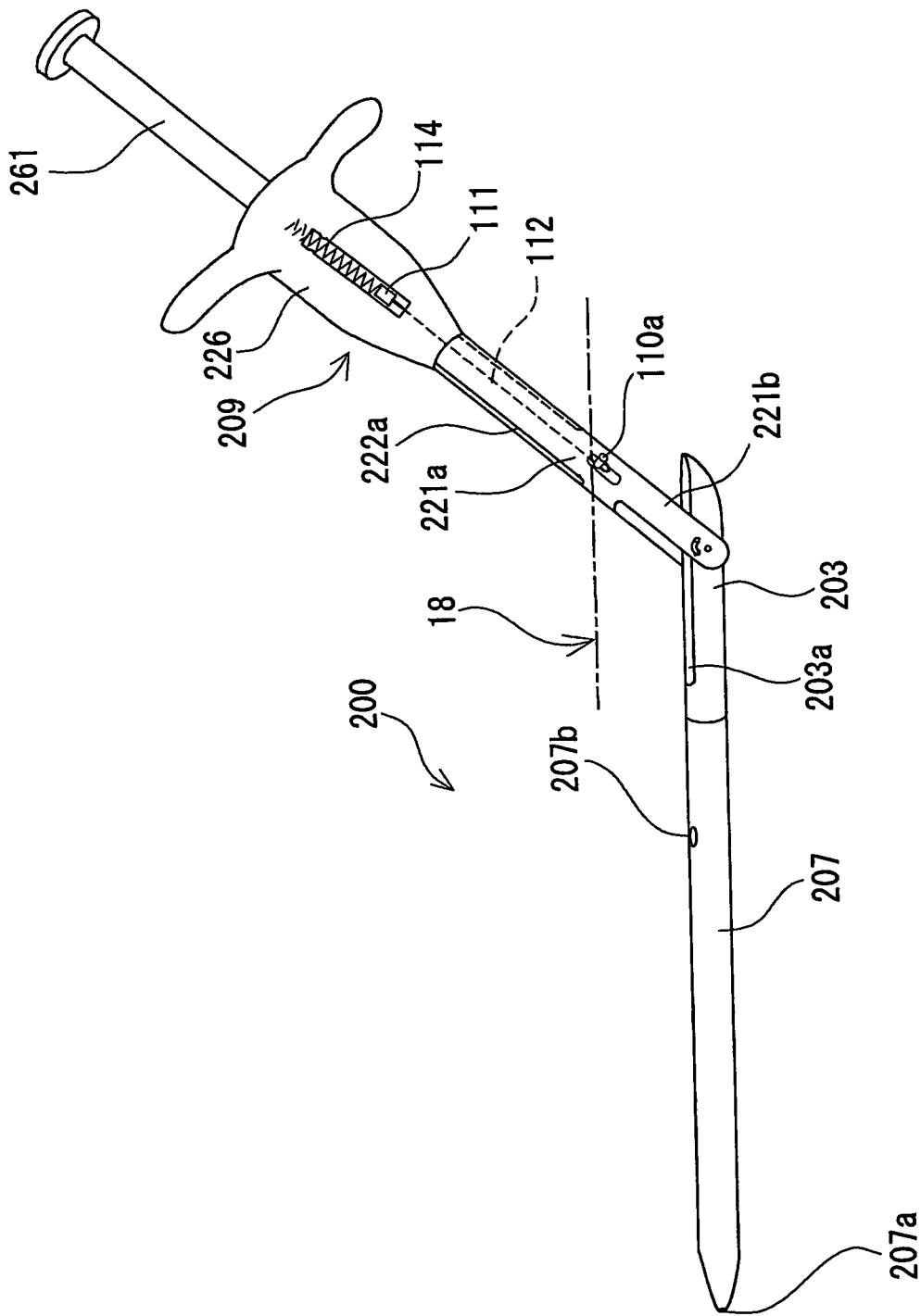
FIG. 44 is an explanatory view for explaining the operation of the organism tissue suturing apparatus of the present invention.

When the projectable member 110a has reached the inside of the blood vessel in the progress of the insertion of the organism tissue suturing apparatus, the projectable member 110a projects and the display portion 111 moves forward. Thereby from the outside, it is possible to confirm that the projectable member 110a has reached the inside of the blood vessel. FIG. 44 shows this state. A broken line 18 of FIG. 44 shows the wall of the blood vessel which is the tissue membrane of the organism. In this state, the rotary portion 203, the front end 221b of the shaft of the body part 202, and the front end of the body portion 221a of the shaft are disposed in the blood vessel. The rotary portion 203 pivots as shown in FIG. 44. Consequently the shaft 221 of the body part 202 inclines at a predetermined angle with respect to the axis of the rotary portion 203. Then the body part is raised so that a maximum angle restricted by the loose opening 224a is kept between the body part 202 and the rotary portion 203 keep.

Figure 45:
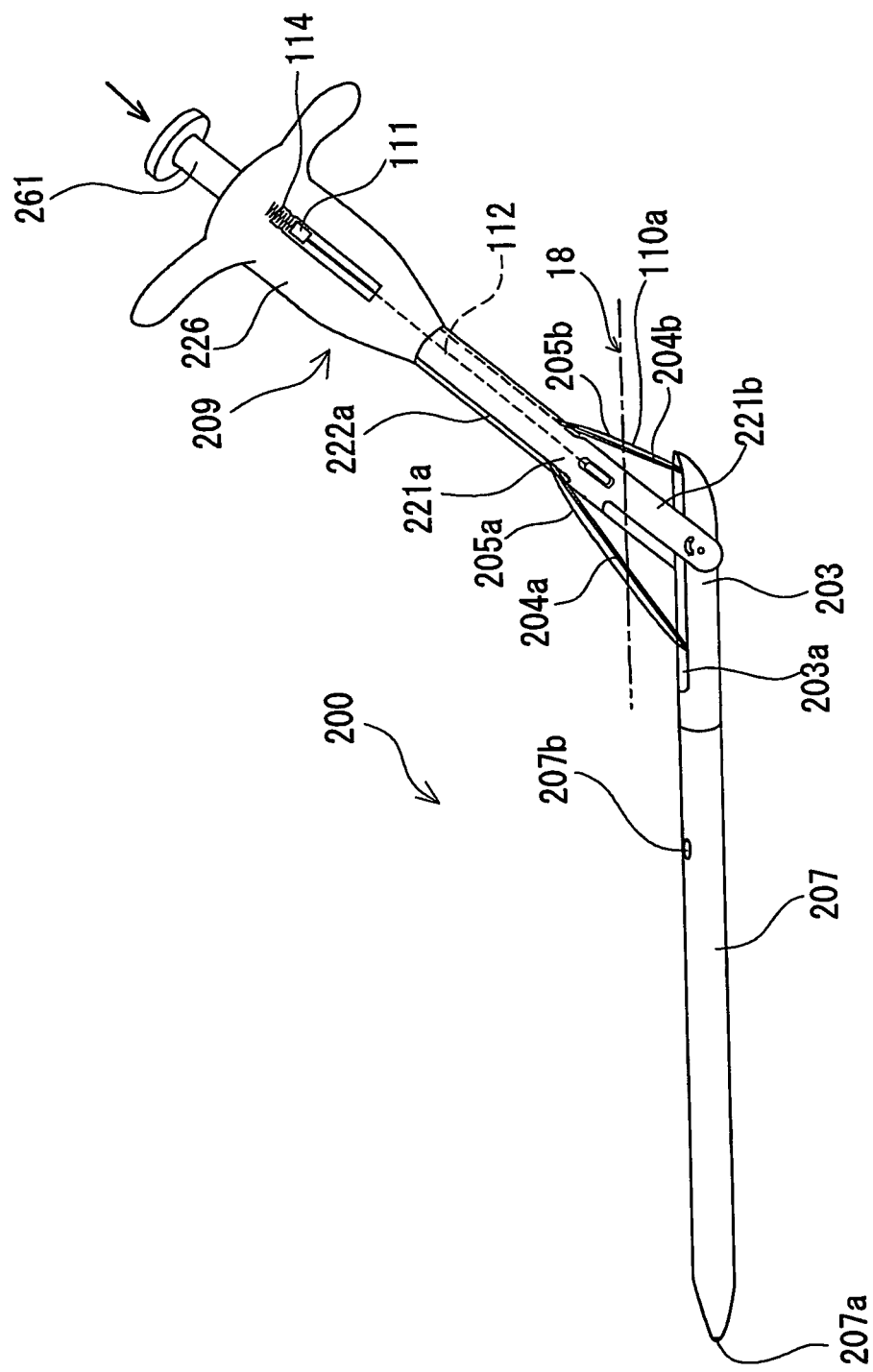
FIG. 45 is an explanatory view for explaining the operation of the organism tissue suturing apparatus of the present invention.
Figure 46:
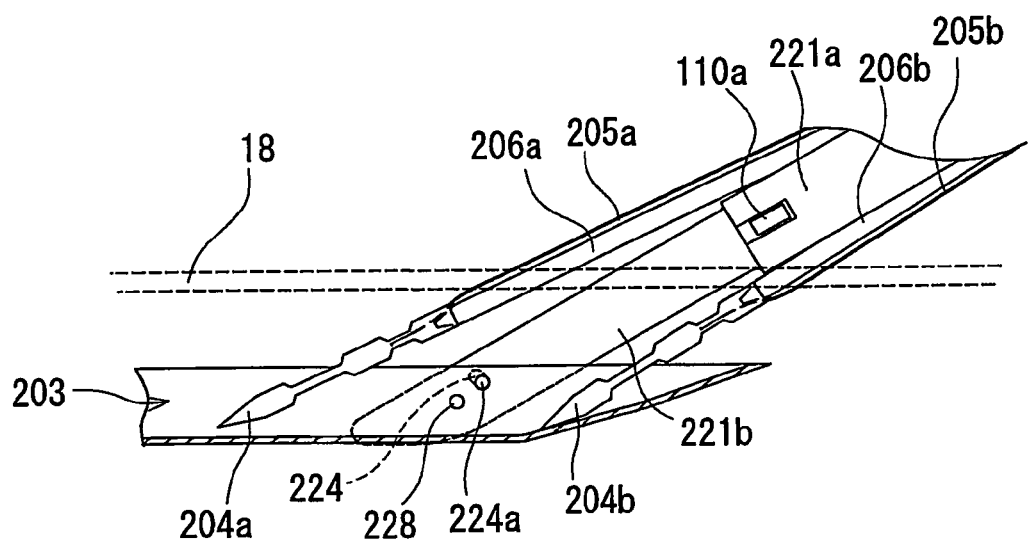
FIG. 46 is an explanatory view for explaining the operation of the organism tissue suturing apparatus of the present invention.

Thereafter as shown in FIG. 45, the entire organism tissue suturing apparatus is pulled out of the puncture site until the display portion 111 moves to the rear side, namely, until the projectable member 110a has the non-projection state. Then the pressing member operation portion 261 is pressed forward (direction with arrow) to advance the needles 204a, 204b obliquely from the front-side side surface of the body portion 221a of the body part 202 to penetrate the blood vessel wall 18. Thereby the threads 205a, 205b connected to the needles 204a, 204b respectively penetrate the blood vessel wall 18. When the pressing member operation portion 261 is pressed forward further, as shown in FIG. 46, the pressing members 206a, 206b penetrate the blood vessel wall 18, and the needles 204a, 204b reach the inside of the accommodation portion 203a of the rotary portion 203. When the pressing member operation portion 261 is pressed forward further (to position where maximum force is applied), the needles 204a, 204b are accommodated in the accommodation portion 203a of the rotary portion 203.

Figure 47:
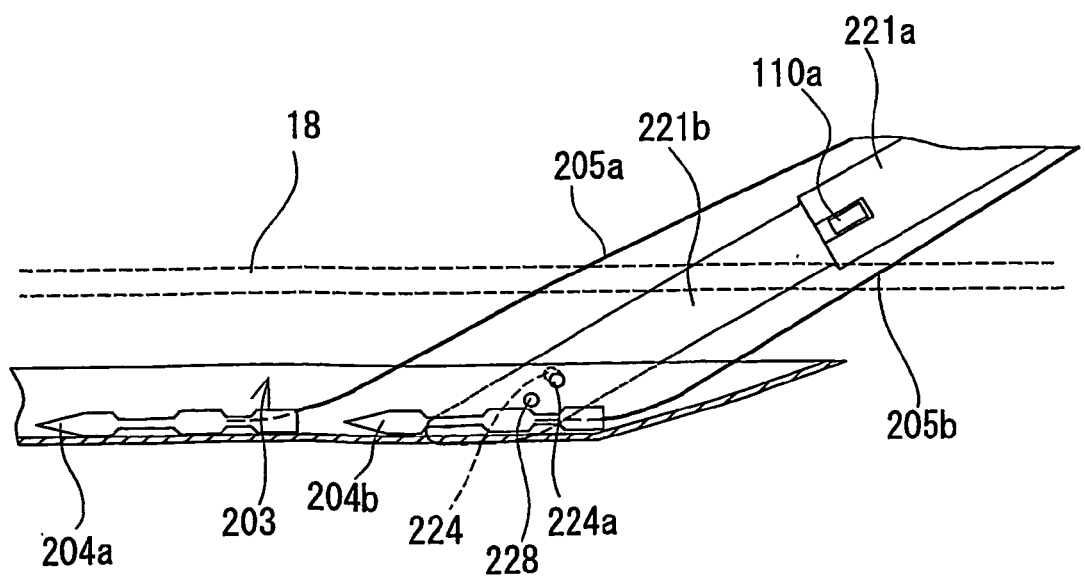
FIG. 47 is an explanatory view for explaining the operation of the organism tissue suturing apparatus of the present invention.

When pressing of the pressing member operation portion 261 is finished, as shown in FIG. 47, the pressing member operation portion 261 is returned to the unpressed state position because the pressing member operation portion 261 is urged rearward. Thus the pressing members 206a, 206b are accommodated in the body part 202.

In the organism tissue suturing apparatus, it is possible to perform an operation of piercing the blood vessel wall 18 and inserting the thread into a pierced portion with the needles 204a, 204b by pressing the rotary portion 203 forward in a short stroke so that the needles 204a, 204b disposed a little outward from the blood vessel wall 18 are accommodated respectively in the accommodation portion 203a of the rotary portion 203 disposed a little inward from the blood vessel wall 18. Thus the suturing operation can be performed easily.

Figure 48:
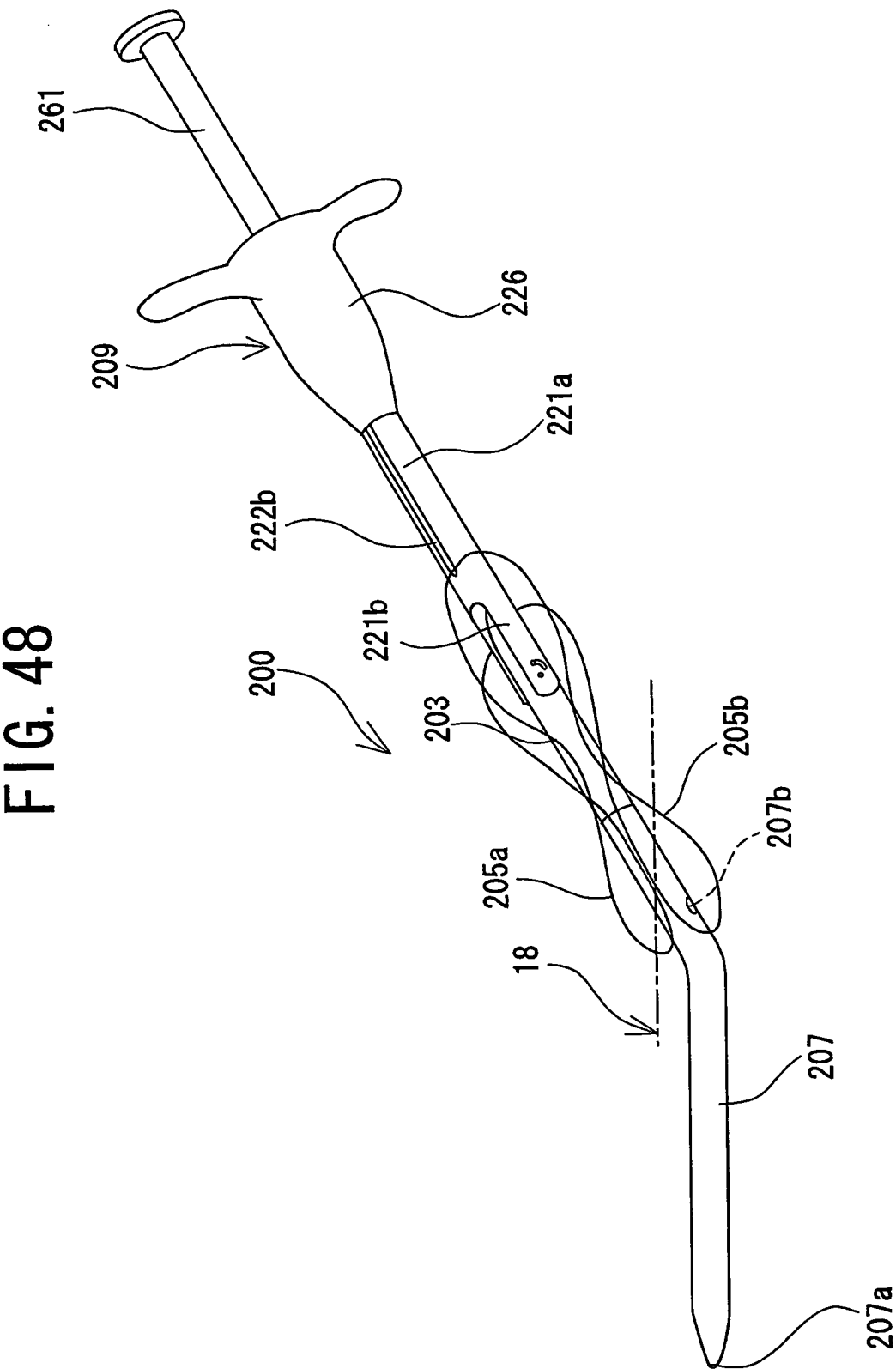
FIG. 48 is an explanatory view for explaining the operation of the organism tissue suturing apparatus of the present invention.

Thereafter as shown in FIG. 48, the organism tissue suturing apparatus 200 is rotated by about 180 degrees to make the entire apparatus linear. Then the apparatus 200 is pulled out of the puncture site. When the rotary portion 203 appears on the skin and the two threads 205a, 205b are visually observed, the pulling operation is stopped. Thereafter the two threads 205a, 205b accommodated in the accommodation portion 203a are cut. Then the second thread is tied with the first thread to form a knot. Thereafter the apparatus 200 is pulled completely from the organism, with the two threads being pulled.

After the two threads are pulled sufficiently, the knot formed with the second thread is moved along the first thread to the hole formed by piercing the blood vessel wall with a pressing instrument (not shown). After the pressing instrument is removed, the two threads are cut at a position proximate to the skin. Thereby the suturing operation is completed. The pressing instrument has a front-end opening and a side-surface opening communicating with the front-end opening to allow passage of the threads. It is preferable that the front end of the pressing instrument has an outer diameter of 1.0 to 5.0 mm and a length of 10.0 to 100.0 mm.

An organism tissue suturing apparatus 300 according to another embodiment of the present invention will be described below.

Figure 49:
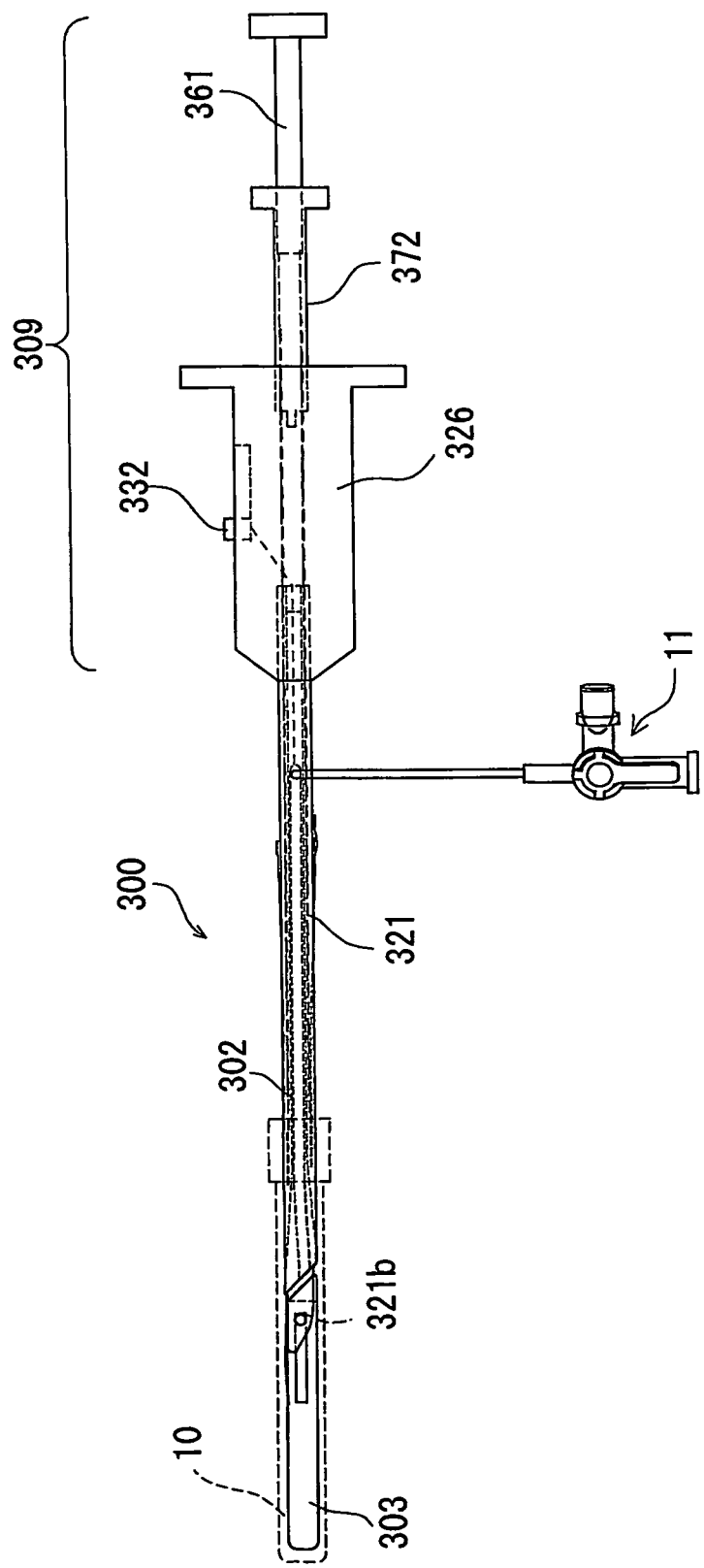
FIG. 49 shows an outlook of an organism tissue suturing apparatus according to an embodiment of the present invention.
Figure 50:
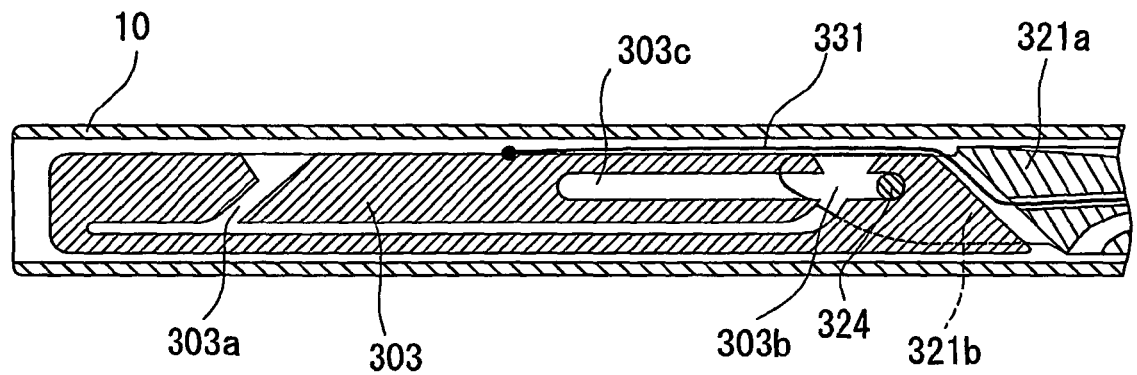
FIG. 50 is an enlarged sectional view showing the vicinity of a rotary portion of the organism tissue suturing apparatus shown in FIG. 49.
Figure 51:
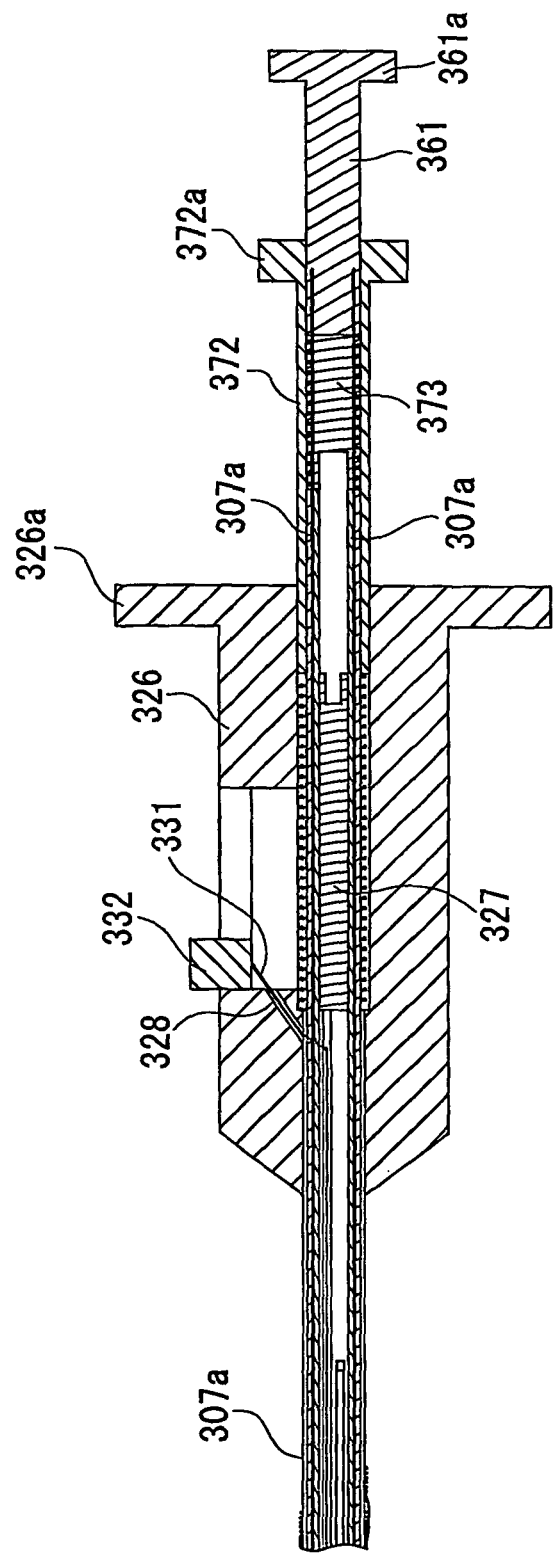
FIG. 51 is an enlarged sectional view showing the vicinity of a rear side of the organism tissue suturing apparatus shown in FIG. 49.
Figure 52:
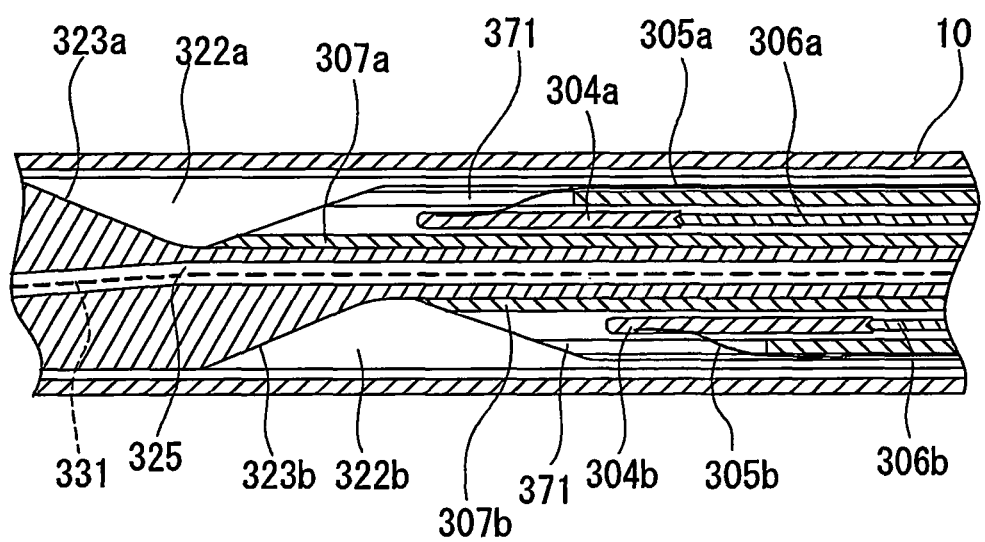
FIG. 52 is an enlarged sectional view showing the vicinity of a front side portion of a body portion of the organism tissue suturing apparatus shown in FIG. 49.
Figure 53:
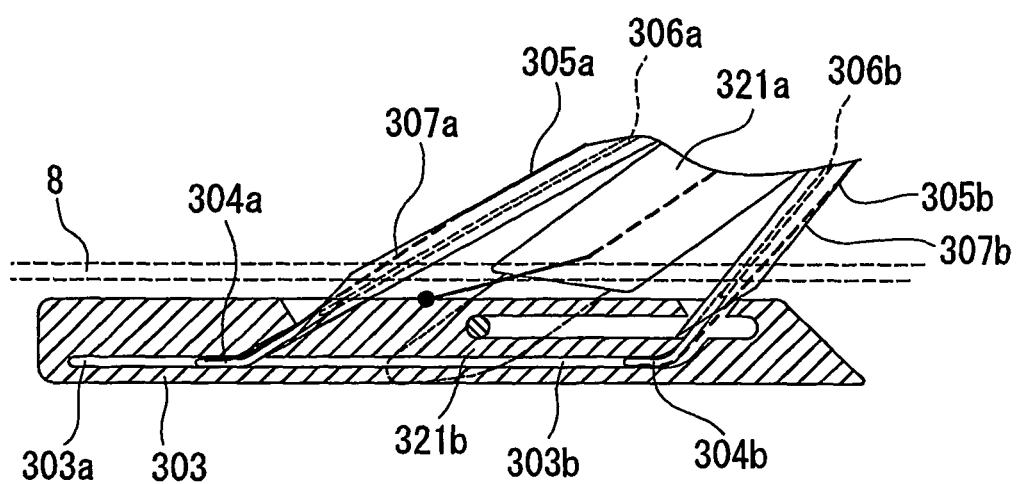
FIG. 53 is an explanatory views for explaining the operation of the organism tissue suturing apparatus of the present invention.
Figure 54:
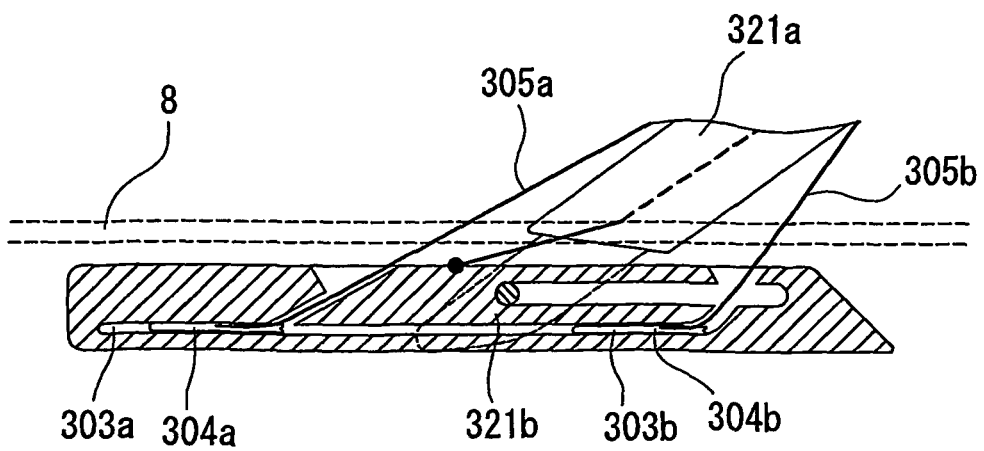
FIG. 54 is an explanatory views for explaining the operation of the organism tissue suturing apparatus of the present invention.

FIG. 49 shows an outlook of an organism tissue suturing apparatus according to an embodiment of the present invention. FIG. 50 is an enlarged sectional view showing the vicinity of a rotary portion of the organism tissue suturing apparatus shown in FIG. 49. FIG. 51 is an enlarged sectional view showing the vicinity of a rear side of the organism tissue suturing apparatus shown in FIG. 49. FIG. 52 is an enlarged sectional view showing the vicinity of a front side portion of a body portion of the organism tissue suturing apparatus shown in FIG. 49. FIG. 53 and FIG. 54 are explanatory views for explaining the operation of the organism tissue suturing apparatus of the present invention.

Similarly to embodiments shown in FIG. 1 to FIG. 33, this embodiment has two hollow needle members. This embodiment is different from the embodiments shown in FIG. 49 to FIG. 52 in that one thread, which is inserted into one hollow needle member, does not advance from a distal end opening of one hollow member to the other opening of a distal end opening of the other hollow member through one needle member receiving portion, the connection duct, the other needle member receiving portion, on the other hand, does not advance in U-turn direction, but both ends of one thread are pushed from each of distal end openings of two hollow needles, both ends of the thread is taken out from organism tissue, with both ends of the thread being held inside the rotary portion. Therefore, a duct does not have above-described constitution for above-described U-turn advance but has a constitution which can receive both ends of the thread and hold the both ends of the thread inside the rotary portion. Anchors, composed of a metal wire or the like, are provided with each of both ends of thread 306.

The constitution of this embodiment is similar to embodiments shown in FIG. 34 to FIG. 41 in that both ends of the thread are held inside the rotary portion and are taken out from a organism tissue, with the both ends of the thread being held inside the rotary portion.

The organism tissue suturing apparatus 300 is an apparatus for suturing a penetrated hole formed subcutaneously in a tissue membrane of an organism. The organism tissue suturing apparatus 300 includes a body part 302 having a predetermined length. The body part 302 includes a rotary portion 303 and can be inserted into said tissue of said organism from the hole, a needle member (in this embodiment, two needle members) 307a, 307b accommodated inside the body part 302, an anchor (in this embodiment, two anchors) 304a, 304b accommodated in the needle members 307a, 307b, a thread (in this embodiment, two threads) 305a, 305b joined with the anchors 304a, 304b respectively, a needle member operation portion 372 for advancing the needle members 307a, 307b toward the rotary portion 303 from a side surface, of said body part, disposed at a portion thereof rearward from the rotary portion 303, and an anchor pressing member (in this embodiment, two anchor pressing members) 306a, 306b for exiting the anchors 304a, 304b from a front end of the needle members respectively and pressing the anchors 304a, 304b into the rotary portion 304. The rotary portion 303 has a anchor receiving portion (in this embodiment, two anchor receiving portions) 303a, 303b for receiving the anchors 304a, 304b pressed into the rotary portion 303 by the anchor pressing members 306a, 306b, with the rotary portion 303 disposed in he tissue of said organism. An operation part 309 is disposed at a rear portion of the body part 302.

The organism tissue suturing apparatus 300 has two needle members and two anchors 304a, 304b. But, the organism tissue suturing apparatus 300 may has only one needle member and one anchor. It is desirable that the anchor receiving portions 303a, 303b are able to hold the anchors 304a, 304b.

As shown in FIG. 52, the body part 302 has a shaft 321 having accommodation portions 322a, 322b formed on a side surface of the shaft 321 and extending axially; and a hub (shaft hub) 326 disposed at a rear end of the shaft 321. As shown in FIG. 50, the shaft 321 has a body portion 321a in which the accommodation portions 322a, 322b are formed; and a front end portion 321b, extending forward from a front end of the body portion 321a, for rotatably supporting the rotary portion 303. As shown in FIG. 52, it is preferable that the accommodation portions 322a, 322b are grooves whose side surface is entirely open. The accommodation portions may be lumens having a side-surface opening at its front side. It is preferable that the shaft 321 has a length of 30 to 700 mm and has an outer diameter of 1.0 to 10.0 mm. The shaft 321 has a lumen 325 provided inside the shaft.

The accommodation portions 322a, 322b of the shaft 321 accommodate the hollow needle members 307a, 307b respectively. The needle member operation portion 372 for advancing the hollow needle members 307a, 307b from the body part 302 is disposed at the rear portion (preferably, rear end) of each of the hollow needle members 307a, 307b. As shown in FIG. 52, the hollow needle members 307a, 307b have cutting faces formed at the front end thereof respectively and anchor accommodation portions formed therein respectively. The hollow needle members 307a, 307b have a slit 371 for passing the thread fixed to the anchor.

The organism tissue suturing apparatus 300 has the anchor pressing members 306a, 306b for exiting the anchors 304a, 304b from the front end of the needle members respectively and pressing the anchors 304a, 304b into the rotary portion 304.

The accommodation portions 322a, 322b are formed inside the shaft 321 at positions in the vicinity of the side surface thereof. The accommodation portions 322a, 322b extend parallel with the axis of the shaft 321 to accommodate the hollow needle members 307a, 307b therein respectively. At the front end portion of the accommodation portions 322a, 322b, there are formed guide portions 323a, 323b for respectively advancing the hollow needle members obliquely and forwardly from the side surface of the body part 302.

The anchors 304a, 304b are tubular members or hollow members. The thread is fixed inside or outside of the anchor. It is preferable that the outer diameter of the anchor is 0.05 to 0.9 mm. It is preferable that the anchor has a length of 5.0 to 50.0 mm. The anchor may be made by elastic metal or elastic resin. The anchor is preferably made by super elastic alloy.

As shown in FIGS. 49 and 51, the body part 302 has a hub 326 disposed at its rear end portion The hub 326 has a duct accommodating the rear side of each of the hollow needle members. The hub 326 has a flange portion 326a to be operated by an operator.

As shown in FIG. 51, each of the hollow needle members 307a, 307b extends to the rear end of the shaft 321 through the accommodation portion, thus protruding rearward from the rear end of the shaft 321 and extending rearward inside the duct of the hub 326.

The rear end of each of the hollow needle members 307a, 307b is stopped to the needle member operation portion 372 slidable in the duct of the hub 326. Therefore by pressing the needle member operation portion 372 forward, the hollow needle members can be moved forward and the front portion thereof can be pressed out of the body part 302. The needle member operation portion may be provided for each of the hollow needle members. It is preferable that the hollow needle members are urged by an urging means in a direction in which they do not advance. More specifically, the needle member operation portion is always urged rearward by an elastic member 327 accommodated in the duct of the hub. It is preferable that a coil spring is used as the elastic member 327. The elastic member 327 may be provided between the flange portion 372a of the needle member operation portion 372 and the hub 326.

The needle member operation portion 372 has a duct for accommodating a proximal portion of the anchor pressing members 306a, 306b. As shown in FIG. 51, each of the anchor pressing members 306a, 306b extends inside the hollow needle members 307a, 307b and protrude from the rear end of the hollow needle members 307a, 307b and is connected an operation portion 361. The operation portion 361 for the anchor pressing members has a flange 361a. Therefore by pressing the operation portion 361 forward, the anchor pressing members 306a, 306b can be moved forward and the front portion thereof can be pressed to the anchors 304a, 304b. The anchors 304a, 304b can be exited from the hollow needle members 307a, 307b. The operation portion 361 for the anchor pressing members may be provided for each of the anchor pressing members. It is preferable that the operation portion 361 for the anchor pressing members is urged by an urging means in a direction in which they do not advance. More specifically, the operation portion 361 for the anchor pressing members is always urged rearward by an elastic member 373 accommodated in the duct of the needle member operation portion 372.

The anchor pressing members 306a, 306b has a projected tip end. The anchors 304a, 304b has a receiving portion at its rear end for receiving the projected tip end of the anchor pressing members 306a, 306b. The anchors 304a, 304b do not connected to the anchor pressing members 306a, 306b.

As shown in FIG. 50, the body part has a supporting pin 324 for rotatably supporting the rotary portion 303 having the anchor receiving portions 303a, 303b. The rotary portion 303 has a side-surface opening 303c, for receiving said supporting pin 324, formed long and axially extending to allow sliding of the supporting pin 324. The organism tissue suturing apparatus 300 has a rotary portion towing wire 331 which extends inside the body part 302 and is fixed to the rotary portion 303 at one end thereof.

As shown in FIG. 50, the rotary portion 303 has the anchor receiving portions 303a, 303b open at the upper end thereof. The anchor receiving portions 303a, 303b is a lumen having a first portion that obliquely extends toward at front side of the rotary portion 303, a second portion that extends toward at front side of the rotary portion 303 and a bending portion between the first and second portion. As shown in FIG. 54, the anchors 304a, 304b are received in the bending portion or a front side (the second portion) from bending portion. The bending portion of the lumen (anchor receiving portions) prevents it that anchors comes off from the anchor receiving portions.

In this organism tissue suturing apparatus 300, as shown in FIG. 53, the needle member operation portion 372 is pressed forward to advance the hollow needle members 304a, 304b obliquely from the front-side side surface of the body portion 321a of the body part 302 so that the hollow needle members 304a, 304b penetrate through the blood vessel. The operation portion 361 for the anchor pressing members is pressed forward to exit the anchors 304a, 304b from the front end of the hollow needle members 304a, 304b. Thereby as shown in FIG. 53, the anchors 304a, 304b reach the inside of the anchor receiving portion of the rotary portion 3. When the operation portion 361 for the anchor pressing members is pushed furthermore, as shown in FIG. 54, the anchors 304a, 304b are stored completely into the anchor receiving portions 303a, 303b.

In the above type of the organism tissue suturing apparatus, the apparatus may includes a rotation angle restriction function permitting a rotation of the rotary portion between a state in which the rotary portion is on an approximate extension line of an axis of said body part and a predetermined angle less than 90 degrees. The rotation angle restriction function is good to be the same as the one that is explained before.

As shown in FIG. 50, the organism tissue suturing apparatus 300 has a liquid-filling lumen, extending inside the body part 302, whose one end is open at a position in the vicinity of a front end thereof which can be inserted into the tissue of the organism and whose other end is open at the rear side of the body part; a three-way cock 11 connected to the liquid-filing lumen; a pulsation confirmation member 15 mounted on one port of the three-way cock 11; and a liquid-filing port 17 formed on another port of the three-way cock 11. The three-way cock 11 has an operation portion 16 for selectively communicating the liquid-filling lumen with one port thereof and another port thereof. The three-way cock 11 is connected to the body part 302 through a connection tube 19. The pulsation confirmation member 15 allows the operator from outside to visually observe a liquid surface that is deformed by a pressure applied to a liquid filled inside the three-way cock 11. The pulsation confirmation member 15 may have a pressure-sensitive film which is deformed by a change of the pressure applied to the liquid filled inside the three-way cock 11. As the liquid to be filled inside the three-way cock 11, physiologic saline can be preferably used.

Figure 55:
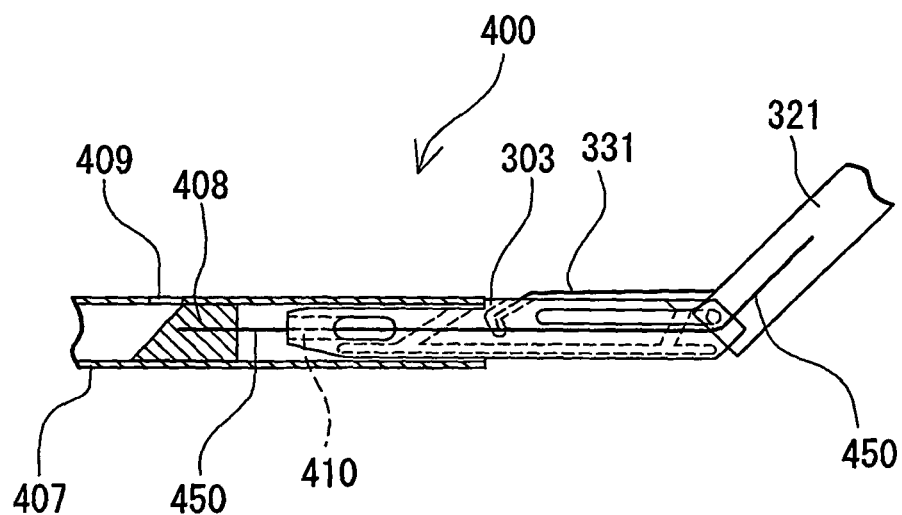
FIG. 55 is an explanatory view for explaining an organism tissue suturing apparatus according to another embodiment of the present invention.
Figure 56:
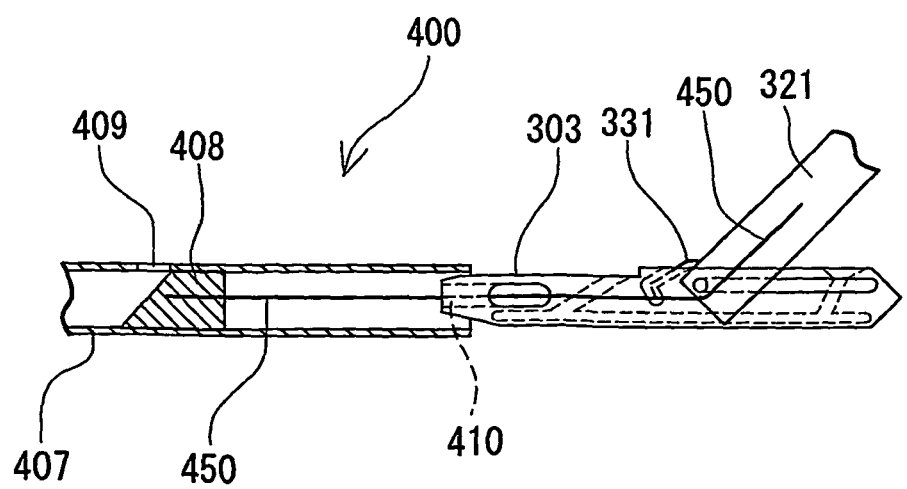
FIG. 56 is an explanatory view for explaining the operation of the organism tissue suturing apparatus of the present invention shown in FIG. 55.

In a type of apparatus like above-described organism tissue suturing apparatus 200, whose distal end portion is formed in tube-shaped, a tube 407 may be connected with the body part of the organism tissue suturing apparatus 400 by a connecting wire 450 like the organism tissue apparatus 400 as shown in FIG. 55 and FIG. 56.

In type of apparatus like above-described organism tissue suturing apparatuses 1, 50, 70, 100, 300 whose rotary portion is slidable, a tube 407 may be connected with a body part of the organism tissue suturing apparatus by a connecting wire 450 like organism tissue apparatus 400 as shown in FIG. 55 and FIG. 56. In the embodiments as shown in FIG. 55 and FIG. 56, the apparatus is type of apparatus whose rotary portion is slidable like apparatuses 1, 50, 70, 100, 300.

The connecting wire 450 extends inside a lumen 410 formed in the rotary portion 303. A distal end portion of the connecting wire 450 protrudes from the rotary portion 303. The connecting wire 450 is not fixed to the rotary portion. A rear end side of the connecting portion 450 is fixed to the body part The wire 450 is not fixed to the rotary portion 403. The wire 450 doesn't prevent the rotating and the sliding of the rotary portion 303. The tube 407 accommodates the front end potion of the rotary portion 303, with the front end portion slidable inside the rear end portion of the tube 407. That is, the rotary portion 303 is not fixed to the tube 407. The distal end portion of the connecting wire 450 enters inside the tube 407 and is fixed to the tube 407.

More specifically, the rotary portion 303 has a lumen 410 whose one end is open at a front end of the rotary portion 303 and the other end is open at a side surface in the middle portion of the rotary portion 303. The connecting wire 450 penetrates inside the lumen 410 formed inside rotary portion 303. The distal end portion of the connecting wire 450 protrudes from a front end opening of the rotary portion 303 and enters inside tube 407 and is fixed to tube 407 by a stopper 408. The proximal side of the connecting wire 450 protrudes from the side surface opening of the rotary portion 303 and is fixed to front end side portion 321 of the shaft body. A groove or a lumen, for fixing the connecting wire, is formed in the front end side portion of the body part of the shaft. The proximal end portion of the connecting wire 450 is accommodated in and fixed to the groove or the lumen. The connecting wire 450 is fixed to the front side 321 of the shaft body by using an adhesive, method of heat melting, mechanical engagement or the like.

The tube 407 has the front end opening, a side surface opening 409 and an accommodation portion for accommodating the front end portion of the rotary portion. The tube 407 is so formed that a guide wire can enters inside tube 407. It is preferable that the tube 407 has a length of 10 to 600 mm and has an outer diameter of 1.0 to 10.0 mm. As materials for the tube 407, it is possible to use the above-described materials used for the shaft 21, especially flexible materials are preferable.

It is preferable that the connecting wire 450 has a length of 10 to 200 mm and has an outer diameter of 1.0 to 10.0 mm. As materials for connecting wire 450, it is possible to use the above-described materials used for the wire 250. Silicon or hydrophilic resins may be applied to the outer surface of the wire 450 to increase the lubricity thereof.

Similarly to the tube 207 of the above-described suturing apparatus 200, the tube 407 is used as a guide wire lumen. In the suturing apparatus 300, the suturing apparatus can be inserted into by using a guide wire and the rotary portion 303 is not fixed to the tube 407. As shown in FIG. 56, when the rotary portion-towing wire (not shown) is pulled, only the rotary portion 303 moves rearward but the introduction wire does not move. Therefore the rotary portion 303 is capable of sliding smoothly.

INDUSTRIAL APPLICABILITY

An organism tissue suturing apparatus for suturing a penetrated hole formed subcutaneously in a tissue membrane of an organism comprises a body part, with a predetermined length, having a rotary portion and can be inserted into said tissue of said organism from said hole; two hollow needle members accommodated in a portion, inside said body part, rearward from said rotary portion; a needle member operation portion for advancing said hollow needle members toward said rotary portion from a side surface of said body part; and two openings disposed at a rear portion of said body part and communicating with an inside of said two hollow needle members, wherein said rotary portion has two needle member receiving portions for receiving a distal end of one of said hollow needle members and that of the other of said hollow needle members respectively pressed out of said body part; and a connection duct communicating with said two needle member receiving portions; and a duct for a suturing thread is formed in a range from one of said two openings to the other of said openings through an inside of one of said two hollow needle members, said connection duct, and an inside of the other of said two hollow needle members, when said two needle member receiving portions receive said hollow needle members respectively.

Therefore, in the organism tissue suturing apparatus of the embodiment of the invention, it is possible to perform an operation of piercing the tissue membrane of the organism with the needle by pressing the needle member operation portion forward in a short stroke so that the needle disposed a little outward from the tissue membrane of the organism are accommodated in the accommodation portion of the rotary portion disposed a little inward from the tissue membrane of the organism. Thus the suturing operation can be performed easily. Further by inserting the suturing thread into the duct for the suturing thread, it is possible to confirm the penetration of the suturing therethrough. Therefore it is possible to confirm that the operation of suturing the hole formed in the tissue membrane of the organism is being performed.

The invention claimed is:

1. An organism tissue suturing apparatus for suturing a penetrated hole formed subcutaneously in a tissue membrane of an organism, comprising:
    a body part, with a predetermined length, having a rotary portion and can be inserted into said tissue of said organism from said hole;
    two hollow needle members accommodated in a portion, inside said body part, rearward from said rotary portion;
    a needle member operation portion for advancing said two hollow needle members toward said rotary portion from a side surface of said body part; and
    two openings disposed at a rear-most portion of said body part and communicating with lumens of said two hollow needle members,
    wherein said rotary portion has two needle member receiving portions for receiving a distal end of one of said hollow needle members and that of the other of said hollow needle members respectively pressed out of said body part, a connection duct communicating with said two needle member receiving portions, said rotary portion includes a thread pull-out slit extending from an upper surface thereof and communicating with said two needle member receiving portions and said connection duct, and the thread pull-out slit is formed in a direction to avoid that said thread pull-out slit is located at an advancing direction of a suturing thread along an entire length of the thread pull-out slit, wherein the thread pull-out slit is oblique to a longitudinal axis of said rotary portion; and
    one continuous duct for a suturing thread is formed to range from one of said two openings to the other of said openings through one of said lumens of one of said two hollow needle members, said connection duct of said rotary portion, and the other of said lumens of the other of said two hollow needle members, when said two needle member receiving portions receive said hollow needle members respectively at a same time.

2. The organism tissue suturing apparatus according to claim 1, further comprising a suturing member which can be inserted into said connection duct for a suturing thread; and said suturing member includes a guide portion linearly formed of an elastic material and a suturing thread portion provided on said guide portion.

3. The organism tissue suturing apparatus according to claim 1, further comprising a rotary portion towing wire which extends inside said body part and is fixed to said rotary portion at one end thereof, wherein said body part has a supporting pin for rotatably supporting said rotary portion; and said rotary portion has a side-surface opening, for receiving said supporting pin, formed long and axially extending to allow sliding of said supporting pin.

4. The organism tissue suturing apparatus according to claim 1, further comprising a rotation angle restriction function permitting a rotation of said rotary portion between a state in which said rotary portion is on an approximate extension line of an axis of said body part and a predetermined angle less than 90 degrees.

5. The organism tissue suturing apparatus according to claim 1, further comprising an urging member for urging said needle member operation portion or said hollow needle member rearward and a stopper configured to stop said hollow needle members at a position pressed by said needle member operation portion.

6. The organism tissue suturing apparatus according to claim 1, wherein an opening is formed at a rear end of said needle member operation portion.

7. The organism tissue suturing apparatus according to claim 1, wherein said two openings exit at the rear-most portion of said organism tissue suturing apparatus, which is an extreme-most portion of said needle member operation portion.

8. The organism tissue suturing apparatus according to claim 1, wherein said rotary portion is attached to a fixed portion of said body part by at least one supporting pin, said at least one supporting pin is housed in at least one side surface opening that is longitudinal and allows the at least one supporting pin to slide in a longitudinal direction within the at least one side surface of said rotary portion.

9. The organism tissue suturing apparatus according to claim 1, wherein said rotary portion is at an endmost portion of said body part.

10. The organism tissue suturing apparatus according to claim 1, wherein a width of one of said two needle member receiving portions is greater than a diameter of said connection duct.

11. A method for suturing a penetrated hole formed in a blood vessel, comprising:
providing an organism tissue suturing apparatus including a body part, with a predetermined length, having a rotary portion rotatably supported to a distal portion of the body part and having a continuous communication duct;
inserting the rotary portion into the blood vessel from the penetrated hole;
rotating the rotary portion in the blood vessel until the body part becomes oblique at a predetermined angle with respect to an axis of the rotary portion, forming one continuous duct for a suturing thread formed to range from a first lumen of a first hollow needle member through a connection duct of said rotary portion, and a second lumen of a second hollow needle member;
advancing the first hollow needle member and the second hollow needle member from side surfaces of the body part to a first needle member receiving portion and a second needle member receiving portion of the rotary portion and penetrating through the blood vessel respectively; and
passing the suturing thread from a proximal end of the first hollow needle member through the first lumen of the first needle member, the first needle member receiving portion, said connection duct in the rotary portion, the second needle member receiving portion, and a second lumen of the second hollow needle member, to a proximal end of the second hollow needle member,
wherein said rotary portion includes a thread pull-out slit extending from an upper surface thereof and communicating with said first needle member receiving portion, said second needle member receiving portion, and said connection duct, and the thread pull-out slit is formed in a direction to avoid that said thread pull-out slit is located at an advancing direction of a suturing thread along an entire length of the thread pull-out slit, wherein the thread pull-out slit is oblique to a longitudinal axis of said rotary portion.

12. The method for suturing the penetrated hole formed in the blood vessel according to claim 11, further comprising:
returning the first hollow needle member and the second hollow needle member into the body part;
returning the rotary portion to an initial position; and
pulling out the organism tissue suturing apparatus out of the puncture site and leaving the suturing thread.

13. An organism tissue suturing apparatus for suturing a penetrated hole formed subcutaneously in a tissue membrane of an organism, comprising:
a body part, with a predetermined length, having a front side part that can be inserted into said tissue of said organism from said hole, a rotary portion can be inserted into said tissue of said organism from said hole and a rear portion that can not be inserted into said organism;
two hollow needle members accommodated in a portion, inside said body part, rearward from said rotary portion;
a needle member operation portion for advancing said two hollow needle members toward said rotary portion from a side surface of said body part; and
two openings disposed at said rear portion of said body part and communicating with lumens of said two hollow needle members,
wherein said rotary portion is rotatably supported to a front end of said body part and has two needle member receiving portions for receiving a distal end of one of said hollow needle members and that of the other of said hollow needle members respectively pressed out of said body part, a connection duct communicating with said two needle member receiving portions, said rotary portion includes a thread pull-out slit extending from an upper surface thereof and communicating with said two needle member receiving portions and said connection duct, and the thread pull-out slit is formed in a direction to avoid that said thread pull-out slit is located at an advancing direction of a suturing thread along an entire length of the thread pull-out slit, wherein the thread pull-out slit is oblique to a longitudinal axis of said rotary portion; and
one continuous duct for a suturing thread is formed to range from one of said two openings to the other of said openings through one of said lumens of one of said two hollow needle members, said connection duct of said rotary portion, and the other of said lumens of the other of said two hollow needle members, when said two needle member receiving portions receive said hollow needle members respectively at a same time.

14. The organism tissue suturing apparatus according to claim 13, further comprising:
an operation part disposed at said rear portion, of the body part, and said two openings are disposed at said operation part.

15. An organism tissue suturing apparatus for suturing a penetrated hole formed subcutaneously in a tissue membrane of an organism, comprising:
a body part, with a predetermined length, having a front side part can be inserted into said tissue of said organism from said hole, a rotary portion that can be inserted into said tissue of said organism from said hole, and a rear portion that can not be inserted into said organism;
first and second hollow needle members accommodated in a portion, inside said body part, rearward from said rotary portion;
a needle member operation portion for advancing said first and second hollow needle members toward said rotary portion from a side surface of said body part;
a first opening disposed at said rear portion of said body part and communicating with a first lumen of said first hollow needle member; and
a second opening disposed at said rear portion of said body part and communicating with a second lumen of said second hollow needle member,
wherein said rotary portion is rotatably supported to a front end of said body part and has a first receiving portion for receiving a distal end of said first hollow needle member pressed out of said body part and a second receiving portion for receiving a distal end of said second hollow needle member pressed out of said body part and a connection duct communicating with said first and second receiving portions, said rotary portion includes a thread pull-out slit extending from an upper surface thereof and communicating with said first and second receiving portions and said connection duct, and the thread pull-out slit is formed in a direction to avoid that said thread pull-out slit is located at an advancing direction of a suturing thread along an entire length of the thread pull-out slit, wherein the thread pull-out slit is oblique to a longitudinal axis of said rotary portion; and one continuous duct for a suturing thread is formed to range from said first opening to said second opening through said first lumen of said first hollow needle member, said connection duct of said rotary portion, and said second lumen of said second hollow needle member, when said first receiving portion receives the distal end of said first hollow needle member pressed out of said body part and said second receiving portion receives the distal end of said second hollow needle member pressed out of said body part.

16. The organism tissue suturing apparatus according to claim 15, further comprising:

an operation part disposed at said rear portion of the body part, and said two openings are disposed at said operation part.

* * * * *

UNITED STATES PATENT AND TRADEMARK OFFICE
CERTIFICATE OF CORRECTION

| | |
|---|---|
| PATENT NO. | : 8,603,110 B2 |
| APPLICATION NO. | : 10/511441 |
| DATED | : December 10, 2013 |
| INVENTOR(S) | : Tomoji Maruyama et al. |

It is certified that error appears in the above-identified patent and that said Letters Patent is hereby corrected as shown below:

In the Specification

Column 32, line 45, replace "potion" with --portion--.

Signed and Sealed this
Tenth Day of June, 2014

Michelle K. Lee
*Deputy Director of the United States Patent and Trademark Office*